(12) United States Patent
Oxvig et al.

(10) Patent No.: US 11,318,158 B2
(45) Date of Patent: May 3, 2022

(54) PAPPALYSIN REGULATOR

(71) Applicant: Aarhus Universitet, Aarhus C (DK)

(72) Inventors: Claus Oxvig, Højbjerg (DK); Jakob Hauge Mikkelsen, Horning (DK); Malene Runge Jepsen, Aarhus N (DK)

(73) Assignee: Aarhus Universitet, Aarhus C (DK)

( * ) Notice: Subject to any disclaimer, the term of this patent is extended or adjusted under 35 U.S.C. 154(b) by 0 days.

(21) Appl. No.: 16/599,706

(22) Filed: Oct. 11, 2019

(65) Prior Publication Data

US 2020/0261490 A1 Aug. 20, 2020

Related U.S. Application Data

(63) Continuation of application No. 14/889,997, filed as application No. PCT/DK2014/050131 on May 12, 2014, now abandoned.

(30) Foreign Application Priority Data

May 10, 2013 (DK) .......................... PA 2013 70259

(51) Int. Cl.
| | |
|---|---|
| *G01N 33/53* | (2006.01) |
| *G01N 33/60* | (2006.01) |
| *C07K 14/00* | (2006.01) |
| *C07K 16/00* | (2006.01) |
| *C07K 17/00* | (2006.01) |
| *A61K 31/713* | (2006.01) |
| *C07K 16/40* | (2006.01) |
| *C12N 9/64* | (2006.01) |
| *A61K 38/22* | (2006.01) |
| *C07K 14/575* | (2006.01) |
| *C07K 16/38* | (2006.01) |
| *C07K 16/18* | (2006.01) |

(52) U.S. Cl.
CPC ............ *A61K 31/713* (2013.01); *A61K 38/22* (2013.01); *C07K 14/575* (2013.01); *C07K 16/18* (2013.01); *C07K 16/38* (2013.01); *C07K 16/40* (2013.01); *C12N 9/6489* (2013.01); *C12Y 304/24079* (2013.01); *C07K 2317/76* (2013.01); *G01N 33/53* (2013.01)

(58) Field of Classification Search
None
See application file for complete search history.

(56) References Cited

U.S. PATENT DOCUMENTS 5,994,103 A 11/1999 Olsen et al.

FOREIGN PATENT DOCUMENTS

| WO | 0130969 A2 | 5/2001 |
|---|---|---|
| WO | 0132926 A2 | 5/2001 |
| WO | 2005035732 A2 | 4/2005 |
| WO | 2008101118 A2 | 8/2008 |
| WO | 2009015050 A2 | 1/2009 |
| WO | 2009092806 A2 | 7/2009 |
| WO | 2010020004 A1 | 2/2010 |

OTHER PUBLICATIONS

Kloverpris et al. Stanniocalcin-1 potently inhibits the proteolytic activity of the metalloproteinase pregnancy-associated plasma protein-A. The Journal of Biological Chemistry vol. 290, No. 36:21915-21924 (Sep. 2015). (Year: 2015).*
Jepsen et al. Stanniocalcin-2 inhibits mammalian growth by proteolytic inhibition of the insulin-like growth factor axis. The Journal of Biological Chemistry vol. 290, No. 6:3430-3439 (Feb. 2015). (Year: 2015).*
Bhattacharya et al. Impact of genetic variation on three dimensional structure and function of proteins PLOS One pp. 1-22, Mar. 15, 2017). (Year: 2017).*
Abbas et al. Cellular and Molecular Immunology, Chapter 3, Antibodies and Antigens. pp. 47-48; Second Edition, Copy Right 1994, 1991 by W.B. Saunders Company, PA). (Year: 1991).*
Fenton et al. Rheostat positions: A new classification of protein positions relevant to pharmacogenomics Medicinal Chemistry Research 29:1133-1146; (2020). (Year: 2020).*
Gua et al. Protein tolerance to random amino acid change. PNAS USA 101 (25):9205-10; (2004). (Year: 2004).*
T-Chen, et al., "Discovery and characterization of human antibody inhibitors of pregnancy-associated plasma protein-A", Biological Chemistry, (2007), vol. 388, No. 5, pp. 507-512.
H. Pan, et al., Protein Secretion Is Required for Pregnancy-Associated Plasma Protein-A to Promote Lung Cancer Growth In Vivo, PLOS One, Nov. 2012, vol. 7, Issue 11, e48799.
K. Tamura, et al., "Stanniocalcin 2 overexpression in castration-resistant prostate cancer and aggressive prostate cancer", Cancer Sci, Japanese Cancer Association, May 2009, vol. 100, No. 5, pp. 914-919.
J.H. Mikkelsen, et al., "Indirect targeting of IGF receptor signaling in vivo by substrate-selective inhibition of PAPP-A proteolytic activity", Oncotarget, (2014), vol. 5, No. 4, pp. 1014-1025.
M.R. Jepsen, et al., "The proteolytic activity of pregnancy-associated plasma protein-A is potentially regulated by stanniocalcin-1 and -2 during human ovarian follicle development", Human Reproduction (2016), vol. 0, No. 0, pp. 1-9.

(Continued)

*Primary Examiner* — Joanne Hama
*Assistant Examiner* — Regina M DeBerry
(74) *Attorney, Agent, or Firm* — Dinsmore & Shohl LLP; Weston R. Gould

(57) ABSTRACT

A method is provided of decreasing or increasing the activity of a Pappalysin polypeptide by decreasing or increasing the level of interacting Pappalysin and stanniocalcin polypeptides. A method is also provided of preventing, treating or ameliorating a clinical condition in a mammalian subject, such as a human being, said method comprising administering to said mammalian subject, such as human being an effective amount of a stanniocalcin polypeptide. Moreover, a method is provided of preventing, treating or ameliorating a clinical condition in a mammalian subject, such as a human being, said method comprising administering to said mammalian subject, such as human being an effective amount of an agent capable of antagonizing interaction of a stanniocalcin polypeptide with a Pappalysin polypeptide.

11 Claims, 16 Drawing Sheets

Specification includes a Sequence Listing.

(56) References Cited

OTHER PUBLICATIONS

Ngo et al., 1994, The Protein Folding Problem and Tertiary Structure Prediction, Merz et al., eds, Birkhauser, Boston, pp. 433-506.
Yokobori, T. et al; "Clinical Significance of Stanniocalcin 2 as a Prognostic Marker in Gastric Cancer"; Annals of Surgical Oncology; Apr. 27, 201 O; vol. 17 pp. 2601-2607.
Soe, Rikke et al; "Expression of recombinant murine pregnancy-associated plasma protein-A (PAPP-A) and a novel variant (PAPP-Ai) with differential proteolytic activity"; Eur J. Biochem. 269; (2002) pp. 2247-2256.
Overgaard, M.T. et al; "Inhibition of proteolysis by the proform of eosinophil major basic protein (proMBP) requires covalent binding to its target proteinase"; FEBS Letters 560 (1-3); Feb. 27, 2004, pp. 147-152 (abstract only).
Overgaard, Michael T. et al; "Expression of Recombinant Human Pregnancy-associated Plasma Protein-A and Identification of the Proform of Eosinophil Major Basic Protein as Its Physiological Inhibitor"; The Journal of Biological Chemistry; vol. 275; No. 40; Oct. 6, 2000; pp. 31128-31133.
Liu, Guangzhi et al; Stanniocalcin 1 and Ovarian Tumorigenesis; Advance Access Publication on May 18, 2010; JNCI, vol. 102, Issue 11, pp. 812-827.
Johnston, Jennifer et al; "Human stanniocalcin-1 or -2 expressed in mice reduces bone size and severely inhibits cranial intramembranous bone growth"; Transgenic Res (2010) 19: pp. 1017-1039.
Gagliardi, Anthony D. et al; "Human stanniocalcin-2 exhibits potent growth-suppressive properties in transgenic mice independently of growth hormone and IGFs"; Am J. Physiol Endocrinol Metab 288; Sep. 14, 2004, pp. E92-E105.
Esseghir, Selma et al; "Identification of NTN4, TRA1, and STC2 as Prognostic Markers in Breast Cancer in a Screen for Signal Sequence Encoding Proteins"; Clin Cancer Res 2007; 13:3, pp. 3164-3173; Jun. 1, 2007.
DuBridge, Robert B. et al; "Analysis of Mutation in Human Cells by using an Epstein-Barr Virus Shuttle System"; Molecular and Cellular Biology; Jan. 1987; vol. 7, No. 1; pp. 379-387.
Bowie, J. et al., Deciphering the Message in Protein Sequences: Tolerance to Amino Acid Substitutions, Science, 247(4948):1306-1310, Mar. 16, 1990.
Wells, J. et al., Additivity of Mutational Effects in Proteins, Biochemistry, 29(37) :8509-8517, 1990.
Wang, D. et al., A Single Amino Acid Determines Lysophospholipid Specificity of the SIP 1 (EDG 1) and LPA1 (EDG2) Phospholipid Growth Factor Receptors, Journal of Biological Chemistry, 276(52):49213-49220, Dec. 28, 2001.

\* cited by examiner

Figure 5
A) STC1
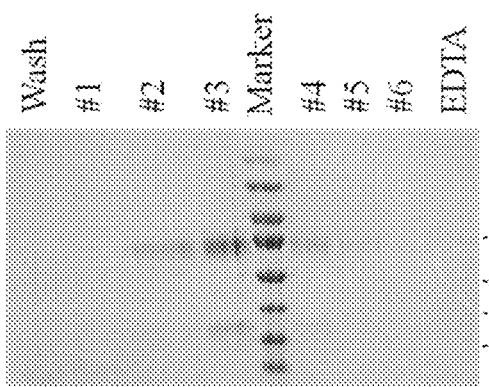
B) STC2
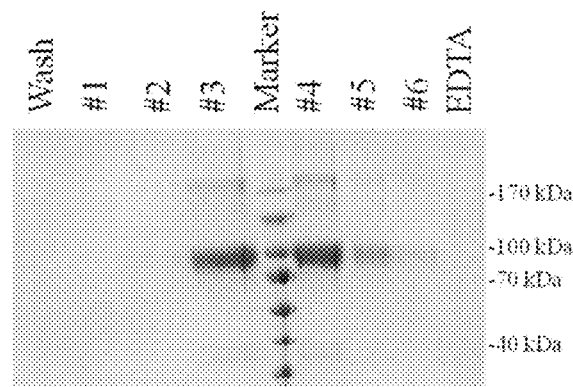

Figure 9
A
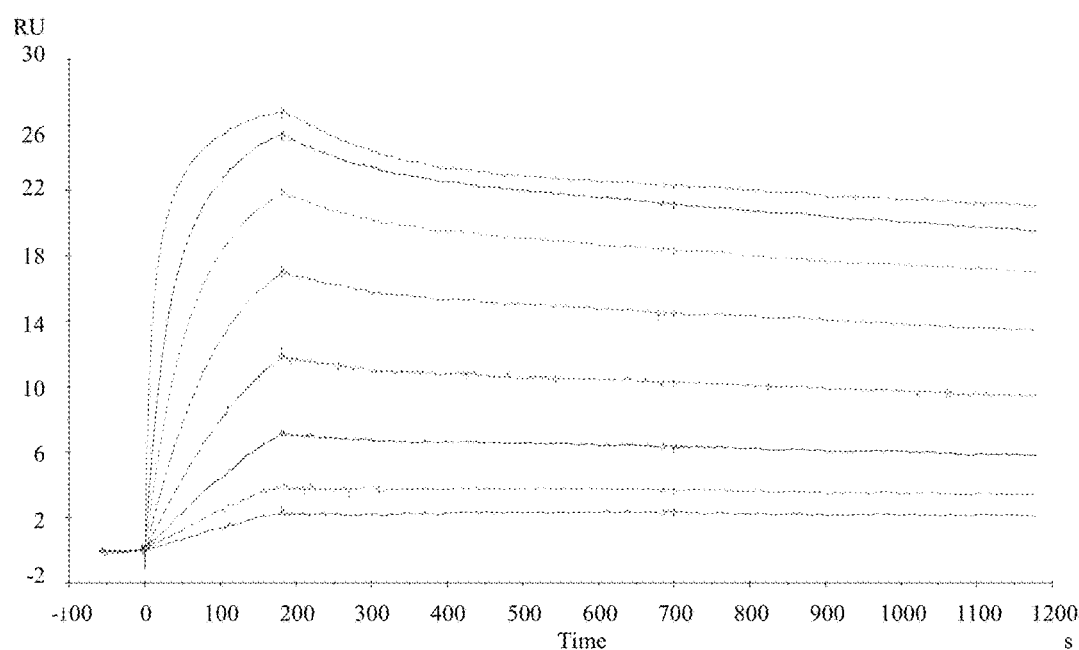
B
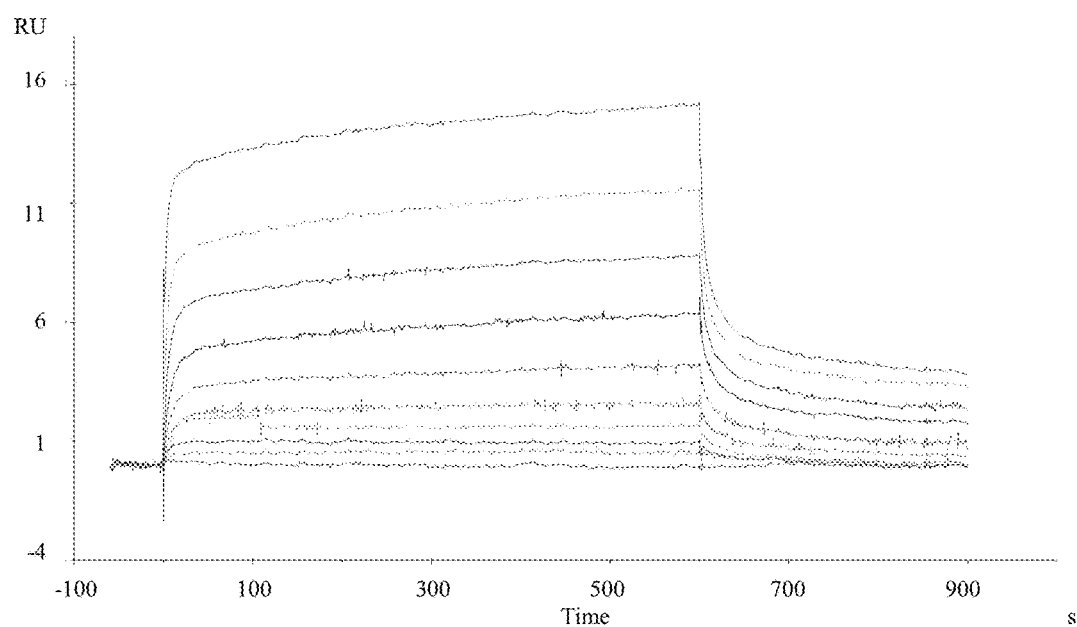

Figure 10
A
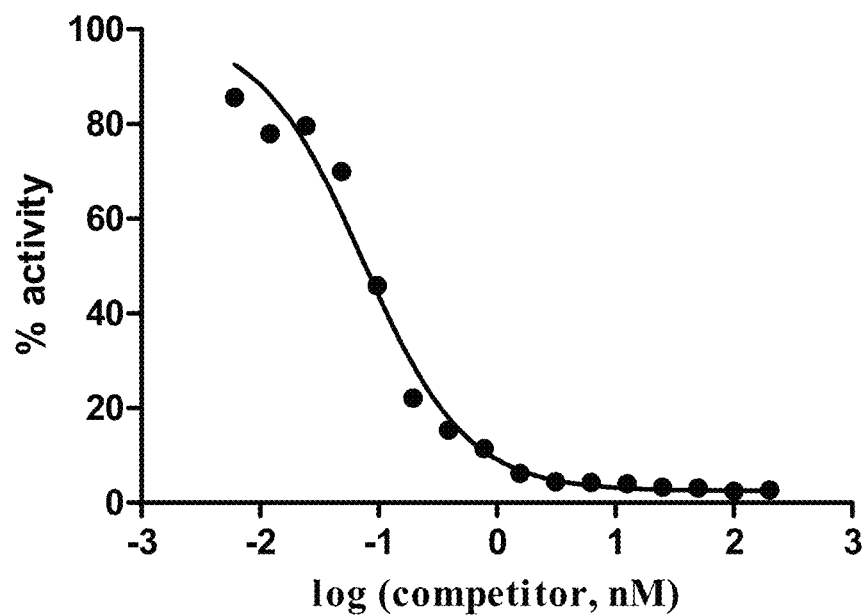
B
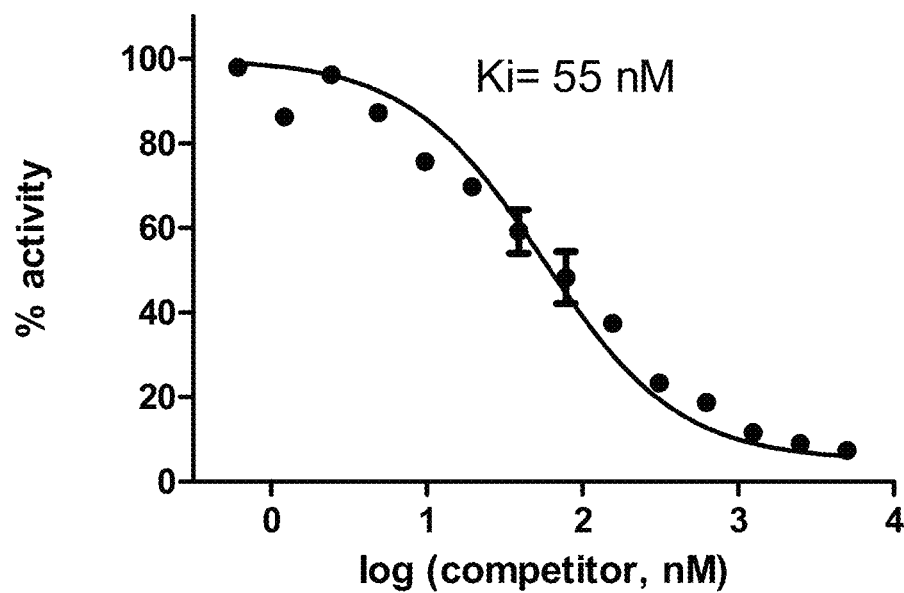

Figure 15 (Suppl. 1

Figure 16

SEQUENCE LISTING

<160> NUMBER OF SEQ ID NOS: 22

<210> SEQ ID NO 1
<211> LENGTH: 247
<212> TYPE: PRT
<213> ORGANISM: Homo sapiens

<400> SEQUENCE: 1

```
Met Leu Gln Asn Ser Ala Val Leu Leu Val Leu Val Ile Ser Ala Ser
1               5                   10                  15

Ala Thr His Glu Ala Glu Gln Asn Asp Ser Val Ser Pro Arg Lys Ser
            20                  25                  30

Arg Val Ala Ala Gln Asn Ser Ala Glu Val Val Arg Cys Leu Asn Ser
        35                  40                  45

Ala Leu Gln Val Gly Cys Gly Ala Phe Ala Cys Leu Glu Asn Ser Thr
    50                  55                  60

Cys Asp Thr Asp Gly Met Tyr Asp Ile Cys Lys Ser Phe Leu Tyr Ser
65                  70                  75                  80

Ala Ala Lys Phe Asp Thr Gln Gly Lys Ala Phe Val Lys Glu Ser Leu
                85                  90                  95

Lys Cys Ile Ala Asn Gly Val Thr Ser Lys Val Phe Leu Ala Ile Arg
            100                 105                 110

Arg Cys Ser Thr Phe Gln Arg Met Ile Ala Glu Val Gln Glu Glu Cys
        115                 120                 125

Tyr Ser Lys Leu Asn Val Cys Ser Ile Ala Lys Arg Asn Pro Glu Ala
    130                 135                 140

Ile Thr Glu Val Val Gln Leu Pro Asn His Phe Ser Asn Arg Tyr Tyr
145                 150                 155                 160

Asn Arg Leu Val Arg Ser Leu Leu Glu Cys Asp Glu Asp Thr Val Ser
                165                 170                 175

Thr Ile Arg Asp Ser Leu Met Glu Lys Ile Gly Pro Asn Met Ala Ser
            180                 185                 190
```

Leu Phe His Ile Leu Gln Thr Asp His Cys Ala Gln Thr His Pro Arg
            195                 200                 205

Ala Asp Phe Asn Arg Arg Thr Asn Glu Pro Gln Lys Leu Lys Val
        210                 215                 220

Leu Leu Arg Asn Leu Arg Gly Glu Glu Asp Ser Pro Ser His Ile Lys
225                 230                 235                 240

Arg Thr Ser His Glu Ser Ala
            245

<210> SEQ ID NO 2
<211> LENGTH: 302
<212> TYPE: PRT
<213> ORGANISM: Homo sapiens

<400> SEQUENCE: 2

Met Cys Ala Glu Arg Leu Gly Gln Phe Met Thr Leu Ala Leu Val Leu
1               5                   10                  15

Ala Thr Phe Asp Pro Ala Arg Gly Thr Asp Ala Thr Asn Pro Pro Glu
            20                  25                  30

Gly Pro Gln Asp Arg Ser Ser Gln Gln Lys Gly Arg Leu Ser Leu Gln
        35                  40                  45

Asn Thr Ala Glu Ile Gln His Cys Leu Val Asn Ala Gly Asp Val Gly
    50                  55                  60

Cys Gly Val Phe Glu Cys Phe Glu Asn Asn Ser Cys Glu Ile Arg Gly
65                  70                  75                  80

Leu His Gly Ile Cys Met Thr Phe Leu His Asn Ala Gly Lys Phe Asp
                85                  90                  95

Ala Gln Gly Lys Ser Phe Ile Lys Asp Ala Leu Lys Cys Lys Ala His
            100                 105                 110

Ala Leu Arg His Arg Phe Gly Cys Ile Ser Arg Lys Cys Pro Ala Ile
        115                 120                 125

Arg Glu Met Val Ser Gln Leu Gln Arg Glu Cys Tyr Leu Lys His Asp
    130                 135                 140

Leu Cys Ala Ala Ala Gln Glu Asn Thr Arg Val Ile Val Glu Met Ile
145                 150                 155                 160

His Phe Lys Asp Leu Leu His Glu Pro Tyr Val Asp Leu Val Asn
                165                 170                 175

Leu Leu Leu Thr Cys Gly Glu Glu Val Lys Glu Ala Ile Thr His Ser
            180                 185                 190

Val Gln Val Gln Cys Glu Gln Asn Trp Gly Ser Leu Cys Ser Ile Leu
        195                 200                 205

Ser Phe Cys Thr Ser Ala Ile Gln Lys Pro Pro Thr Ala Pro Pro Glu
    210                 215                 220

Arg Gln Pro Gln Val Asp Arg Thr Lys Leu Ser Arg Ala His His Gly
225                 230                 235                 240

Glu Ala Gly His His Leu Pro Gly Pro Ser Ser Arg Glu Thr Gly Arg
                245                 250                 255

Gly Ala Lys Gly Glu Arg Gly Ser Lys Ser His Pro Asn Ala His Ala
            260                 265                 270

Arg Gly Arg Val Gly Gly Leu Gly Ala Gln Gly Pro Ser Gly Ser Ser
        275                 280                 285

Glu Trp Glu Asp Glu Gln Ser Glu Tyr Ser Asp Ile Arg Arg
    290                 295                 300

```
<210> SEQ ID NO 3
<211> LENGTH: 1627
<212> TYPE: PRT
<213> ORGANISM: Homo sapiens

<400> SEQUENCE: 3
```

| | | | | | | | | | | | | | | | |
|---|---|---|---|---|---|---|---|---|---|---|---|---|---|---|---|
| Met | Arg | Leu | Trp | Ser | Trp | Val | Leu | His | Leu | Gly | Leu | Leu | Ser | Ala | Ala |
| 1 | | | | 5 | | | | | 10 | | | | | 15 | |
| Leu | Gly | Cys | Gly | Leu | Ala | Glu | Arg | Pro | Arg | Ala | Arg | Arg | Asp | Pro | |
| | | | 20 | | | | | 25 | | | | | 30 | | |
| Arg | Ala | Gly | Arg | Pro | Pro | Arg | Pro | Ala | Ala | Gly | Pro | Ala | Thr | Cys | Ala |
| | | | 35 | | | | | 40 | | | | | 45 | | |
| Thr | Arg | Ala | Ala | Arg | Gly | Arg | Ala | Ser | Pro | Pro | Pro | Pro | Pro | Pro | Pro |
| | 50 | | | | | 55 | | | | | 60 | | | | |
| Pro | Gly | Gly | Ala | Trp | Glu | Ala | Val | Arg | Val | Pro | Arg | Arg | Arg | Gln | Gln |
| 65 | | | | | 70 | | | | | 75 | | | | | 80 |
| Arg | Glu | Ala | Arg | Gly | Ala | Thr | Glu | Glu | Pro | Ser | Pro | Pro | Ser | Arg | Ala |
| | | | | 85 | | | | | 90 | | | | | 95 | |
| Leu | Tyr | Phe | Ser | Gly | Arg | Gly | Glu | Gln | Leu | Arg | Leu | Arg | Ala | Asp | Leu |
| | | | 100 | | | | | 105 | | | | | 110 | | |
| Glu | Leu | Pro | Arg | Asp | Ala | Phe | Thr | Leu | Gln | Val | Trp | Leu | Arg | Ala | Glu |
| | | 115 | | | | | 120 | | | | | 125 | | | |
| Gly | Gly | Gln | Arg | Ser | Pro | Ala | Val | Ile | Thr | Gly | Leu | Tyr | Asp | Lys | Cys |
| 130 | | | | | 135 | | | | | 140 | | | | | |
| Ser | Tyr | Ile | Ser | Arg | Asp | Arg | Gly | Trp | Val | Val | Gly | Ile | His | Thr | Ile |
| 145 | | | | | 150 | | | | | 155 | | | | | 160 |
| Ser | Asp | Gln | Asp | Asn | Lys | Asp | Pro | Arg | Tyr | Phe | Phe | Ser | Leu | Lys | Thr |
| | | | | 165 | | | | | 170 | | | | | 175 | |
| Asp | Arg | Ala | Arg | Gln | Val | Thr | Thr | Ile | Asn | Ala | His | Arg | Ser | Tyr | Leu |
| | | | 180 | | | | | 185 | | | | | 190 | | |
| Pro | Gly | Gln | Trp | Val | Tyr | Leu | Ala | Ala | Thr | Tyr | Asp | Gly | Gln | Phe | Met |
| | | 195 | | | | | 200 | | | | | 205 | | | |
| Lys | Leu | Tyr | Val | Asn | Gly | Ala | Gln | Val | Ala | Thr | Ser | Gly | Glu | Gln | Val |
| 210 | | | | | 215 | | | | | 220 | | | | | |
| Gly | Gly | Ile | Phe | Ser | Pro | Leu | Thr | Gln | Lys | Cys | Lys | Val | Leu | Met | Leu |
| 225 | | | | | 230 | | | | | 235 | | | | | 240 |
| Gly | Gly | Ser | Ala | Leu | Asn | His | Asn | Tyr | Arg | Gly | Tyr | Ile | Glu | His | Phe |
| | | | | 245 | | | | | 250 | | | | | 255 | |
| Ser | Leu | Trp | Lys | Val | Ala | Arg | Thr | Gln | Arg | Glu | Ile | Leu | Ser | Asp | Met |
| | | | 260 | | | | | 265 | | | | | 270 | | |
| Glu | Thr | His | Gly | Ala | His | Thr | Ala | Leu | Pro | Gln | Leu | Leu | Leu | Gln | Glu |
| | | 275 | | | | | 280 | | | | | 285 | | | |
| Asn | Trp | Asp | Asn | Val | Lys | His | Ala | Trp | Ser | Pro | Met | Lys | Asp | Gly | Ser |
| | 290 | | | | | 295 | | | | | 300 | | | | |
| Ser | Pro | Lys | Val | Glu | Phe | Ser | Asn | Ala | His | Gly | Phe | Leu | Leu | Asp | Thr |
| 305 | | | | | 310 | | | | | 315 | | | | | 320 |
| Ser | Leu | Glu | Pro | Pro | Leu | Cys | Gly | Gln | Thr | Leu | Cys | Asp | Asn | Thr | Glu |
| | | | | 325 | | | | | 330 | | | | | 335 | |
| Val | Ile | Ala | Ser | Tyr | Asn | Gln | Leu | Ser | Ser | Phe | Arg | Gln | Pro | Lys | Val |
| | | | 340 | | | | | 345 | | | | | 350 | | |
| Val | Arg | Tyr | Arg | Val | Val | Asn | Leu | Tyr | Glu | Asp | Asp | His | Lys | Asn | Pro |
| | | 355 | | | | | 360 | | | | | 365 | | | |
| Thr | Val | Thr | Arg | Glu | Gln | Val | Asp | Phe | Gln | His | His | Gln | Leu | Ala | Glu |
| 370 | | | | | 375 | | | | | 380 | | | | | |

```
Ala Phe Lys Gln Tyr Asn Ile Ser Trp Glu Leu Asp Val Leu Glu Val
385                 390                 395                 400

Ser Asn Ser Ser Leu Arg Arg Arg Leu Ile Leu Ala Asn Cys Asp Ile
            405                 410                 415

Ser Lys Ile Gly Asp Glu Asn Cys Asp Pro Glu Cys Asn His Thr Leu
        420                 425                 430

Thr Gly His Asp Gly Gly Asp Cys Arg His Leu Arg His Pro Ala Phe
        435                 440                 445

Val Lys Lys Gln His Asn Gly Val Cys Asp Met Asp Cys Asn Tyr Glu
    450                 455                 460

Arg Phe Asn Phe Asp Gly Gly Glu Cys Cys Asp Pro Glu Ile Thr Asn
465                 470                 475                 480

Val Thr Gln Thr Cys Phe Asp Pro Asp Ser Pro His Arg Ala Tyr Leu
                485                 490                 495

Asp Val Asn Glu Leu Lys Asn Ile Leu Lys Leu Asp Gly Ser Thr His
                500                 505                 510

Leu Asn Ile Phe Phe Ala Lys Ser Ser Glu Glu Glu Leu Ala Gly Val
        515                 520                 525

Ala Thr Trp Pro Trp Asp Lys Glu Ala Leu Met His Leu Gly Gly Ile
        530                 535                 540

Val Leu Asn Pro Ser Phe Tyr Gly Met Pro Gly His Thr His Thr Met
545                 550                 555                 560

Ile His Glu Ile Gly His Ser Leu Gly Leu Tyr His Val Phe Arg Gly
                565                 570                 575

Ile Ser Glu Ile Gln Ser Cys Ser Asp Pro Cys Met Glu Thr Glu Pro
            580                 585                 590

Ser Phe Glu Thr Gly Asp Leu Cys Asn Asp Thr Asn Pro Ala Pro Lys
        595                 600                 605

His Lys Ser Cys Gly Asp Pro Gly Pro Gly Asn Asp Thr Cys Gly Phe
        610                 615                 620

His Ser Phe Phe Asn Thr Pro Tyr Asn Asn Phe Met Ser Tyr Ala Asp
625                 630                 635                 640

Asp Asp Cys Thr Asp Ser Phe Thr Pro Asn Gln Val Ala Arg Met His
                645                 650                 655

Cys Tyr Leu Asp Leu Val Tyr Gln Gly Trp Gln Pro Ser Arg Lys Pro
            660                 665                 670

Ala Pro Val Ala Leu Ala Pro Gln Val Leu Gly His Thr Thr Asp Ser
        675                 680                 685

Val Thr Leu Glu Trp Phe Pro Pro Ile Asp Gly His Phe Phe Glu Arg
690                 695                 700

Glu Leu Gly Ser Ala Cys His Leu Cys Leu Glu Gly Arg Ile Leu Val
705                 710                 715                 720

Gln Tyr Ala Ser Asn Ala Ser Ser Pro Met Pro Cys Ser Pro Ser Gly
            725                 730                 735

His Trp Ser Pro Arg Glu Ala Glu Gly His Pro Asp Val Glu Gln Pro
        740                 745                 750

Cys Lys Ser Ser Val Arg Thr Trp Ser Pro Asn Ser Ala Val Asn Pro
        755                 760                 765

His Thr Val Pro Pro Ala Cys Pro Glu Pro Gln Gly Cys Tyr Leu Glu
        770                 775                 780

Leu Glu Phe Leu Tyr Pro Leu Val Pro Glu Ser Leu Thr Ile Trp Val
785                 790                 795                 800
```

```
Thr Phe Val Ser Thr Asp Trp Asp Ser Ser Gly Ala Val Asn Asp Ile
            805                 810                 815

Lys Leu Leu Ala Val Ser Gly Lys Asn Ile Ser Leu Gly Pro Gln Asn
        820                 825                 830

Val Phe Cys Asp Val Pro Leu Thr Ile Arg Leu Trp Asp Val Gly Glu
        835                 840                 845

Glu Val Tyr Gly Ile Gln Ile Tyr Thr Leu Asp Glu His Leu Glu Ile
        850                 855                 860

Asp Ala Ala Met Leu Thr Ser Thr Ala Asp Thr Pro Leu Cys Leu Gln
865                 870                 875                 880

Cys Lys Pro Leu Lys Tyr Lys Val Val Arg Asp Pro Leu Gln Met
            885                 890                 895

Asp Val Ala Ser Ile Leu His Leu Asn Arg Lys Phe Val Asp Met Asp
            900                 905                 910

Leu Asn Leu Gly Ser Val Tyr Gln Tyr Trp Val Ile Thr Ile Ser Gly
            915                 920                 925

Thr Glu Glu Ser Glu Pro Ser Pro Ala Val Thr Tyr Ile His Gly Ser
    930                 935                 940

Gly Tyr Cys Gly Asp Gly Ile Ile Gln Lys Asp Gln Gly Glu Gln Cys
945                 950                 955                 960

Asp Asp Met Asn Lys Ile Asn Gly Asp Gly Cys Ser Leu Phe Cys Arg
            965                 970                 975

Gln Glu Val Ser Phe Asn Cys Ile Asp Glu Pro Ser Arg Cys Tyr Phe
            980                 985                 990

His Asp Gly Asp Gly Val Cys Glu  Glu Phe Glu Gln Lys  Thr Ser Ile
            995                 1000                1005

Lys Asp Cys Gly Val Tyr Thr  Pro Gln Gly Phe Leu  Asp Gln Trp
    1010                1015                1020

Ala Ser  Asn Ala Ser Val Ser  His Gln Asp Gln Gln  Cys Pro Gly
    1025                1030                1035

Trp Val  Ile Ile Gly Gln Pro  Ala Ala Ser Gln Val  Cys Arg Thr
    1040                1045                1050

Lys Val  Ile Asp Leu Ser Glu  Gly Ile Ser Gln His  Ala Trp Tyr
    1055                1060                1065

Pro Cys  Thr Ile Ser Tyr Pro  Tyr Ser Gln Leu Ala  Gln Thr Thr
    1070                1075                1080

Phe Trp  Leu Arg Ala Tyr Phe  Ser Gln Pro Met Val  Ala Ala Ala
    1085                1090                1095

Val Ile  Val His Leu Val Thr  Asp Gly Thr Tyr Tyr  Gly Asp Gln
    1100                1105                1110

Lys Gln  Glu Thr Ile Ser Val  Gln Leu Leu Asp Thr  Lys Asp Gln
    1115                1120                1125

Ser His  Asp Leu Gly Leu His  Val Leu Ser Cys Arg  Asn Asn Pro
    1130                1135                1140

Leu Ile  Ile Pro Val Val His  Asp Leu Ser Gln Pro  Phe Tyr His
    1145                1150                1155

Ser Gln  Ala Val Arg Val Ser  Phe Ser Ser Pro Leu  Val Ala Ile
    1160                1165                1170

Ser Gly  Val Ala Leu Arg Ser  Phe Asp Asn Phe Asp  Pro Val Thr
    1175                1180                1185

Leu Ser  Ser Cys Gln Arg Gly  Glu Thr Tyr Ser Pro  Ala Glu Gln
    1190                1195                1200
```

-continued

```
Ser Cys Val His Phe Ala Cys Glu Lys Thr Asp Cys Pro Glu Leu
    1205                1210                1215

Ala Val Glu Asn Ala Ser Leu Asn Cys Ser Ser Ser Asp Arg Tyr
    1220                1225                1230

His Gly Ala Gln Cys Thr Val Ser Cys Arg Thr Gly Tyr Val Leu
    1235                1240                1245

Gln Ile Arg Arg Asp Asp Glu Leu Ile Lys Ser Gln Thr Gly Pro
    1250                1255                1260

Ser Val Thr Val Thr Cys Thr Glu Gly Lys Trp Asn Lys Gln Val
    1265                1270                1275

Ala Cys Glu Pro Val Asp Cys Ser Ile Pro Asp His His Gln Val
    1280                1285                1290

Tyr Ala Ala Ser Phe Ser Cys Pro Glu Gly Thr Thr Phe Gly Ser
    1295                1300                1305

Gln Cys Ser Phe Gln Cys Arg His Pro Ala Gln Leu Lys Gly Asn
    1310                1315                1320

Asn Ser Leu Leu Thr Cys Met Glu Asp Gly Leu Trp Ser Phe Pro
    1325                1330                1335

Glu Ala Leu Cys Glu Leu Met Cys Leu Ala Pro Pro Pro Val Pro
    1340                1345                1350

Asn Ala Asp Leu Gln Thr Ala Arg Cys Arg Glu Asn Lys His Lys
    1355                1360                1365

Val Gly Ser Phe Cys Lys Tyr Lys Cys Lys Pro Gly Tyr His Val
    1370                1375                1380

Pro Gly Ser Ser Arg Lys Ser Lys Lys Arg Ala Phe Lys Thr Gln
    1385                1390                1395

Cys Thr Gln Asp Gly Ser Trp Gln Glu Gly Ala Cys Val Pro Val
    1400                1405                1410

Thr Cys Asp Pro Pro Pro Lys Phe His Gly Leu Tyr Gln Cys
    1415                1420                1425

Thr Asn Gly Phe Gln Phe Asn Ser Glu Cys Arg Ile Lys Cys Glu
    1430                1435                1440

Asp Ser Asp Ala Ser Gln Gly Leu Gly Ser Asn Val Ile His Cys
    1445                1450                1455

Arg Lys Asp Gly Thr Trp Asn Gly Ser Phe His Val Cys Gln Glu
    1460                1465                1470

Met Gln Gly Gln Cys Ser Val Pro Asn Glu Leu Asn Ser Asn Leu
    1475                1480                1485

Lys Leu Gln Cys Pro Asp Gly Tyr Ala Ile Gly Ser Glu Cys Ala
    1490                1495                1500

Thr Ser Cys Leu Asp His Asn Ser Glu Ser Ile Ile Leu Pro Met
    1505                1510                1515

Asn Val Thr Val Arg Asp Ile Pro His Trp Leu Asn Pro Thr Arg
    1520                1525                1530

Val Glu Arg Val Val Cys Thr Ala Gly Leu Lys Trp Tyr Pro His
    1535                1540                1545

Pro Ala Leu Ile His Cys Val Lys Gly Cys Glu Pro Phe Met Gly
    1550                1555                1560

Asp Asn Tyr Cys Asp Ala Ile Asn Asn Arg Ala Phe Cys Asn Tyr
    1565                1570                1575

Asp Gly Gly Asp Cys Cys Thr Ser Thr Val Lys Thr Lys Lys Val
    1580                1585                1590
```

```
Thr Pro Phe Pro Met Ser Cys Asp Leu Gln Gly Asp Cys Ala Cys
    1595                1600                1605

Arg Asp Pro Gln Ala Gln Glu His Ser Arg Lys Asp Leu Arg Gly
    1610                1615                1620

Tyr Ser His Gly
    1625

<210> SEQ ID NO 4
<211> LENGTH: 1791
<212> TYPE: PRT
<213> ORGANISM: Homo sapiens

<400> SEQUENCE: 4

Met Met Cys Leu Lys Ile Leu Arg Ile Ser Leu Ala Ile Leu Ala Gly
1               5                   10                  15

Trp Ala Leu Cys Ser Ala Asn Ser Glu Leu Gly Trp Thr Arg Lys Lys
            20                  25                  30

Ser Leu Val Glu Arg Glu His Leu Asn Gln Val Leu Leu Glu Gly Glu
        35                  40                  45

Arg Cys Trp Leu Gly Ala Lys Val Arg Pro Arg Ala Ser Pro Gln
    50                  55                  60

His His Leu Phe Gly Val Tyr Pro Ser Arg Ala Gly Asn Tyr Leu Arg
65                  70                  75                  80

Pro Tyr Pro Val Gly Glu Gln Glu Ile His His Thr Gly Arg Ser Lys
                85                  90                  95

Pro Asp Thr Glu Gly Asn Ala Val Ser Leu Val Pro Pro Asp Leu Thr
            100                 105                 110

Glu Asn Pro Ala Gly Leu Arg Gly Ala Val Glu Pro Ala Ala Pro
        115                 120                 125

Trp Val Gly Asp Ser Pro Ile Gly Gln Ser Glu Leu Leu Gly Asp Asp
    130                 135                 140

Asp Ala Tyr Leu Gly Asn Gln Arg Ser Lys Glu Ser Leu Gly Glu Ala
145                 150                 155                 160

Gly Ile Gln Lys Gly Ser Ala Met Ala Ala Thr Thr Thr Thr Ala Ile
                165                 170                 175

Phe Thr Thr Leu Asn Glu Pro Lys Pro Glu Thr Gln Arg Arg Gly Trp
            180                 185                 190

Ala Lys Ser Arg Gln Arg Arg Gln Val Trp Lys Arg Ala Glu Asp
        195                 200                 205

Gly Gln Gly Asp Ser Gly Ile Ser Ser His Phe Gln Pro Trp Pro Lys
    210                 215                 220

His Ser Leu Lys His Arg Val Lys Lys Ser Pro Glu Glu Ser Asn
225                 230                 235                 240

Gln Asn Gly Gly Glu Gly Ser Tyr Arg Glu Ala Glu Thr Phe Asn Ser
                245                 250                 255

Gln Val Gly Leu Pro Ile Leu Tyr Phe Ser Gly Arg Glu Arg Leu
            260                 265                 270

Leu Leu Arg Pro Glu Val Leu Ala Glu Ile Pro Arg Glu Ala Phe Thr
        275                 280                 285

Val Glu Ala Trp Val Lys Pro Glu Gly Gly Gln Asn Asn Pro Ala Ile
    290                 295                 300

Ile Ala Gly Val Phe Asp Asn Cys Ser His Thr Val Ser Asp Lys Gly
305                 310                 315                 320
```

Trp Ala Leu Gly Ile Arg Ser Gly Lys Asp Lys Gly Lys Arg Asp Ala
            325                 330                 335

Arg Phe Phe Phe Ser Leu Cys Thr Asp Arg Val Lys Lys Ala Thr Ile
            340                 345                 350

Leu Ile Ser His Ser Arg Tyr Gln Pro Gly Thr Trp Thr His Val Ala
            355                 360                 365

Ala Thr Tyr Asp Gly Arg His Met Ala Leu Tyr Val Asp Gly Thr Gln
        370                 375                 380

Val Ala Ser Ser Leu Asp Gln Ser Gly Pro Leu Asn Ser Pro Phe Met
385                 390                 395                 400

Ala Ser Cys Arg Ser Leu Leu Leu Gly Gly Asp Ser Ser Glu Asp Gly
            405                 410                 415

His Tyr Phe Arg Gly His Leu Gly Thr Leu Val Phe Trp Ser Thr Ala
            420                 425                 430

Leu Pro Gln Ser His Phe Gln His Ser Ser Gln His Ser Ser Gly Glu
            435                 440                 445

Glu Glu Ala Thr Asp Leu Val Leu Thr Ala Ser Phe Glu Pro Val Asn
        450                 455                 460

Thr Glu Trp Val Pro Phe Arg Asp Glu Lys Tyr Pro Arg Leu Glu Val
465                 470                 475                 480

Leu Gln Gly Phe Glu Pro Glu Pro Glu Ile Leu Ser Pro Leu Gln Pro
            485                 490                 495

Pro Leu Cys Gly Gln Thr Val Cys Asp Asn Val Glu Leu Ile Ser Gln
            500                 505                 510

Tyr Asn Gly Tyr Trp Pro Leu Arg Gly Glu Lys Val Ile Arg Tyr Gln
            515                 520                 525

Val Val Asn Ile Cys Asp Asp Glu Gly Leu Asn Pro Ile Val Ser Glu
530                 535                 540

Glu Gln Ile Arg Leu Gln His Glu Ala Leu Asn Glu Ala Phe Ser Arg
545                 550                 555                 560

Tyr Asn Ile Ser Trp Gln Leu Ser Val His Gln Val His Asn Ser Thr
            565                 570                 575

Leu Arg His Arg Val Val Leu Val Asn Cys Glu Pro Ser Lys Ile Gly
            580                 585                 590

Asn Asp His Cys Asp Pro Glu Cys Glu His Pro Leu Thr Gly Tyr Asp
            595                 600                 605

Gly Gly Asp Cys Arg Leu Gln Gly Arg Cys Tyr Ser Trp Asn Arg Arg
        610                 615                 620

Asp Gly Leu Cys His Val Glu Cys Asn Asn Met Leu Asn Asp Phe Asp
625                 630                 635                 640

Asp Gly Asp Cys Cys Asp Pro Gln Val Ala Asp Val Arg Lys Thr Cys
            645                 650                 655

Phe Asp Pro Asp Ser Pro Lys Arg Ala Tyr Met Ser Val Lys Glu Leu
            660                 665                 670

Lys Glu Ala Leu Gln Leu Asn Ser Thr His Phe Leu Asn Ile Tyr Phe
        675                 680                 685

Ala Ser Ser Val Arg Glu Asp Leu Ala Gly Ala Thr Trp Pro Trp
            690                 695                 700

Asp Lys Asp Ala Val Thr His Leu Gly Gly Ile Val Leu Ser Pro Ala
705                 710                 715                 720

Tyr Tyr Gly Met Pro Gly His Thr Asp Thr Met Ile His Glu Val Gly
            725                 730                 735

-continued

His Val Leu Gly Leu Tyr His Val Phe Lys Gly Val Ser Glu Arg Glu
              740                 745                 750

Ser Cys Asn Asp Pro Cys Lys Glu Thr Val Pro Ser Met Glu Thr Gly
          755                 760                 765

Asp Leu Cys Ala Asp Thr Ala Pro Thr Pro Lys Ser Glu Leu Cys Arg
      770                 775                 780

Glu Pro Glu Pro Thr Ser Asp Thr Cys Gly Phe Thr Arg Phe Pro Gly
785                 790                 795                 800

Ala Pro Phe Thr Asn Tyr Met Ser Tyr Thr Asp Asn Cys Thr Asp
              805                 810                 815

Asn Phe Thr Pro Asn Gln Val Ala Arg Met His Cys Tyr Leu Asp Leu
          820                 825                 830

Val Tyr Gln Gln Trp Thr Glu Ser Arg Lys Pro Thr Pro Ile Pro Ile
      835                 840                 845

Pro Pro Met Val Ile Gly Gln Thr Asn Lys Ser Leu Thr Ile His Trp
850                 855                 860

Leu Pro Pro Ile Ser Gly Val Val Tyr Asp Arg Ala Ser Gly Ser Leu
865                 870                 875                 880

Cys Gly Ala Cys Thr Glu Asp Gly Thr Phe Arg Gln Tyr Val His Thr
              885                 890                 895

Ala Ser Ser Arg Arg Val Cys Asp Ser Ser Gly Tyr Trp Thr Pro Glu
          900                 905                 910

Glu Ala Val Gly Pro Pro Asp Val Asp Gln Pro Cys Glu Pro Ser Leu
      915                 920                 925

Gln Ala Trp Ser Pro Glu Val His Leu Tyr His Met Asn Met Thr Val
930                 935                 940

Pro Cys Pro Thr Glu Gly Cys Ser Leu Glu Leu Phe Gln His Pro
945                 950                 955                 960

Val Gln Ala Asp Thr Leu Thr Leu Trp Val Thr Ser Phe Phe Met Glu
              965                 970                 975

Ser Ser Gln Val Leu Phe Asp Thr Glu Ile Leu Leu Glu Asn Lys Glu
          980                 985                 990

Ser Val His Leu Gly Pro Leu Asp Thr Phe Cys Asp Ile Pro Leu Thr
      995                 1000                1005

Ile Lys Leu His Val Asp Gly Lys Val Ser Gly Val Lys Val Tyr
1010                1015                1020

Thr Phe Asp Glu Arg Ile Glu Ile Asp Ala Ala Leu Leu Thr Ser
      1025                1030                1035

Gln Pro His Ser Pro Leu Cys Ser Gly Cys Arg Pro Val Arg Tyr
      1040                1045                1050

Gln Val Leu Arg Asp Pro Pro Phe Ala Ser Gly Leu Pro Val Val
      1055                1060                1065

Val Thr His Ser His Arg Lys Phe Thr Asp Val Glu Val Thr Pro
      1070                1075                1080

Gly Gln Met Tyr Gln Tyr Gln Val Leu Ala Glu Ala Gly Gly Glu
      1085                1090                1095

Leu Gly Glu Ala Ser Pro Pro Leu Asn His Ile His Gly Ala Pro
      1100                1105                1110

Tyr Cys Gly Asp Gly Lys Val Ser Glu Arg Leu Gly Glu Glu Cys
      1115                1120                1125

Asp Asp Gly Asp Leu Val Ser Gly Asp Gly Cys Ser Lys Val Cys
      1130                1135                1140

```
Glu Leu Glu Glu Gly Phe Asn Cys Val Gly Glu Pro Ser Leu Cys
    1145            1150                1155

Tyr Met Tyr Glu Gly Asp Gly Ile Cys Glu Pro Phe Glu Arg Lys
    1160            1165                1170

Thr Ser Ile Val Asp Cys Gly Ile Tyr Thr Pro Lys Gly Tyr Leu
    1175            1180                1185

Asp Gln Trp Ala Thr Arg Ala Tyr Ser Ser His Glu Asp Lys Lys
    1190            1195                1200

Lys Cys Pro Val Ser Leu Val Thr Gly Glu Pro His Ser Leu Ile
    1205            1210                1215

Cys Thr Ser Tyr His Pro Asp Leu Pro Asn His Arg Pro Leu Thr
    1220            1225                1230

Gly Trp Phe Pro Cys Val Ala Ser Glu Asn Glu Thr Gln Asp Asp
    1235            1240                1245

Arg Ser Glu Gln Pro Glu Gly Ser Leu Lys Lys Glu Asp Glu Val
    1250            1255                1260

Trp Leu Lys Val Cys Phe Asn Arg Pro Gly Glu Ala Arg Ala Ile
    1265            1270                1275

Phe Ile Phe Leu Thr Thr Asp Gly Leu Val Pro Gly Glu His Gln
    1280            1285                1290

Gln Pro Thr Val Thr Leu Tyr Leu Thr Asp Val Arg Gly Ser Asn
    1295            1300                1305

His Ser Leu Gly Thr Tyr Gly Leu Ser Cys Gln His Asn Pro Leu
    1310            1315                1320

Ile Ile Asn Val Thr His His Gln Asn Val Leu Phe His His Thr
    1325            1330                1335

Thr Ser Val Leu Leu Asn Phe Ser Ser Pro Arg Val Gly Ile Ser
    1340            1345                1350

Ala Val Ala Leu Arg Thr Ser Arg Ile Gly Leu Ser Ala Pro
    1355            1360                1365

Ser Asn Cys Ile Ser Glu Asp Glu Gly Gln Asn His Gln Gly Gln
    1370            1375                1380

Ser Cys Ile His Arg Pro Cys Gly Lys Gln Asp Ser Cys Pro Ser
    1385            1390                1395

Leu Leu Leu Asp His Ala Asp Val Val Asn Cys Thr Ser Ile Gly
    1400            1405                1410

Pro Gly Leu Met Lys Cys Ala Ile Thr Cys Gln Arg Gly Phe Ala
    1415            1420                1425

Leu Gln Ala Ser Ser Gly Gln Tyr Ile Arg Pro Met Gln Lys Glu
    1430            1435                1440

Ile Leu Leu Thr Cys Ser Ser Gly His Trp Asp Gln Asn Val Ser
    1445            1450                1455

Cys Leu Pro Val Asp Cys Gly Val Pro Asp Pro Ser Leu Val Asn
    1460            1465                1470

Tyr Ala Asn Phe Ser Cys Ser Glu Gly Thr Lys Phe Leu Lys Arg
    1475            1480                1485

Cys Ser Ile Ser Cys Val Pro Pro Ala Lys Leu Gln Gly Leu Ser
    1490            1495                1500

Pro Trp Leu Thr Cys Leu Glu Asp Gly Leu Trp Ser Leu Pro Glu
    1505            1510                1515

Val Tyr Cys Lys Leu Glu Cys Asp Ala Pro Pro Ile Ile Leu Asn
    1520            1525                1530
```

| | | | | | | | | | | | |
|---|---|---|---|---|---|---|---|---|---|---|---|
| Ala | Asn | Leu | Leu | Leu | Pro | His | Cys | Leu | Gln | Asp | Asn | His | Asp | Val |
| | 1535 | | | | 1540 | | | | 1545 | | |
| Gly | Thr | Ile | Cys | Lys | Tyr | Glu | Cys | Lys | Pro | Gly | Tyr | Tyr | Val | Ala |
| | 1550 | | | | 1555 | | | | 1560 | | |
| Glu | Ser | Ala | Glu | Gly | Lys | Val | Arg | Asn | Lys | Leu | Leu | Lys | Ile | Gln |
| | 1565 | | | | 1570 | | | | 1575 | | |
| Cys | Leu | Glu | Gly | Gly | Ile | Trp | Glu | Gln | Gly | Ser | Cys | Ile | Pro | Val |
| | 1580 | | | | 1585 | | | | 1590 | | |
| Val | Cys | Glu | Pro | Pro | Pro | Val | Phe | Glu | Gly | Met | Tyr | Glu | Cys |
| | 1595 | | | | 1600 | | | | 1605 | | |
| Thr | Asn | Gly | Phe | Ser | Leu | Asp | Ser | Gln | Cys | Val | Leu | Asn | Cys | Asn |
| | 1610 | | | | 1615 | | | | 1620 | | |
| Gln | Glu | Arg | Glu | Lys | Leu | Pro | Ile | Leu | Cys | Thr | Lys | Glu | Gly | Leu |
| | 1625 | | | | 1630 | | | | 1635 | | |
| Trp | Thr | Gln | Glu | Phe | Lys | Leu | Cys | Glu | Asn | Leu | Gln | Gly | Glu | Cys |
| | 1640 | | | | 1645 | | | | 1650 | | |
| Pro | Pro | Pro | Pro | Ser | Glu | Leu | Asn | Ser | Val | Glu | Tyr | Lys | Cys | Glu |
| | 1655 | | | | 1660 | | | | 1665 | | |
| Gln | Gly | Tyr | Gly | Ile | Gly | Ala | Val | Cys | Ser | Pro | Leu | Cys | Val | Ile |
| | 1670 | | | | 1675 | | | | 1680 | | |
| Pro | Pro | Ser | Asp | Pro | Val | Met | Leu | Pro | Glu | Asn | Ile | Thr | Ala | Asp |
| | 1685 | | | | 1690 | | | | 1695 | | |
| Thr | Leu | Glu | His | Trp | Met | Glu | Pro | Val | Lys | Val | Gln | Ser | Ile | Val |
| | 1700 | | | | 1705 | | | | 1710 | | |
| Cys | Thr | Gly | Arg | Arg | Gln | Trp | His | Pro | Asp | Pro | Val | Leu | Val | His |
| | 1715 | | | | 1720 | | | | 1725 | | |
| Cys | Ile | Gln | Ser | Cys | Glu | Pro | Phe | Gln | Ala | Asp | Gly | Trp | Cys | Asp |
| | 1730 | | | | 1735 | | | | 1740 | | |
| Thr | Ile | Asn | Asn | Arg | Ala | Tyr | Cys | His | Tyr | Asp | Gly | Gly | Asp | Cys |
| | 1745 | | | | 1750 | | | | 1755 | | |
| Cys | Ser | Ser | Thr | Leu | Ser | Ser | Lys | Lys | Val | Ile | Pro | Phe | Ala | Ala |
| | 1760 | | | | 1765 | | | | 1770 | | |
| Asp | Cys | Asp | Leu | Asp | Glu | Cys | Thr | Cys | Arg | Asp | Pro | Lys | Ala | Glu |
| | 1775 | | | | 1780 | | | | 1785 | | |
| Glu | Asn | Gln |
| | 1790 | |

<210> SEQ ID NO 5
<211> LENGTH: 744
<212> TYPE: DNA
<213> ORGANISM: Homo sapiens

<400> SEQUENCE: 5

```
atgctccaaa actcagcagt gcttctggtg ctggtgatca gtgcttctgc aacccatgag      60
gcggagcaga atgactctgt gagccccagg aaatcccgag tggcggctca aaactcagct     120
gaagtggttc gttgcctcaa cagtgctcta caggtcggct gcggggcttt tgcatgcctg     180
gaaaactcca cctgtgacac agatgggatg tatgacatct gtaaatcctt cttgtacagc     240
gctgctaaat ttgacactca gggaaaagca ttcgtcaaag agagcttaaa atgcatcgcc     300
aacggggtca cctccaaggt cttcctcgcc attcggaggt gctccacttt ccaaaggatg     360
attgctgagg tgcaggaaga gtgctacagc aagctgaatg tgtgcagcat cgccaagcgg     420
aaccctgaag ccatcactga ggtcgtccag ctgcccaatc acttctccaa cagatactat     480
aacagacttg tccgaagcct gctggaatgt gatgaagaca cagtcagcac aatcagagac     540
```

```
agcctgatgg agaaaattgg gcctaacatg gccagcctct tccacatcct gcagacagac      600
cactgtgccc aaacacaccc acgagctgac ttcaacagga gacgcaccaa tgagccgcag      660
aagctgaaag tcctcctcag gaacctccga ggtgaggagg actctcccct ccacatcaaa      720
cgcacatccc atgagagtgc ataa                                            744
```

<210> SEQ ID NO 6
<211> LENGTH: 909
<212> TYPE: DNA
<213> ORGANISM: Homo sapiens

<400> SEQUENCE: 6

```
atgtgtgccg agcggctggg ccagttcatg accctggctt tggtgttggc cacctttgac       60
ccggcgcggg ggaccgacgc caccaaccca cccgagggtc cccaagacag agctcccag       120 cagaaaggcc gcctgtccct gcagaataca gcggagatcc agcactgttt ggtcaacgct      180
ggcgatgtgg ggtgtggcgt gtttgaatgt ttcgagaaca actcttgtga gattcggggc      240
ttacatggga tttgcatgac ttttctgcac aacgctggaa aatttgatgc ccagggcaag      300
tcattcatca agacgccctt gaaatgtaag gcccacgctc tgcggcacag gttcggctgc      360
ataagccgga agtgcccggc catcagggaa atggtgtccc agttgcagcg ggaatgctac      420
ctcaagcacg acctgtgcgc ggctgcccag gagaacaccc gggtgatagt ggagatgatc      480
catttcaagg acttgctgct gcacgaaccc tacgtggacc tcgtgaactt gctgctgacc      540
tgtggggagg aggtgaagga ggccatcacc cacagcgtgc aggttcagtg tgagcagaac      600
tggggaagcc tgtgctccat cttgagcttc tgcacctcgg ccatccagaa gcctcccacg      660 gcgcccccg agcgccagcc ccaggtggac agaaccaagc tctccagggc ccaccacggg      720
gaagcaggac atcacctccc agagcccagc agtagggaga ctggccgagg tgccaagggt      780
gagcgaggta gcaagagcca cccaaaacgcc catgcccgag gcagagtcgg gggccttggg      840
gctcagggac cttccggaag cagcgagtgg gaagacgaac agtctgagta ttctgatatc      900
cggaggtga                                                             909
```

<210> SEQ ID NO 7
<211> LENGTH: 20
<212> TYPE: DNA
<213> ORGANISM: Mus musculus

<400> SEQUENCE: 7

```
ccgagaggtc aggagagcag                                                   20
```

<210> SEQ ID NO 8
<211> LENGTH: 24
<212> TYPE: DNA
<213> ORGANISM: Mus musculus

<400> SEQUENCE: 8

```
gagcttctct tttagtctgc cccc                                              24
```

<210> SEQ ID NO 9
<211> LENGTH: 33
<212> TYPE: DNA
<213> ORGANISM: Mus musculus

<400> SEQUENCE: 9

```
ccggggtacc atgatgtgtt ggaaggtcct gag                                    33
```

<210> SEQ ID NO 10
<211> LENGTH: 22
<212> TYPE: DNA
<213> ORGANISM: Mus musculus

<400> SEQUENCE: 10
gatggtgagc ggtatgtcac aa                                             22

<210> SEQ ID NO 11
<211> LENGTH: 20
<212> TYPE: DNA
<213> ORGANISM: Mus musculus

<400> SEQUENCE: 11
ccggtccagg cggatacccT                                                20

<210> SEQ ID NO 12
<211> LENGTH: 35
<212> TYPE: DNA
<213> ORGANISM: Mus musculus

<400> SEQUENCE: 12
gatctctaga ttactggttt tcttctgcct tgggg                               35

<210> SEQ ID NO 13
<211> LENGTH: 30
<212> TYPE: DNA
<213> ORGANISM: Homo sapiens

<400> SEQUENCE: 13
gcacaggttc ggcgccataa gccggaagtg                                     30

<210> SEQ ID NO 14
<211> LENGTH: 30
<212> TYPE: DNA
<213> ORGANISM: Homo sapiens

<400> SEQUENCE: 14
cacttccggc ttatggcgcc gaacctgtgc                                     30

<210> SEQ ID NO 15
<211> LENGTH: 36
<212> TYPE: DNA
<213> ORGANISM: Homo sapiens

<400> SEQUENCE: 15
cagcgtgcag gttcaggctg agcagaactg gggaag                              36

<210> SEQ ID NO 16
<211> LENGTH: 36
<212> TYPE: DNA
<213> ORGANISM: Homo sapiens

<400> SEQUENCE: 16
cttccccagt tctgctcagc ctgaacctgc acgctg                              36

<210> SEQ ID NO 17
<211> LENGTH: 34
<212> TYPE: DNA
<213> ORGANISM: Homo sapiens

<400> SEQUENCE: 17
gaactgggga agcctggcct ccatcttgag cttc                                34

<210> SEQ ID NO 18
<211> LENGTH: 34
<212> TYPE: DNA
<213> ORGANISM: Homo sapiens

<400> SEQUENCE: 18
gaagctcaag atggaggcca ggcttcccca gttc                                    34

<210> SEQ ID NO 19
<211> LENGTH: 21
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(21)
<223> OTHER INFORMATION: primer

<400> SEQUENCE: 19
cgcaaatggg cggtaggcgt g                                                  21

<210> SEQ ID NO 20
<211> LENGTH: 36
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(36)
<223> OTHER INFORMATION: primer

<400> SEQUENCE: 20
aaaaaaagat cttcacctcc ggatatcaga atactc                                  36

<210> SEQ ID NO 21
<211> LENGTH: 26
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(26)
<223> OTHER INFORMATION: primer

<400> SEQUENCE: 21
cggaaggaca tatgggaggg caaatc                                             26

<210> SEQ ID NO 22
<211> LENGTH: 26
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(26)
<223> OTHER INFORMATION: primer

<400> SEQUENCE: 22
tgactgggag tagtcaggag aggagg                                             26

PAPPALYSIN REGULATOR

CROSS REFERENCE TO RELATED APPLICATIONS

This application is a continuation of U.S. patent application Ser. No. 14/889,997 filed Nov. 9, 2015, which is a U.S. National Stage under 35 U.S.C. § 371 of International Application No: PCT/DK2014/050131 filed May 12, 2014, and which claims priority to Denmark Patent Application No: PA 2013 70259 filed May 10, 2013, the entire contents of each of which are incorporated herein by reference.

FIELD OF INVENTION

The present invention relates to interaction and complex formation between Pappalysin and stanniocalcin, and the use of stanniocalcin as regulator of Pappalysins.

BACKGROUND OF INVENTION

The pregnancy associated plasma protein-A (PAPP-A) is an important regulator of the insulin-like growth factor (IGF)-system. Through its proteolytic activity, PAPP-A is able to exert activation to the IGF system and thereby regulate key biological processes such as tissue growth and human disease.

PAPP-A is, based on its primary structure, characterized as a metalloproteinase belonging to the metzincin superfamily. However, PAPP-A also has features differing from other metzincins, and therefore it is categorized into a subgroup of metzincins called the pappalysins, which also includes the PAPP-A homologue PAPP-A2.

Pregnancy-associated plasma protein-A (PAPP-A) was first identified as a plasma protein associated with human pregnancy. The protein was of placental origin and was found in serum of pregnant women. The concentration of PAPP-A increases during pregnancy, and reduced levels of PAPP-A in the maternal circulation in the first trimester of pregnancy correlates with high risks of fetal Down's syndrome making PAPP-A a clinical marker for trisomy 21. In addition, low PAPP-A concentrations in maternal pregnancy serum have been associated with high risks of trisomy 18, pre-eclampsia and low birth weight of full-term babies. PAPP-A is the protease responsible for IGF dependent proteolytic activity against IGFBP-4. PAPP-A also specifically cleaves IGFBP-5, and to some extent IGFBP-2. In particular, no other proteinases have been shown to physiologically process IGFBP-4. PAPP-A mediated cleavage of IGFBP-4 is significantly accelerated by the presence of IGF. Cleaved IGFBP fragments have decreased affinity towards IGF and PAPP-A proteolytic activity consequently results in release of bioactive IGF capable of binding and activating the IGF-I receptor. Thus, PAPP-A functions as an IGFBP antagonist.

During pregnancy PAPP-A is secreted from the placenta as a dimer of 400 kDa, but circulates primarily as a disulfide bound 2:2 complex with the proform of eosinophil major basic protein (proMBP) of 500 kDa. This hetero-tetrameric complex denoted PAPP-A/proMBP is found at increasing concentrations during pregnancy. When PAPP-A is complexed to proMBP, its proteolytic activity is abolished. Inhibition by proMBP binding is most likely caused by blockage of the PAPP-A active site or induction of a conformational change in the active site structure. The PAPP-A/proMBP complex is held together by two interchain disulfide bridges between a proMBP subunit and a subunit of the PAPP-A dimer and two additional bridges between the two proMBP subunits.

In addition to proMBP-mediated inhibition, in vitro studies have demonstrated, that PAPP-A activity against IGFBP-4 is inhibited by polyclonal antibodies raised against PAPP-A/proMBP. Furthermore, agents capable of chelating divalent cations, such as EDTA and 1,10-phenantroline, are general unspecific inhibitors of metalloproteinases and thus abolish PAPP-A proteolytic activity as well (Overgaard 2000). Finally, phage derived single chain fragment variable (scFv) antibodies have been shown to inhibit PAPP-A proteolysis of IGFBP-4 through targeting of LNR3, which consequently is considered to be an exosite of PAPP-A. The LNR3 module is located in the C-terminal end of PAPP-A. PAPP-A is a potential target in therapeutical control of IGF signaling, and LNR3 targeting by antibodies demonstrates a way of selectively inhibiting IGFBP-4 proteolysis.

Until now, proMBP is the only known physiological inhibitor of PAPP-A.

SUMMARY OF INVENTION

The present invention relates to aspects of using stanniocalcin as inhibitor of the proteolytic activity of Pappalysin, as well as other aspects of using the interaction between stanniocalcin and Pappalysins.

Pappalysins comprise PAPP-A and PAPP-A2 polypeptides, as well as fragments and variants thereof. Specifically, Pappalysins may form dimers of PAPP-A subunits, PAPP-A2 subunits or fragments or variants thereof, or Pappalysin heterodimers of PAPP-A and PAPP-A2 or fragments or variants thereof.

In one aspect, the present invention relates to a method of decreasing or increasing the activity of a Pappalysin polypeptide by decreasing or increasing the level of interacting Pappalysin and stanniocalcin polypeptides.

In one embodiment, the activity of a Pappalysin polypeptide is increased by administering an agent, which antagonizes the interaction of stanniocalcin with Pappalysin, for example a stanniocalcin directed siRNA or an antibody, such as an antibody capable of antagonizing interaction of a stanniocalcin polypeptide with a Pappalysin polypeptide.

In another embodiment, the activity of Pappalysin polypeptide is inhibited by providing a stanniocalcin polypeptide, for example using a nucleic acid vector expressing said stanniocalcin polypeptide or part thereof, for example using a retroviral vector, or by providing a stanniocalcin polypeptide in the form of purified or partly purified stanniocalcin.

Generally, the activity of Pappalysin polypeptide correlates negatively with the level of stanniocalcin and thus, the activity of Pappalysin polypeptide may be decreased by increasing the level of a stanniocalcin polypeptide, and increased by decreasing the level of a stanniocalcin polypeptide.

In one embodiment, the method is performed by increasing or decreasing the level of stanniocalcin polypeptide in a human cell, such as in a human stem cell. Thus, the method can be applied to increase or decrease the level of a stanniocalcin polypeptide in a mammalian subject, such as in a human being, such as in a specific tissue of a mammalian subject, such as human being, for example a cancer tissue.

In another aspect, a method is provided of preventing, treating or ameliorating a clinical condition in a mammalian subject, such as a human being, said method comprising administering to said mammalian subject, such as human being an effective amount of a stanniocalcin polypeptide. By providing stanniocalcin in an effective amount, the activity of a Pappalysin polypeptide can be inhibited.

This method serves to inhibit a proliferative process, and thus, the method is preferably applied for prevention, treatment or amelioration of a proliferative disorder, such as cancer, for example ovarian cancer, testicular cancer, lung cancer, or any cancer of the digestive system, including ventricular cancer, colon cancer, small bowel cancer and rectal cancer, in particular, the cancer is selected from the group consisting of ovarian cancer, lung cancer and colon cancer. Other preferred clinical conditions include restenosis, atherosclerosis, ovulation, fibrosis, as well as clinical conditions related to human reproduction. Other preferred clinical conditions include fluid accumulation, such as ascites production in ovarian cancer patients.

In a further aspect, the present invention pertains to a method of preventing, treating or ameliorating a clinical condition in a mammalian subject, such as in a human being, said method comprising administering to said mammalian subject, such as human being an effective amount of an agent capable of antagonizing interaction of a stanniocalcin polypeptide with a Pappalysin polypeptide. By providing such an agent, interactions between stanniocalcin and Pappalysin polypeptides are antagonized, and stanniocalcin is prevented from inhibiting Pappalysin. This method can be applied for stimulating a proliferative process, and thus, the method is applicable for clinical conditions such as the treatment of bone fractures by bone remodeling or bone growth, and wounds, where the treatment or amelioration is wound healing.

Interactions between stanniocalcin and Pappalysin polypeptides are preferably antagonized by providing an antibody, such as a blocking antibody, which inhibits the interaction of stanniocalcin with Pappalysin.

In another aspect of the invention, an antibody is provided, which is capable of specifically binding interacting stanniocalcin and Pappalysin polypeptides, such as a non-covalent interaction between PAPP-A and stanniocalcin 1 and/or a covalent complex between PAPP-A and stanniocalcin 2. The antibody preferably has a higher affinity for said complex consisting of or comprising a Pappalysin polypeptide and a stanniocalcin polypeptide than Pappalysin or stanniocalcin individually. This antibody can be used for detection of interacting stanniocalcin and Pappalysin polypeptides. However, the antibody can also be used for stabilizing or promoting the formation of a covalent or non-covalent complex between Pappalysin and stanniocalcin, and thereby serve to inhibit Pappalysin.

In another aspect, an antibody is provided, which is capable of antagonizing the interaction of a stanniocalcin polypeptide with a Pappalysin polypeptide, for example by binding the Pappalysin polypeptide and/or a stanniocalcin polypeptide.

The invention also in one aspect provides an agent or a pharmaceutical composition comprising an agent, which agent is capable of increasing or decreasing the level of a stanniocalcin polypeptide, and/or capable of antagonizing or promoting the interaction of a stanniocalcin polypeptide with a Pappalysin polypeptide for use in medicine. Such agent is for example a stanniocalcin polypeptide or part thereof, an siRNA targeting stanniocalcin or an antibody of the invention. In preferred embodiments, the agent is used in wound healing and/or bone remodeling or bone growth (e.g. in the treatment of bone fractures), and/or the agent is used in the treatment of a restenosis, atherosclerosis, ovulation, fibrosis, or cancer, such as ovarian cancer, testicular cancer, lung cancer, or any cancer of the digestive system, including ventricular cancer, colon cancer, small bowel cancer and rectal cancer.

In another aspect the invention relates to a method of producing a composition comprising Pappalysin polypeptide, wherein said composition is essentially devoid of stanniocalcin polypeptide, said method comprising removing stanniocalcin and/or covalent and non-covalent complexes of Pappalysin and stanniocalcin from a composition comprising Pappalysin and said complexes of Pappalysin and stanniocalcin. This aspect relates to a method of producing a composition comprising Pappalysin polypeptide, wherein said composition is essentially devoid of stanniocalcin polypeptide and complexes comprising stanniocalcin polypeptide, said method comprising the steps of a. providing a composition comprising Pappalysin polypeptide and removing stanniocalcin polypeptide and complexes comprising stanniocalcin polypeptide from said composition, or b. providing a composition comprising Pappalysin polypeptide, which Pappalysin has been expressed in a cell line, wherein said stanniocalcin polypeptide is removed by knock out and/or knock down of one or more stanniocalcin genes.

The invention also relates in a separate aspect to a composition obtainable by the method above.

In another aspect, the present invention relates to a composition comprising Pappalysin, wherein said composition is essentially free of stanniocalcin.

In another aspect, the invention provides a method for quantifying the level of Pappalysin in a sample, said method comprising using a homogenous composition essentially free of stanniocalcin as a standard. In this aspect, a method is provided comprising the steps of a. providing a sample b. providing a reference sample comprising Pappalysin, wherein said reference sample is essentially free of stanniocalcin c. measuring the level of Pappalysin in said sample and said reference sample, d. correlating the level of Pappalysin determined in step c. for the sample with the level in said standard reference sample, and e. based on said correlation, quantifying the level of Pappalysin polypeptide in said sample.

In a further aspect, the invention provides a Pappalysin polypeptide interacting with at least one stanniocalcin polypeptide. The interaction is in one embodiment a non-covalent interaction between PAPP-A and stanniocalcin 1 and/or a covalent interaction between PAPP-A and stanniocalcin 2; and/or a non-covalent interaction between PAPP-A2 and stanniocalcin 1 and/or a covalent interaction between PAPP-A2 and stanniocalcin 2.

In yet another aspect, the present invention relates to a method of producing an antibody specific for interacting Pappalysin and stanniocalcin polypeptides, said method comprising a. providing an animal, such as a mouse b. immunizing said animal with interacting Pappalysin and stanniocalcin polypeptides, and c. obtaining antibody from said animal.

Furthermore, the invention provides in one aspect a method of identifying an agent capable of promoting or antagonizing interaction of a stanniocalcin polypeptide with a Pappalysin polypeptide, said method comprising a. providing a Pappalysin polypeptide and a stanniocalcin polypeptide, b. providing said agent, c. incubating said agent with said Pappalysin and stanniocalcin polypeptides, d. detecting the level of interacting Pappalysin and stanniocalcin polypeptides in the presence and absence of said agent, e. on the basis of the level of interacting Pappalysin and stanniocalcin polypeptides in the presence and absence of said agent detected in step d. determining whether said agent is capable of antagonizing interaction of a stanniocalcin with a Pappalysin.

In a preferred embodiment of this method a. the absence of interacting Pappalysin and stanniocalcin polypeptides is indicative of an agent capable of antagonizing interaction of a stanniocalcin with a Pappalysin, and b. the presence of interacting Pappalysin and stanniocalcin polypeptides is indicative of an agent not capable of antagonizing or an agent promoting the interaction of a stanniocalcin with a Pappalysin.

In another aspect, a method is provided of identifying an agent capable of binding a. interacting Pappalysin and stanniocalcin polypeptides, b. a polypeptide region of a Pappalysin or stanniocalcin polypeptide, which region is not surface exposed in interacting Pappalysin and stanniocalcin polypeptides c. unbound Pappalysin polypeptide (i.e. Pappalysin polypeptide, which does not interact with a stanniocalcin polypeptide, and not binding interacting Pappalysin and stanniocalcin polypeptides d. unbound stanniocalcin polypeptide (i.e. stanniocalcin polypeptide, which does not interact with a Pappalysin polypeptide, and not binding interacting Pappalysin and stanniocalcin polypeptides said method comprising i. providing said agent, ii. contacting said agent with unbound stanniocalcin polypeptide; and/or unbound Pappalysin polypeptide; and/or interacting Pappalysin and stanniocalcin polypeptides, iii. determining whether the agent binds one or more of said unbound stanniocalcin polypeptide; and/or unbound Pappalysin polypeptide; and/or interacting Pappalysin and stanniocalcin polypeptides.

In one embodiment of this method, an agent is identified, which is capable of binding interacting Pappalysin and stanniocalcin polypeptides with higher affinity than Pappalysin or stanniocalcin alone, by a method comprising a. providing said agent, b. contacting said agent with interacting Pappalysin and stanniocalcin polypeptides, c. determining whether the agent binds interacting Pappalysin and stanniocalcin polypeptides, and d. selecting an agent, which binds interacting Pappalysin and stanniocalcin polypeptides.

In another embodiment of this method, an agent is identified, which is capable of binding a polypeptide region of a Pappalysin or stanniocalcin polypeptide, which region is not surface exposed in interacting Pappalysin and stanniocalcin polypeptides, by a method comprising a. providing said agent, b. contacting said agent with interacting Pappalysin and stanniocalcin polypeptides, and/or unbound Pappalysin and stanniocalcin polypeptides, c. determining whether the agent binds interacting Pappalysin and stanniocalcin polypeptides and/or unbound Pappalysin polypeptide and/or stanniocalcin polypeptide, and d. selecting an agent, which does not bind interacting Pappalysin and stanniocalcin polypeptides; where said agent binds unbound Pappalysin polypeptide and/or stanniocalcin polypeptide.

In another embodiment of the method, an agent is identified, which is capable of binding an unbound Pappalysin polypeptide, wherein said agent binds Pappalysin in a region comprising the binding site for stanniocalcin, by a method comprising a. providing said agent, b. contacting said agent with unbound Pappalysin polypeptide, c. determining whether the agent binds Pappalysin polypeptide and interacting Pappalysin and stanniocalcin polypeptides, and d. selecting an agent, which binds Pappalysin polypeptide and does not bind interacting Pappalysin and stanniocalcin polypeptides.

In a third embodiment of the method, an agent is identified, which is capable of binding unbound stanniocalcin polypeptide, wherein said agent binds stanniocalcin in a region comprising the binding site for Pappalysin, by a method comprising a. providing said agent, b. contacting said agent with unbound stanniocalcin polypeptide and interacting Pappalysin and stanniocalcin polypeptides, c. determining whether the agent binds stanniocalcin polypeptide and interacting Pappalysin and stanniocalcin polypeptides, and d. selecting an agent, which binds stanniocalcin polypeptide and does not bind interacting Pappalysin and stanniocalcin polypeptides.

The invention also in one aspect provides a method of detecting an interaction between a Pappalysin polypeptide and a stanniocalcin polypeptide in a sample, said method comprising a. providing said sample, b. providing at least one antibody with affinity for said Pappalysin polypeptide or said stanniocalcin polypeptide or for interacting Pappalysin and stanniocalcin polypeptides, c. exposing said sample to said antibody to form a complex between said antibody and polypeptide, d. removing excess unbound sample, e. exposing interacting antibody-Pappalysin-stanniocalcin polypeptides to a further antibody directed against one of said antibodies, and f. detecting and quantifying the amount of bound antibody of c. and/or e.

Moreover, the invention in one aspect pertains to a method of determining a clinical condition, said method comprising detecting interacting Pappalysin and stanniocalcin polypeptides, such as PAPP-A and stanniocalcin 1 interacting non-covalently and/or a covalent complex between PAPP-A and stanniocalcin 2.

The clinical condition is for example a cancer, such as ovarian cancer, testicular cancer, lung cancer, or any cancer of the digestive system, including ventricular cancer, colon cancer, small bowel cancer and rectal cancer.

In the methods, antibodies, agents, compositions and polypeptides of the invention, a stanniocalcin polypeptide preferably is selected from the group consisting of a. stanniocalcin 1 (SEQ ID NO: 1) and/or stanniocalcin 2 (SEQ ID NO: 2), b. a polypeptide variant having at least 80% identity to any one of SEQ ID NO: 1 and SEQ ID NO: 2, and c. a polypeptide fragment of any polypeptide of a. and b and d. a dimer consisting of two polypeptides individually selected from any polypeptide of a.-c.

e. a monomer, in which at least one cysteine residue responsible for covalent dimerization is mutated to e.g. an alanine residue, consisting of one polypeptides individually selected from any polypeptide of a.-c.

Further, in the methods, antibodies, agents, compositions and polypeptides of the invention, a Pappalysin polypeptide is preferably selected from the group consisting of a. PAPP-A (SEQ ID NO: 3) or PAPP-A2 (SEQ ID NO: 4)
b. a polypeptide variant having at least 80% identity to any one of SEQ ID NO: 3 and SEQ ID NO: 4,
c. a polypeptide fragment of any polypeptide of a. and b.
d. a dimer consisting of two polypeptides individually selected from any polypeptide of a.-c.

DESCRIPTION OF DRAWINGS

FIG. 5: SDS-PAGE of eluted fractions of purified STC1 and STC2. Purified STC1 A) and STC2 B) protein was eluted in 10 fractions. Fractions #1-6 were separated by SDS-PAGE. In addition, a sample of the wash eluate before protein elution and an EDTA sample from the final column stripping were loaded. After electrophoresis gels were stained with coomassie brilliant blue.

FIG. 9: A. Determination of kinetic constants for the STC1:PAPP-A interaction by Surface Plasmon Resonance (SPR). KD=75 pM. B. Surface Plasmon Resonance studies of the interaction between PAPP-A and STC2(C120A).

FIG. 10: A. Determination of inhibition constant (Ki) for the STC1 inhibition of PAPP-A mediated cleavage of IGFBP-4. Ki=68 pM. The One site-Fit (Morrison) Ki model of the GraphPad Prism 5.0 software was used. B. Determination of inhibition constant (Ki) for the mutated STC2 (C120A mutant) inhibition of PAPP-A mediated cleavage of IGFBP-4. Ki=47 nM. The One site-Fit (Morrison) Ki model of the GraphPad Prism 5.0 software was used.

FIG. 16: Sequence alignment of human STC1 and STC2. Sequence alignment of human STC1 (NM_003155.2) and STC2 (NM_003714.2) using Clustal Omega (www.clustal.org/omega/). Disulfide bonds and dimerization disulfide of STC1, indicated by lines, are according to published data16. Cysteine residues of STC2 (C120, C197, and C205), which have no counterpart in STC1, are indicated with blue color.

DETAILED DESCRIPTION OF THE INVENTION

Figure 1:
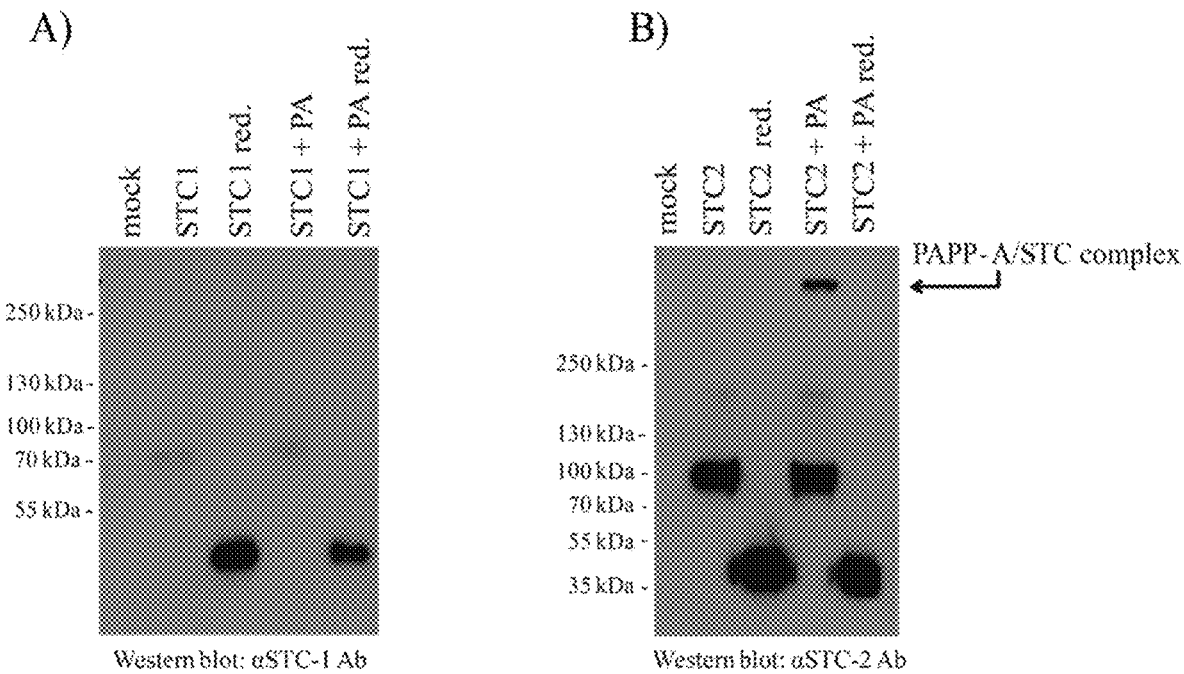
FIG. 1: Western blots detecting STC1 and STC2—Visualization of the covalent PAPP-A/STC2 complex. A) STC1-specific Western blot of culture supernatant from transfected cells. Cells were transfected with either empty plasmid DNA (mock) or co-transfected with STC1 cDNA and empty plasmid DNA or PAPP-A (PA) cDNA. B) STC2-specific Western blot of culture supernatant from transfected cells. Cells were either mock-transfected or co-transfected with STC2 cDNA and empty plasmid DNA or PAPP-A (PA) cDNA. As indicated in the figure, samples were run in SDS-PAGE under non-reducing or reducing (red.) conditions. The localization of the PAPP-A/STC complex is indicated with a black arrow.

The present inventors have identified stanniocalcin polypeptides as inhibitors of pregnancy-associated plasma protein-A (PAPP-A).

The general inventive concept of the present invention relates to a novel complex of Pappalysin and stanniocalcin polypeptides. Thus, the present invention relates to the application of this complex in different methods and products, which involves the complex. Aspects of the invention, relates to the use of the complex between Pappalysins and stanniocalcin polypeptides, as well as methods of producing and screening agents, capable of specifically binding the complex.

The term "interacting Pappalysin and stanniocalcin polypeptides" as used throughout the application text, refers to at least one Pappalysin polypeptide, which interacts with at least one stanniocalcin polypeptide, or at least one stanniocalcin polypeptide, which interacts with at least one Pappalysin polypeptide. Generally, interacting Pappalysin and stanniocalcin polypeptides comprise two Pappalysin polypeptides and two stanniocalcin polypeptides. However, stanniocalcin may be a recombinantly produced monomer in which one or more cysteine residues are mutated to prevent covalent dimerization.

The term "unbound" as used herein in relation Pappalysin and stanniocalcin polypeptides refers to any of said respective polypeptides which does not interact with the other. Thus, the term "unbound Pappalysin polypeptide", refers herein generally to Pappalysin polypeptide, which does not interact with stanniocalcin. Similarly, the term "unbound stanniocalcin polypeptide", refers herein generally to stanniocalcin polypeptide, which does not interact with Pappalysin. In this connection, it is disregarded whether any of Pappalysin and/or stanniocalcin polypeptides may have any other interaction partners.

Pappalysin and Stanniocalcin Polypeptides

The present inventors have surprisingly found that Pappalysin and stanniocalcin polypeptides interact both covalently and non-covalently. Thus, a main aspect of the present invention relates to interacting Pappalysin and stanniocalcin polypeptides.

Pappalysin Polypeptides

Pappalysins are proteolytic enzymes, and include the metalloproteases PAPP-A and PAPP-A2. PAPP-A specifically cleaves IGF-binding proteins, such as IGFBP-4 and IGFBP-5. The cleaved IGFBP fragments have decreased affinity towards IGF and PAPP-A proteolytic activity consequently results in release of bioactive IGF capable of binding and activating the IGF receptor. Activation of the IGF receptor triggers an activation pathway, which leads to e.g. cellular proliferation.

In the context of the present invention, the term "Pappalysin" is meant to include both PAPP-A and PAPP-A2 polypeptides. The term includes Pappalysin polypeptides of any species, and therefore encompasses any mammalian Pappalysin protein; i.e. any polypeptide with homology to the human PAPP-A and human PAPP-A2, which particularly also includes mouse PAPP-A and mouse PAPP-A2. The term "Pappalysin" also encompasses variants and fragments of any PAPP-A and PAPP-A2 polypeptides. The term encompasses both monomeric and multimeric forms of the polypeptides, both homomeric and heteromeric multimers. Specifically, Pappalysins may form homodimers of PAPP-A or PAPP-A2 or fragments or variants thereof, or Pappalysin heterodimers of PAPP-A and PAPP-A2 or fragments or variants thereof.

Specifically, the terms "PAPP-A" and "PAPP-A2" as used herein, is meant to encompass homologous polypeptides of human PAPP-A and PAPP-A2 of any species, respectively, in particular mammalian PAPP-A and PAPP-A2, such as mouse or human PAPP-A and PAPP-A2, with human PAPP-A and PAPP-A2 being most preferred.

In one preferred embodiment of the methods, antibodies, agents, compositions and polypeptides of the present invention, a Pappalysin polypeptide is a human Pappalysin or a fragment or variant thereof; specifically, the Pappalysin polypeptide is selected from the group consisting of a. human PAPP-A (SEQ ID NO: 3) or human PAPP-A2 (SEQ ID NO: 4)

b. a polypeptide variant having at least 70% identity to any one of SEQ ID NO: 3 and SEQ ID NO: 4, c. a polypeptide fragment of any polypeptide of a. and b.

d. a dimer consisting of two polypeptides individually selected from any polypeptide of a.-c.

Thus, in one preferred embodiment, the Pappalysin polypeptide is PAPP-A, such as human PAPP-A, and in another preferred embodiment, the Pappalysin polypeptide is PAPP-A2, such as human PAPP-A2. Variants of Pappalysin polypeptides include variants having at least 60%, such as at least 65%, such as at least 70%, for example at least 75%, for example at least 80, such as at least 85%, 86%, 76%, 88%, 89%, 90%, 91%, 92%, 93%, 94%, 95%, such as at least 96%, 97%, 98%, or 99%, or 99.5% identity to any one of PAPP-A (SEQ ID NO: 3) or PAPP-A2 (SEQ ID NO: 4). In a preferred embodiment, a variant has at least 90% identity, such as at least 95% or at least 98% identity to PAPP-A or PAPP-A2, such as human PAPP-A or PAPP-A2.

Thus, a Pappalysin polypeptide includes the full-length PAPP-A and PAPP-A2 polypeptides and any variants thereof, as well as any fragments of said full-length PAPP-A and PAPP-A2 polypeptides and variants thereof. Fragments of PAPP-A, PAPP-A2 or variants thereof usually comprise or consist of at least 5 consecutive amino acids selected from PAPP-A or PAPP-A2, such as human PAPP-A or PAPP-A2. Fragments may comprise at least 5, such as at least 25, for example at least 50, such as at least 75, for example at least 100, such as at least 200, at least 300, at least 400, at least 500, at least 600, at least 700, at least 800, at least 900, at least 1000, at least 1100, at least 1200, at least 1300, or at least 1400, such as at least 1500 consecutive amino acids selected from PAPP-A, PAPP-A2 or variants thereof.

Furthermore, fragments of the invention may comprise less than 1500, such as less than 1400, less than 1300, less than 1200, less than 1100, less than 1000, less than 900, less than 800, less than 700, less than 600, less than 500, less than 400, less than 300, less than 200, less than 100, less than 75 or less than 50, such as less than 25, such as less than 10 consecutive amino acids selected from PAPP-A, PAPP-A2 or variants thereof.

The preferred length of a Pappalysin fragment of the invention depends on the specific use of the fragment. Pappalysin fragments used for immunization do not necessarily require the full length enzyme. However, methods of detecting a Pappalysin polypeptide in a biological sample, generally aims at detecting biologically native Pappalysins, which are usually full-length.

Preferably, the variants and/or fragments of PAPP-A and PAPP-A2 are functional fragments, in particular metalloproteolytic fragments being able to cleave an IGFBP, such as IGFBP4 and/or IGFBP5.

Stanniocalcin Polypeptides

Stanniocalcins are glycoproteins, which include stanniocalcin 1 (STC1) and stanniocalcin 2 (STC2). Human STC1 and STC2 (hSTC1 and hSTC2) are homodimeric glucoproteins, with subunits of approximately 30-35 kDa and 35-40 kDa, respectively. The mature STC1 protein is 247 amino acids long, while the STC2 protein is longer and consists of 302 amino acids. The N-terminal part of newly synthesized STCs is hydrophobic and functions as a signal peptide for protein secretion. The STCs are conserved among a wide range of eukaryotes.

Blast searches of STC reveal, that the proteins have unique amino acid sequences with no recognizable protein motifs, and it is consequently impossible to predict the biochemical functions of the STCs based on their sequences. Furthermore, the amino acid sequence of STC2 is less than 30% identical to STC1 for a given species. There is, however, some degree of sequence homology between STC1 and STC2, including conservation of glycosylation sites. In addition, all 11 cysteine residues found in STC1 appear to be conserved in STC2. Furthermore, the exon-intron boundaries are conserved between the STCs, suggesting derivation from a common ancestral gene. Ten of the conserved STC cysteine residues form intramolecular disulfide bridges, while the 11th forms an intermolecular disulfide bond linking the subunits of STC homo- or heterodimers. STC2 has a total of 14 cysteine residues, and compared to STC1, human STC2 has an elongated C-terminal containing a histidine cluster (HHxxxxHH), capable of coordinating divalent metal ions.

In the context of the present invention, the term "stanniocalcin" or "STC" is meant to include both stanniocalcin 1 (STC1) and stanniocalcin 2 (STC2) polypeptides. The term includes Stanniocalcin polypeptides of any species, and therefore encompasses any mammalian Stanniocalcin protein; i.e. any stanniocalcin polypeptide with homology to human STC1 and human STC2, which particularly also includes mouse STC1 and mouse STC2. The term "stanniocalcin" or "STC" also encompasses variants and fragments of any STC1 and STC2 polypeptides. The term encompasses both monomeric and multimeric forms of the polypeptides, both homomeric and heteromeric multimers. Specifically, stanniocalcins may form homodimers of STC1 and/or dimers of STC2 or fragments or variants thereof, or stanniocalcin heterodimers of STC1 and STC2 or fragments or variants thereof.

Specifically, the terms "STC1" and "STC2" as used herein, is meant to encompass homologous polypeptides of human STC1 and STC2 of any species, respectively, in particular mammalian STC1 and STC2, such as mouse or human STC1 and STC2, with human STC1 and STC2 being most preferred.

In one preferred embodiment of the methods, antibodies, agents, compositions and polypeptides of the present invention, a stanniocalcin polypeptide is a human stanniocalcin or a fragment or variant thereof; specifically, the stanniocalcin polypeptide of the methods, antibodies, agents, compositions and polypeptides of the present invention is selected from the group consisting of a. human stanniocalcin 1 (SEQ ID NO: 1) and/or human stanniocalcin 2 (SEQ ID NO: 2), b. a polypeptide variant having at least 70% identity to any one of SEQ ID NO: 1 and SEQ ID NO: 2, and c. a polypeptide fragment of any polypeptide of a. and b and d. a dimer consisting of two polypeptides individually selected from any polypeptide of a.-c.

Thus, in one preferred embodiment, the stanniocalcin polypeptide is STC1, and in another preferred embodiment, the stanniocalcin polypeptide is STC2. Variants of stanniocalcin polypeptides include variants having at least 70%, such as at least 75%, for example at least 80, such as at least 85%, 86%, 87%, 88%, 89%, 90%, 91%, 92%, 93%, 94%, 95%, such as at least 96%, 97%, 98%, or 99%, or 99.5% identity to any one of STC1 (SEQ ID NO: 1) or STC2 (SEQ ID NO: 2). In a preferred embodiment, a variant has at least 90% identity, such as at least 95% or at least 98% identity to STC1 or STC2, such as human STC1 or STC2.

Thus, a stanniocalcin polypeptide includes the full-length STC1 and STC2 polypeptides, such as human STC1 or STC2, and any variants thereof, as well as any fragments of said full-length STC1 and STC2 polypeptides and variants thereof. Fragments of STC1, STC2 or variants thereof usually comprise or consist of at least 5 consecutive amino acids selected from STC1 or STC2. Fragments may comprise at least 5, such as at least 15, such as at least 20, such as at least 25, such as at least 30, such as at least 40, such as at least 50, such as at least 60, such as at least 70, such as at least 80, for example at least 90, such as at least 100, such as at least 110, such as at least 120, such as at least 130, such as at least 140, such as at least 150, such as at least 160, such as at least 170, such as at least 180, such as at least 190, such as at least 200 consecutive amino acids selected from STC1, STC2 or variants thereof.

Furthermore, fragments of the invention may comprise less than 200, less than 190, less than 180, less than 170, less than 160, less than 150, less than 140, less than 130, less than 120, less than 110, less than 100, less than 90 or less than 80, such as less than 70, such as less than 60, such as less than 50, such as less than 40, such as less than 30, such as less than 25, such as less than 20, such as less than 15, such as less than 10 consecutive amino acids selected from STC1, STC2 or variants thereof, such as human STC1 or STC2 or variants thereof.

The preferred length of a stanniocalcin fragment of the invention depends on the specific use of the fragment. Pappalysin fragments used for immunization do not necessarily require the full length enzyme. However, methods of detecting a stanniocalcin polypeptide in a biological sample, generally aims at detecting biologically native stanniocalcin, which are usually full-length.

In certain embodiment, the variants and/or fragments of STC1 and STC2 are functional fragments, in particular such variants or fragments which are capable of interacting with a Pappalysin. Specifically, STC1 variants and fragments are preferably capable of interacting non-covalently with PAPP-A, and STC2 variants and fragments are preferably capable of forming covalent complexes with PAPP-A.

In one preferred embodiment, the STC polypeptide is a polypeptide fragment of STC2, which comprise at least C120, i.e. amino acid residue corresponding to cysteine-120.

Pappalysin-Stanniocalcin Interaction

Pappalysin and stanniocalcin polypeptides interact both non-covalently and covalently. In one aspect, the invention relates to a Pappalysin polypeptide interacting with at least one stanniocalcin polypeptide. In one embodiment, the interaction is a non-covalent interaction. However, in another embodiment, the interaction is a covalent complex between a Pappalysin polypeptide and a stanniocalcin polypeptide. In a preferred embodiment, a non-covalent interaction is provided between PAPP-A or PAPP-A2 and stanniocalcin 1, i.e. the invention provides a PAPP-A or a PAPP-A2 polypeptide interacting non-covalently with a STC1 polypeptide. In another preferred embodiment, a covalent complex between PAPP-A or PAPP-A2 and STC2 is provided.

Detection of Interacting Pappalysin and Stanniocalcin Polypeptides

The interaction of stanniocalcin with Pappalysin inhibits the activity of Pappalysin, in particular the proteolytic activity against IGFPBs, such as IGFBP4. Given this regulatory function of stanniocalcin on the activity of Pappalysin, methods for detecting the interacting Pappalysin and stanniocalcin polypeptides are of general interest.

Thus, the invention in one aspect provides a method of detecting an interaction between a Pappalysin polypeptide and a stanniocalcin polypeptide in a sample. Such method may use detecting agents with affinity for Pappalysin polypeptide, stanniocalcin polypeptide and/or for interacting Pappalysin and stanniocalcin polypeptides. Antibodies are specifically suitable agents, as antibodies can be raised with specific activity against specific proteins, while also being easily detectable.

Thus, in one embodiment, the method comprises the steps of a. providing said sample, b. providing at least one antibody with affinity for said Pappalysin polypeptide and/or said stanniocalcin polypeptide and/or for interacting Pappalysin and stanniocalcin polypeptides, c. exposing said sample to said antibody to form a complex between said antibody and polypeptide, d. removing excess unbound sample, and e. exposing interacting antibody-Pappalysin-stanniocalcin polypeptides to a further antibody directed against one of said antibodies, and f. detecting and quantifying the amount of bound antibody of c. and/or e.

Thus, in one embodiment, an antibody is provided which has specific activity for interacting Pappalysin and stanniocalcin polypeptides; i.e. such antibody has no or little affinity for individual Pappalysin and stanniocalcin polypeptides, and has high affinity for interacting Pappalysin and stanniocalcin polypeptides, both non-covalently interacting polypeptides and/or for covalent complexes comprising or consisting of Pappalysin and stanniocalcin polypeptides. Such antibodies are also encompassed by the present invention, as described elsewhere herein, and in a preferred embodiment, such antibodies of the present invention are employed in the detection method of the invention.

In another embodiment, the method for detecting interacting Pappalysin and stanniocalcin polypeptides employs at least two different antibodies, wherein one antibody has affinity for one of the Pappalysin and stanniocalcin polypeptides and another antibody has affinity for the other of said Pappalysin and stanniocalcin polypeptides; e.g. one antibody has affinity for Pappalysin and another antibody has affinity for stanniocalcin or vice versa. The first antibody could be a catching antibody in an ELISA assay, and the second antibody a detection antibody.

Thus, in one embodiment, a detection method is provided, which comprise the steps of
 a. providing said sample,
 b. exposing said sample to a catching antibody with affinity for one of said Pappalysin or stanniocalcin polypeptides allowing said catching antibody to bind said polypeptide,
 c. exposing said sample to a detecting antibody with affinity for the other of said Pappalysin or stanniocalcin polypeptide,
 d. exposing the antibody-Pappalysin-stanniocalcin complex to a further antibody directed against one of said catching or detecting antibodies; and
 e. detecting and quantifying the amount of bound detection antibody and/or further antibody.

In a preferred embodiment, interacting Pappalysin and stanniocalcin polypeptides is a non-covalent interaction between PAPP-A and stanniocalcin 1 and/or a covalent complex between PAPP-A and stanniocalcin 2. In another preferred embodiment, interacting Pappalysin and stanniocalcin polypeptides is a non-covalent interaction between PAPP-A2 and stanniocalcin 1 and/or a covalent complex between PAPP-A2 and stanniocalcin 2.

The choice of the sample depends on the circumstances in which the method is used. If the method is used in diagnosis of a clinical condition, the sample could be a biological sample obtained from a mammalian subject, such as a human being, for example a blood sample or a tissue sample. However, the method may also be used for detecting the amount of interacting Pappalysin and stanniocalcin polypeptides secreted from a cell culture. In this case, the sample can be culture medium of such a cell culture.

The method may also be used for screening for agents capable of modulating (i.e. stimulating or preventing) the formation of covalent and/or non-covalent complex, as described elsewhere herein.

Pappalysin Composition

Pappalysin forms stable and abundant covalent and/or non-covalent interactions with stanniocalcin, and therefore, compositions of Pappalysin generally comprise a certain amount of Pappalysin covalently complexed and/or interacting non-covalently with stanniocalcin. Thus, the level of free Pappalysin in a composition obtained as secreted Pappalysin is generally not known, because an unknown fraction of Pappalysin is bound by stanniocalcin polypeptides. The present invention, therefore in one aspect relates to a composition comprising Pappalysin, wherein said composition is essentially free of stanniocalcin.

In another aspect the invention relates to a method of producing a composition comprising Pappalysin polypeptide, wherein said composition is essentially devoid of stanniocalcin polypeptide, said method comprising removing stanniocalcin from a composition comprising Pappalysin. In one embodiment, the method comprises the steps of
 a. providing a composition comprising Pappalysin polypeptide, and
 b. removing stanniocalcin polypeptide.

Removal of stanniocalcin can include the removal of both free stanniocalcin polypeptide and/or stanniocalcin polypeptide interacting with other polypeptides, in particular stanniocalcin polypeptide interacting with Pappalysin polypeptide. It is preferred that both free stanniocalcins and complexed/interacting stanniocalcins are removed from the composition.

Stanniocalcin may be removed by any methods available to those of skill in the art. In one embodiment, the stanniocalcin polypeptides are removed by affinity chromatography; however other methods are also available and could be applied by those of skill in the art. The invention includes monitoring the separation of PAPP-A and complexes of PAPP-A and stanniocalcin, regardless of the method used for the separation. Said monitoring includes the detection by methods described herein of PAPP-A and complexes of PAPP-A and stanniocalcin. The invention also includes verification of separation by said methods.

In one embodiment, the composition comprising Pappalysin polypeptide is produced by the steps of
 a. culturing a cell line, which express a Pappalysin, for a sufficient amount of time to produce Pappalysin,
 b. collecting the culture medium, and
 b. removing stanniocalcin polypeptide from said culture medium.

The cell line may be selected from any cell line, which expresses Pappalysin, preferably the cell line is a human cell line, such as a human cancer cell line.

Importantly, stanniocalcin polypeptides may also be removed by deletion or disruption of one or more stanniocalcin genes in the cultured cell line. Stanniocalcin may also be removed by knock-down, such as siRNA knockdown, such as knock-down of STC1 and/or STC2; preferably both STC1 and STC2 are knocked-down, deleted or disrupted. Techniques for gene knock-down, disruption and deletion/knockout are well known in the art. Thus, in one embodiment, the present invention provides a method of producing a composition comprising Pappalysin polypeptide, wherein said composition is essentially devoid of stanniocalcin polypeptide, said method comprising
 a. providing a Pappalysin expressing cell line,
 b. deleting or disrupting genes encoding stanniocalcin in said cell line and/or transfecting said cell line with siRNAs targeting STC1 and/or STC2
 c. culturing said cell line for a sufficient amount of time to produce Pappalysin, and
 d. collecting the culture medium.

The invention also relates in a separate aspect to a composition obtainable or obtained by the method of the invention for producing a composition comprising Pappalysin polypeptide, wherein said composition is essentially devoid of stanniocalcin polypeptide, said method being as defined above.

Quantification of Pappalysin

Composition of the invention comprising Pappalysin, which composition is essentially free of stanniocalcin is of specific use in methods for quantifying the level/amount of Pappalysin in a sample. The level of free Pappalysin can only be precisely determined, if a reference material is available with known concentration of Pappalysin, such as PAPP-A and/or PAPP-A2. The composition of the present invention can be used as such a reference or standard material, because this composition is essentially free of stanniocalcin, and therefore, comprise only Pappalysin, which is not bound by stanniocalcin.

Thus, in one aspect, the present invention provides a method for quantifying the level of Pappalysin in a sample, said method comprising using a composition essentially free of stanniocalcin as a standard. The composition is preferably a Pappalysin composition of the present invention, as defined herein above.

The method may comprise the steps of
a. obtaining or providing a sample,
b. providing one or more reference compositions comprising known concentrations of Pappalysin polypeptide, which one or more reference compositions are essentially devoid of stanniocalcin polypeptides,
c. determining the level of Pappalysin polypeptide in said sample and said reference composition, and
d. correlating said level of Pappalysin polypeptide determined for said sample with the level of said one or more reference compositions.

The reference samples may comprise a negative control comprising no Pappalysin, and additional samples comprising any levels of Pappalysin, for example unbound Pappalysin, such as any level of Pappalysin between 0.1 ng/mL and 1000 ng/mL, such as approximately 0.1 ng/mL, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900 and/or 1000 ng/mL Pappalysin.

Regulation of Pappalysin Activity

The present invention broadly relates to the use of stanniocalcin as regulators of Pappalysins. The present inventors have found that stanniocalcin form stable non-covalent interactions and/or covalent complexes with Pappalysins. In particular, it has been found that interaction of stanniocalcins with Pappalysins serves to inhibit the proteolytic activity of Pappalysins. Thus, stanniocalcins function as inhibitors of Pappalysins. This means that the activity of Pappalysins can be regulated via regulation of the interactions between stanniocalcins and Pappalysins. For example, the level of Pappalysin-stanniocalcin interactions can be increased by providing stanniocalcins, thereby promoting formation of Pappalysin-stanniocalcin interactions, and consequently inhibiting the activity of Pappalysin polypeptide.

Alternatively, the level of Pappalysin-stanniocalcin interactions can be decreased by providing an agent, which is capable of antagonizing interactions between Pappalysins and stanniocalcins, thereby increasing the level of unbound Pappalysin (Pappalysins not bound by stanniocalcins), which is catalytically active; i.e. thereby activating Pappalysin polypeptides.

So generally, the activity of Pappalysin polypeptide correlates negatively with the level of stanniocalcin and thus, the activity of Pappalysin polypeptide may be decreased by increasing the level of a stanniocalcin polypeptide, and increased by decreasing the level of a stanniocalcin polypeptide. One embodiment of the present invention therefore relates to a method for decreasing or increasing the activity of a Pappalysin polypeptide, wherein
a. the activity of Pappalysin polypeptide is decreased by increasing the level of a stanniocalcin polypeptide, and
b. the activity of Pappalysin polypeptide increased by decreasing the level of a stanniocalcin polypeptide.

This method is preferably an in vitro method, where the Pappalysin activity is regulated in a sample, for example in a sample comprising a cell culture, such as a cell culture, which expresses one or more Pappalysin polypeptides.

In one embodiment, the method is performed by increasing or decreasing the level of stanniocalcin polypeptide in a human cell, such as in a human stem cell. As mentioned herein above, the stanniocalcin polypeptide may be a stanniocalcin polypeptide derived from any species and thus can be any mammalian stanniocalcin polypeptide. In a preferred embodiment, the stanniocalcin polypeptide is human or mouse STC1 or STC2. The method can be applied to increase or decrease the level of a stanniocalcin polypeptide in a mammalian subject, such as a human being, such as in a specific tissue of a mammalian subject, such as a human being, for example a cancer tissue.

Thus, in one aspect the present invention relates to a method of decreasing or increasing the activity of a Pappalysin polypeptide by decreasing or increasing the level of interacting Pappalysin and stanniocalcin polypeptides.

The level of a stanniocalcin polypeptide can be increased or decreased by providing or administering to the sample an agent capable of decreasing or increasing the level of stanniocalcin polypeptide and/or the level of interacting Pappalysin and stanniocalcin polypeptides is provided to a sample comprising said Pappalysin polypeptide. The choice of agent depends on whether the activity of Pappalysin is intended to be increased or decreased.

In one embodiment, a method is provided for increasing the activity of a Pappalysin polypeptide by decreasing the level of free stanniocalcin polypeptide. In one embodiment, the activity of a Pappalysin polypeptide is increased by administering an agent, which antagonizes the interaction of stanniocalcin with Pappalysin.

Any antagonist, polypeptide, antibody, aptamer, small molecule or any other agent capable of binding stanniocalcin in a manner, which antagonizes its interaction with Pappalysin can be provided or administered in a method of the invention for increasing the activity of Pappalysin. Also any antagonist, polypeptide, antibody, aptamer, small molecule or any other agent capable of binding Pappalysin in a manner, which antagonizes its interaction with stanniocalcin without affecting the activity of Pappalysin, or at least not significantly affecting the activity of Pappalysin, can be provided or administered in the method.

For example, the agent can be a stanniocalcin directed siRNA or an antibody, such as an antibody capable of antagonizing interaction of a stanniocalcin polypeptide with a Pappalysin polypeptide. Specific agents for use in the methods of the invention are described herein below.

In another embodiment, a method is provided for inhibiting the activity of a Pappalysin polypeptide by providing or administering a stanniocalcin polypeptide.

There are many methods available to those of skill in the art to provide a stanniocalcin polypeptide. In biochemical assays, stanniocalcin polypeptide could be provided in a suitable buffered solution, e.g. as a recombinant protein. In cellular systems and if the stanniocalcin polypeptide is administered to a mammalian subject, such as a human being, stanniocalcin can be provided or administered also as stanniocalcin polypeptide in a suitable buffered solution. Alternatively, a delivery system could be used, which involves transgene expression after transfection with a suitable vector, for example a recombinant mammalian expression vector or a viral vector, such as a retroviral vector. Thus, the stanniocalcin polypeptide could be provided using a nucleic acid vector expressing said stanniocalcin polypeptide or part thereof, for example using a retroviral vector.

Therapy

The activity of Pappalysins, in particular PAPP-A has been implicated in a number of clinical conditions, specifically clinical conditions, which involves the regulation of proliferative processes. The present invention provides methods for the prevention, treatment or amelioration of clinical condition, where the treatment involves either activation of Pappalysin, such as PAPP-A or inactivation of Pappalysin, such as PAPP-A. Activation of Pappalysin is relevant for the treatment of clinical condition, where a stimulation of cellular proliferation is desired; such as in bone remodeling or bone growth and/or wound healing. Inactivation or inhibition of Pappalysin is relevant for the treatment of clinical condition, where an inhibition of cellular proliferation is desired; such as in the treatment of cancers.

Thus, in one aspect of the present invention, a method is provided of preventing, treating or ameliorating a clinical condition in a mammalian subject, such as a human being, said method comprising administering to said mammalian subject, such as a human being an effective amount of a stanniocalcin polypeptide. As mentioned herein above, the stanniocalcin polypeptide may be a stanniocalcin polypeptide derived from any species and thus can be any mammalian stanniocalcin polypeptide. In a preferred embodiment, the stanniocalcin polypeptide is human or mouse STC1 or STC2. By providing stanniocalcin in an effective amount, the activity of a Pappalysin polypeptide can be inhibited. The activity of said Pappalysin polypeptide is inhibited by interaction of a Pappalysin polypeptide with at least one stanniocalcin polypeptide, but native stanniocalcin polypeptides generally form dimers, and thus, Pappalysin is often inhibited by interaction with two stanniocalcin dimers. However, stanniocalcin may also be used in the form of stanniocalcin monomers. Stanniocalcin monomers can be produced by recombinant expression of stanniocalcin variants, having a deletion in one or more cysteine residues, thereby preventing formation of disulfide bridges between thiol groups of cysteine residues. In this case, Pappalysin will be inhibited by interaction with stanniocalcin monomers, such as interaction with two stanniocalcin monomers.

In a further aspect, an agent is provided or a pharmaceutical composition comprising such agent, which is capable of promoting interaction of a stanniocalcin polypeptide with a Pappalysin polypeptide for use in medicine. Such an agent could be an antibody capable of binding interacting Pappalysin and stanniocalcin polypeptides, as described elsewhere herein.

This method and use serves to inhibit proliferative processes, and thus, the method is preferably applied for prevention, treatment or amelioration of a proliferative disorder. It is preferred that the proliferative process is associated with Pappalysin expression, or is associated with increased expression of Pappalysin. Methods for determining the level of Pappalysin are described elsewhere herein. It is specifically relevant for proliferative processes and clinical conditions, which are characterized by increased level of Pappalysin. The method is also specifically relevant for proliferative processes and/or proliferative disorders associated with Pappalysin-meditated cleavage of an Insulin-like growth factor-binding protein (IGFBP), in particular such proliferative processes and/or proliferative disorders associated with Pappalysin-meditated cleavage of IGFBP4.

In a preferred embodiment, the clinical condition is a cancer; in particular any cancer type characterized by high level of Pappalysin, preferably characterized by high level of Pappalysin, which is not interacting with stanniocalcin polypeptide.

In another preferred embodiment, the clinical condition is a vascular disease, in particular atherosclerosis or restenosis.

In another preferred embodiment, the clinical condition is a condition of increased fluid accumulation, such as ascites production in ovarian cancer patients.

In one embodiment, the clinical condition is a cancer selected from Acute Lymphoblastic Leukemia, Acute Myeloid Leukemia, Adrenocortical Carcinoma, AIDS-Related Cancers, AIDS-Related Lymphoma, Anal Cancer, Astrocytoma (e.g. Childhood Cerebellar or Childhood Cerebral), Basal Cell Carcinoma, Extrahepatic Bile Duct Cancer, Bladder Cancer, Bone Cancer, Osteosarcoma/Malignant Fibrous Histiocytoma, Brain Stem Glioma, Brain Tumor, Breast Cancer, Male Breast Cancer, Bronchial Adenomas/Carcinoids, Burkitt's Lymphoma, Carcinoid Tumor, Carcinoma of Unknown Primary, Primary Central Nervous System Lymphoma, Cerebral Astrocytoma/Malignant Glioma, Cervical Cancer, Childhood Cancers, Chronic Lymphocytic Leukemia, Chronic Myelogenous Leukemia, Chronic Myeloproliferative Disorders, Colon Cancer, Cutaneous T-Cell Lymphoma, Endometrial Cancer, Ependymoma (such as Childhood Epdndymoma), Esophageal Cancer, Ewing's Family of Tumors, Extracranial Germ Cell Tumor (such as Childhood Extracranial Germ Cell Tumor), Extragonadal Germ Cell Tumor, Eye Cancer (Intraocular Melanoma or Retinoblastoma), Gallbladder Cancer, Gastric (Stomach) Cancer, Gastrointestinal Carcinoid Tumor, Gestational Trophoblastic Tumor, Glioma, Hairy Cell Leukemia, Head and Neck Cancer, Hepatocellular (Liver) Cancer, Hodgkin's Lymphoma, Hypopharyngeal Cancer, Hypothalamic and Visual Pathway Glioma (such as Childhood Hypothalamic and Visual Pathway Glioma), Intraocular Melanoma, Islet Cell Carcinoma (Endocrine Pancreas), Kaposi's Sarcoma, Kidney (Renal Cell) Cancer, Laryngeal Cancer, Lip and Oral Cavity Cancer, Lung Cancer (Non-Small Cell or Small Cell), Lymphoma (such as AIDS-Related Lymphoma, Burkitt's Lymphoma, Cutaneous T-Cell Lymphoma, Non-Hodgkin's Lymphoma), Macroglobulinemia (such as Waldenstrom's Macroglobulinemia), Malignant Fibrous Histiocytoma of Bone/Osteosarcoma, Medulloblastoma (such as Childhood Medulloblastoma), Melanoma, Merkel Cell Carcinoma, Mesothelioma (such as Adult Malignant Mesothelioma or childhood Mesothelioma), Metastatic Squamous Neck Cancer with Occult Primary, Multiple Endocrine Neoplasia Syndrome (such as occurring in childhood), Multiple Myeloma/Plasma Cell Neoplasm, Mycosis Fungoides, Myelodysplastic Syndromes, Myelodysplastic/Myeloproliferative Diseases, Myeloma (such as Multiple Myeloma), Chronic myeloproliferative disorders, Nasal Cavity and Paranasal Sinus Cancer, Nasopharyngeal Cancer, Nasopharyngeal Cancer (such as Childhood Nasopharyngeal Cancer), Neuroblastoma, Oropharyngeal Cancer, Osteosarcoma/Malignant Fibrous Histiocytoma of Bone, Ovarian Cancer (such as Childhood Ovarian Cancer), Ovarian Epithelial Cancer, Ovarian Germ Cell Tumor, Ovarian Low Malignant Potential Tumor, Pancreatic Cancer, Pancreatic Cancer, Paranasal Sinus and Nasal Cavity Cancer, Parathyroid Cancer, Penile Cancer, Pheochromocytoma, Pineoblastoma and Supratentohal Primitive Neuro-ectodermal Tumors, Pituitary Tumor, Pleuropulmonary Blastoma, Prostate Cancer, Renal Pelvis and Ureter Transitional Cell Cancer, Retinoblastoma, Rhabdomyosarcoma (such as Childhood Rhabdomyosarcoma), Salivary Gland Cancer, Adult-onset soft tissue Sarcoma, Soft Tissue Sarcoma (such as Childhood Soft Tissue Sarcoma), uterine Sarcoma, Sezary Syndrome, Skin Cancer (such as non-Melanoma skin cancer), Merkel Cell Skin Carcinoma, Small Intestine Cancer, Supratentorial Primitive Neuroectodermal Tumors (such as occurring in Childhood), Cutaneous T-Cell Lymphoma, Testicular Cancer, Thymoma and Thymic Carcinoma, Thyroid Cancer, Transitional Cell Cancer of the Renal Pelvis and Ureter, Trophoblastic Tumor (such as Gestational Trophoblastic Tumor), Urethral Cancer, Endometrial uterine cancer, Uterine Sarcoma, Vaginal Cancer, Visual Pathway and Hypothalamic Glioma (such as Childhood Visual Pathway and Hypothalamic Glioma), Waldenstrom's Macro-globulinemia or Wilms' Tumor.

In a preferred embodiment, the cancer is selected from the group consisting of ovarian cancer, testicular cancer, lung cancer, or any cancer of the digestive system, including ventricular cancer, colon cancer, small bowel cancer and rectal cancer, in particular, the cancer is selected from the group consisting of ovarian cancer, lung cancer and colon cancer. In one preferred embodiment, the cancer is ovarian cancer. Other preferred clinical conditions include restenosis, atherosclerosis, ovulation, fibrosis, as well as clinical conditions related to human reproduction.

In the methods of preventing, treating or ameliorating a clinical condition in a mammalian subject, such as a human being, said method comprising administering to said mammalian subject, such as a human being an effective amount of a stanniocalcin polypeptide, the stanniocalcin polypeptide can be administered by any suitable method available to those of skill in the art.

In one preferred embodiment, the stanniocalcin polypeptide is administered as stanniocalcin polypeptide in a suitable buffered solution adapted for therapeutic use. Alternatively, a delivery system could be used, which involves transgene expression after transfection with a suitable vector, for example a recombinant mammalian expression vector or a viral vector, such as a retroviral vector. Thus, the stanniocalcin polypeptide could be provided using a nucleic acid vector expressing said stanniocalcin polypeptide or part thereof, for example using a retroviral vector.

Importantly, the present invention also provides methods for treating clinical conditions, where an increase in cellular proliferation is desired. In such methods, Pappalysin is activated by inhibiting interaction between Pappalysins and stanniocalcins. This leads to more unbound Pappalysin, which is proteolytically active against for example IGFBP, such as IGFBP4, which stimulates the IGF-system.

Thus, in one aspect, the present invention pertains to a method of preventing, treating or ameliorating a clinical condition in a mammalian subject, such as a human being, said method comprising administering to said mammalian subject, such as said human being an effective amount of an agent capable of antagonizing interaction of a stanniocalcin polypeptide with a Pappalysin polypeptide. By providing such as agent, interactions between stanniocalcin and Pappalysin polypeptides are antagonized, and stanniocalcin is inhibited from inhibiting Pappalysin. This method can be applied for stimulating a proliferative process, and thus, the method is applicable for clinical conditions such as bone fractures, where the treatment is bone remodeling and/or bone growth, and wounds, where the treatment or amelioration is wound healing. Thus, in a preferred embodiment, the agent capable of decreasing the level of a stanniocalcin polypeptide is used in wound healing and/or bone remodeling or bone growth.

In a further aspect, an agent is provided, or a pharmaceutical composition comprising such agent, which agent is capable of antagonizing the interaction of a stanniocalcin polypeptide with a Pappalysin polypeptide for use in medicine.

Interactions between Pappalysin and stanniocalcin polypeptides can be inhibited by providing any agent capable of antagonizing interaction between Pappalysin and stanniocalcin. Such agent includes for example, any antagonist, polypeptide, antibody, aptamer, small molecule or any other agent capable of binding stanniocalcin in a manner, which antagonizes its interaction with Pappalysin. Also any antagonist, polypeptide, antibody, aptamer, small molecule or any other agent capable of binding Pappalysin in a manner, which antagonizes its interaction with stanniocalcin without affecting the activity of Pappalysin, or at least not significantly affecting the activity of Pappalysin, can be provided or administered in the methods of the invention.

For example, the agent can be a stanniocalcin directed siRNA or an antibody, such as an antibody capable of antagonizing interaction of a stanniocalcin polypeptide with a Pappalysin polypeptide. Specific agents for use in the methods of the invention are described herein below.

In a preferred embodiment, interactions between stanniocalcin and Pappalysin polypeptides are antagonized by providing an antibody, such as a blocking antibody, which inhibits the interaction of stanniocalcin with Pappalysin.

The clinical agents, such as siRNA, antibodies and polypeptides, of the present invention herein may be administered by any suitable method available in the art. The main routes of administration are parenteral injections, oral, and topical, as will be described below. Other drug-administration methods, such as subcutaneous injection, which are effective to deliver the drug to a target site or to introduce the drug into the bloodstream, are also contemplated. Furthermore, intranasal administration and administration by pulmonary inhalation is convenient and effective methods of administration, which could be used.

The clinical agents may be administered orally, for example as an oral tablet. This is a convenient non-invasive approach for administration, which is also preferred by most patients. This administration can be used for agents, which are easily taken up via the gastrointestinal tract.

However, in a more preferred embodiment, the clinical agents may be administered parenterally. This could also be relevant, where the agent is administered in combination with an additional agent, which requires parenteral injection. Thus, in one embodiment of the present invention, the clinical agents provided herein are administered parenterally, that is by intravenous, intramuscular, subcutaneous, intranasal, intrarectal, intravaginal or intraperitoneal administration. The intravenous forms of parenteral administration are generally preferred. Appropriate dosage forms for such administration may be prepared by conventional techniques. The clinical agents may also be administered by inhalation that is by intranasal and oral inhalation administration. In a preferred embodiment, the clinical agents of the present invention are delivered by intravenous, subcutaneous, and/or intra-muscular administration.

Dosages

The dosage requirements will vary with the particular clinical agent employed, the route of administration and the particular individual being treated. Ideally, an individual to be treated by the present method will receive a pharmaceutically effective amount of the clinical agent in the maximum tolerated dose, generally no higher than that required before drug resistance develops.

The methods and uses of the present invention provide that a clinical agent, such as siRNA, antibody or peptide, is administered in an effective amount. By "effective amount" herein is meant a dose that produces the therapeutic effects for which it is administered. The exact dose will depend on the clinical condition or disorder to be treated, and can be ascertained by one skilled in the art using known techniques.

For example, the an antibody or peptide of the present invention can be administered to a person in an amount of from 1 µg/kg to about 100 mg/kg per day. In addition, as is known in the art, adjustments for age as well as the body weight, general health, sex, diet, time of administration, drug interaction, the route and form of administration, and the severity of the clinical condition may be necessary, and will be ascertainable with routine experimentation by those skilled in the art.

An antibody or polypeptide of the invention can be administered in dosage ranges of 5 microgram to about 20 g per day. In one embodiment, suitable dosage ranges of antibody or polypeptide are typically 1-500 mg daily, preferably 1-100 mg daily, 70-200 mg daily, 70-150 mg daily and most preferably 1-30 mg daily, 30-70 mg daily, 40-60 mg daily, 45-55 mg daily or about 50 mg daily. In another embodiment, the suitable dose of antibody or polypeptide is 5-10 mg/kg bodyweight daily, or 10-20 mg/kg bodyweight, or even 20-25 mg/kg bodyweight or 25-30 mg/kg bodyweight or 30-40 mg/kg bodyweight or 40-50 mg/kg bodyweight or 50-60 mg/kg.

The clinical agents, such as siRNA, antibody or polypeptide, as defined elsewhere herein is preferably administered at least once daily, and may therefore be administered once or twice daily. As mentioned elsewhere herein, the doses of clinical agent are preferably administered parenterally, for example by intravenous injection.

Regulatory Agents for Pappalysin Activity

The methods of the invention employ different regulatory agents capable of either increasing or decreasing the activity of Pappalysin by affecting the level of Pappalysin polypeptides, which is interacting with stanniocalcin polypeptides. The agents thus employed in the methods as described elsewhere herein, are defined in the paragraph below. Such agent is for example a stanniocalcin polypeptide or part thereof, an siRNA targeting stanniocalcin or an antibody of the invention.

The invention in a specific aspects relate to such regulatory agents. In one aspect the invention provides an agent capable of increasing or decreasing the level of a stanniocalcin polypeptide.

Agent Capable of Increasing the Level of a Stanniocalcin Polypeptide.

One aspect relates to an agent capable of increasing the level of a stanniocalcin polypeptide. An agent capable of increasing the level of a stanniocalcin polypeptide includes any agent, which serves to increase the expression, stability, resistance to degradation etc. in respect of stanniocalcin. In another aspect, the agent is a stanniocalcin polypeptide, such as STC1, STC2, or a variant or fragment thereof, which is capable of interacting with Pappalysin. In a preferred embodiment, the stanniocalcin polypeptide is STC1 or STC2, such as human STC1 or STC2.

In a preferred embodiment, the agent capable of decreasing the level of a stanniocalcin polypeptide is used in the treatment of a restenosis, atherosclerosis, ovulation, fibrosis, or cancer, such as ovarian cancer, testicular cancer, lung cancer, or any cancer of the digestive system, including ventricular cancer, colon cancer, small bowel cancer and rectal cancer.

Agent Capable of Decreasing the Level of a Stanniocalcin Polypeptide.

In another aspect, the invention relates to an agent capable of decreasing the level of a stanniocalcin polypeptide. Such agent includes any agent, which inhibits expression and/or the stability of stanniocalcin.

In one embodiment, the agent capable of decreasing the level of a stanniocalcin polypeptide is an siRNA targeting stanniocalcin, such as STC1 and/or STC2. Methods of designing siRNA are well-known in the art. In a preferred embodiment, the siRNA comprises or consists of a sequence of at least 5, such as at least 10, for example at least 15, for example at least 20 consecutive nucleotides selected from the STC1 or STC2 genes, such as the human STC1 gene identified by SEQ ID NO: 5 or the human STC2 gene identified by SEQ ID NO: 6. Preferably, the siRNA comprises or consists of a sequence of 5-30, such as 10-25, preferably 18-22 consecutive nucleotides selected from the STC1 or STC2 genes, such as the human STC1 gene identified by SEQ ID NO: 5 or the human STC2 gene identified by SEQ ID NO: 6. However, any interfering nucleic acid species can be used.

Agent Capable of Antagonizing Pappalysin-Stanniocalcin Interaction.

In another aspect, the invention relates to an agent capable of antagonizing the interaction of a stanniocalcin polypeptide with a Pappalysin polypeptide. Such agent includes any agent, which inhibits expression and/or the stability of stanniocalcin.

In a preferred embodiment, the agent capable of decreasing the level of a stanniocalcin polypeptide and/or capable of antagonizing the interaction of a stanniocalcin polypeptide with a Pappalysin polypeptide is used in wound healing and/or bone remodeling or bone growth.

An agent capable of antagonizing the interaction of a stanniocalcin polypeptide with a Pappalysin polypeptide may be selected from any antagonist, polypeptide, antibody, aptamer, small molecule or any other agent capable of binding stanniocalcin polypeptide in a manner, which antagonizes its interaction with Pappalysin. Also any antagonist, polypeptide, antibody, aptamer, small molecule or any other agent capable of binding Pappalysin in a manner, which antagonizes its interaction with stanniocalcin without affecting the activity of Pappalysin, or at least not significantly affecting the activity of Pappalysin polypeptide, is a relevant agent.

In one embodiment, the agent is an antibody, as describes herein below.

Antibodies

In a preferred embodiment, the agent capable of antagonizing the interaction of a stanniocalcin polypeptide with a Pappalysin polypeptide is an antibody directed against a stanniocalcin polypeptide, such as an antibody specifically binding stanniocalcin polypeptide in a manner, which antagonize the interaction of stanniocalcin polypeptide with Pappalysin polypeptide. The antibody is preferably directed against STC1 or STC2, such as human STC1 or STC2. However, also antibodies targeting both STC1 and STC2 are applicable. The present inventors have identified C120 of STC2 to be involved in covalent binding of STC2 with pappalysin. Thus, in a preferred embodiment, an antibody capable of antagonizing the interaction between STC and pappalysin is directed against one or more peptides, which comprise the C120 residue of STC2. For example, an antibody is specific for a fragment of 3-15 amino acids selected from the region between amino acid residues 60 and 180 of STC2, such as a region between amino acid residues 70 and 170 of STC2, such as a region between amino acid residues 80 and 160 of STC2, such as a region between amino acid residues 90 and 150 of STC2, such as a region between amino acid residues 100 and 140 of STC2, such as a region between amino acid residues 110 and 130 of STC2, such as a region between amino acid residues 115 and 130 of STC2, such as a region between amino acid residues 119 and 125 of STC2, The ability of candidate antibodies to specifically target stanniocalcin and antagonize its interaction with Pappalysin polypeptide can be verified by methods of the present invention.

Also antibodies targeting Pappalysin polypeptide can be relevant agents for antagonizing interactions between Pappalysin and stanniocalcin polypeptides. Thus, in another embodiment, the agent capable of antagonizing the interaction of a stanniocalcin polypeptide with a Pappalysin polypeptide is an antibody directed against a Pappalysin polypeptide, which antibody is capable of binding Pappalysin in a manner, which antagonizes its interaction with stanniocalcin without affecting the activity of Pappalysin, or at least not significantly affecting the activity of Pappalysin.

In one aspect of the invention, an antibody is provided, which is capable of specifically binding interacting stanniocalcin and Pappalysin polypeptides. In this aspect, an antibody is provided, which is capable of promoting the interaction of a stanniocalcin polypeptide with a Pappalysin polypeptide, for example by binding the Pappalysin polypeptide and/or a stanniocalcin polypeptide. Pappalysin and stanniocalcin may interact covalently and/or non-covalently. For example, PAPP-A and stanniocalcin 1 interact non-covalently and PAPP-A and stanniocalcin 2 form a covalent complex. Thus, an antibody of the invention is capable of specifically binding interacting stanniocalcin and Pappalysin polypeptides, such as a non-covalent interaction between PAPP-A and stanniocalcin 1 and/or a covalent complex between PAPP-A and stanniocalcin 2. The antibody may simultaneously bind both interacting Pappalysin and stanniocalcin polypeptides; however, alternatively, the antibody may recognize a specific conformation of either Pappalysin or stanniocalcin polypeptide, which conformation is observed, when the polypeptides interact.

Regardless of the exact target of the antibody, it is preferred that the antibody has a higher affinity for interacting Pappalysin and stanniocalcin polypeptides than either of Pappalysin or stanniocalcin individually.

Antibodies of the present invention can be raised by conventional methods by immunization of an animal. Such methods are also within the scope of the invention as is the selection of antibodies which arise from immunization.

In one aspect, the present invention relates to a method of producing an antibody specific for interacting Pappalysin and stanniocalcin polypeptides, said method comprising
 a. providing an animal, such as a mouse
 b. immunizing said animal with interacting Pappalysin and stanniocalcin polypeptides, and
 c. obtaining antibody from said animal.

More, specifically, the antibody can be produced in a method comprising the steps of
 a. providing an animal
 b. providing a interacting Pappalysin and stanniocalcin polypeptides
 c. administering said interacting polypeptide of step b. to said animal
 d. keeping said animal for a sufficient time to produce antibody
 e. obtaining a sample from said animal, and
 f. obtaining antibody from said sample.

The Pappalysin and stanniocalcin polypeptides used for immunization may interact covalently or non-covalently, and in one embodiment, the interaction is a non-covalent interaction between PAPP-A or PAPP-A2 and STC1 and/or a covalent complex between PAPP-A or PAPP-A2 and STC2.

Recombinant Pappalysin and/or STC polypeptides can be used to generate antibodies. Monoclonal antibodies reactive with Pappalysin and/or STC can be produced using standard techniques. Thus, in one embodiment, the present invention relates to a method of producing a monoclonal antibody specific for interacting Pappalysin and stanniocalcin polypeptides, which method comprises the steps of
 a. providing an animal
 b. providing a interacting Pappalysin and stanniocalcin polypeptides
 c. administering said interacting polypeptide of step b. to said animal
 d. keeping said animal for a sufficient time to produce antibody
 e. obtaining a tissue sample from said animal, such as a sample of spleen, and
 f. isolating antibody producing cells of said tissue sample,
 g generation of antibody producing hybridoma cells by fusion of said isolated cells of step f. with a suitable cell line
 h. isolation of hybridoma cells expressing said monoclonal antibody.

Monospecific antibody as used herein is defined as a single antibody species or multiple antibody species with specific binding characteristics for Pappalysin and/or STC. Specific binding as used herein refers to the ability of the antibody species to bind to a specific antigen or epitope, such as those associated with Pappalysin and/or STC, for example binding sites of STC for Pappalysin or binding sites of Pappalysin for STC. Pappalysin and/or STC specific antibodies can generally be raised by immunizing animals such as mice, rats, guinea pigs, rabbits, goats, horses and the like, with rabbits or mice being preferred, with an appropriate concentration of Pappalysin and/or STC antigen either with or without an immune adjuvant. For example, antibodies specific against Pappalysin and/or STC can be used for the purification of native and recombinant Pappalysin and/or STC, as a laboratory reagent, and in antibody based diagnostic kits.

Monoclonal antibodies (mAb) reactive with Pappalysin and/or STC can be prepared by conventional methods, such as by immunizing inbred mice with Pappalysin and/or STC polypeptide/antigen. The mice are immunized with about 0.1 mg to about 10 mg, preferably about 1 mg, of Pappalysin and/or STC polypeptide/antigen in about 0.5 ml buffer or saline incorporated in an equal volume of an acceptable adjuvant. Freund's complete adjuvant is preferred. The mice receive an initial immunization on day 0 and are rested for about 3 to about 30 weeks. Immunized mice may be given one or more booster immunizations of about 0.1 to about 10 mg of Pappalysin and/or STC polypeptide/antigen in a buffer solution such as phosphate buffered saline (PBS) by the intravenous (IV) route. Lymphocytes from antibody-positive mice are obtained by removing spleens from immunized mice by standard procedures known in the art. Hybridoma cells are produced by mixing the splenic lymphocytes with an appropriate fusion partner under conditions which will allow the formation of stable hybridomas. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using Pappalysin and/or STC as the antigen. The culture fluids are also tested in the Ouchterlony precipitation assay to determine the isotype of the mAb. Hybridoma cells from antibody positive wells are then cloned.

In vitro production of anti-Pappalysin or anti-STC is carried out by growing the hybridoma in culture medium to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique.

The "monoclonal antibodies" may also be isolated from phage antibody libraries. Identified phage antibodies can be produced by expression in bacteria.

Methods such as those described above may be used to produce monospecific antibodies specific for Pappalysin and/or STC polypeptide fragments or full-length nascent Pappalysin and/or STC polypeptide.

Pappalysin and/or STC antibody affinity columns can be made by adding the antibodies to a gel support, such as Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing Pappalysin and/or STC or Pappalysin and/or STC fragments are slowly passed through the column. The column is then washed, and the protein is eluted. The purified Pappalysin and/or STC protein is then dialyzed against phosphate buffered saline.

Native Pappalysin and/or STC from sources such as human plasma or serum, tissue extracts, or media from nontransfected cell lines (that endogenously secrete STC) may also be purified by use of an antibody affinity column.

Using polyclonal or monoclonal antibodies against Pappalysin and/or STC a number of assays may be constructed for measurement of Pappalysin and/or STC antigen and in particular interactive Pappalysin and STC polypeptides in body fluids or tissue and cell extracts. Kits based on antibodies may be used for diagnostic purposes. The assays include, but are not limited to, precipitation, passive agglutination, enzyme-linked immunosorbent assay (ELISA) techniques, and radioimmunoassay (RIA) techniques.

For example, using ELISA, a sandwich assay can be constructed where antigen present in an sample is caught by immobilized monoclonal or polyclonal anti(STC). Detection is then performed by the use of one or more monoclonal Pappalysin antibodies and peroxidase conjugated anti(murine IgG). In another assay, antigen present in an sample is caught by immobilized monoclonal or polyclonal anti(Pappalysin), and detected using biotinylated polyclonal anti (STC).

ELISA sandwich assay can also be constructed where any antigen present in sample is caught by immobilized monoclonal antibody. Detection is then performed by the use of a conjugated monoclonal antibody, such as biotinylated antibody. Thus, in another embodiment, interacting Pappalysin and stanniocalcin polypeptides are detected contacting the sample with a monoclonal antibody specifically binding covalent and/or non-covalent complexes of Pappalysin and stanniocalcin, followed by detection by contacting the Pappalysin/stanniocalcin-antibody complex with a conjugated monoclonal antibodies, such as biotinylated antibody.

Assays can be calibrated using purified Pappalysin and/or STC, in particular using a composition comprising a known concentration of unbound Pappalysin or a known concentration of interacting Pappalysin and STC polypeptides. Such calibration may involve constructing a standard curve by serial dilution.

Polyclonal and/or monoclonal antibodies may be used to inhibit the interaction of STC with Pappalysin, in a preferred embodiment, however, monoclonal antibodies are used. Such antibodies are also called blocking antibodies herein. In particular, such antibodies can be used to inhibit a non-covalent interaction between PAPP-A and STC1 and/or formation of a covalent complex comprising or consisting of PAPP-A and STC2, and/or a non-covalent interaction between PAPP-A2 and STC1 and/or formation of a covalent complex comprising or consisting of PAPP-A2 and STC2.

Certain monoclonal antibodies may also be inhibitory towards the interaction of STC with Pappalysin. Such monoclonal antibodies are likely to recognize an epitope in the binding site for Pappalysin, but the inhibitory activity may also be based on binding to neighbouring epitopes. Inhibitory monoclonal antibodies can be obtained by immunization with Pappalysin and/or STC polypeptides or fragments thereof.

The interaction of STC with Pappalysin inhibits Pappalysin meditated cleavage of IGF-BP, such as IGF-BP4, so an antibody capable of inhibiting STC binding to Pappalysin, also serves to activate or promote Pappalysin-mediated cleavage of IGF-BP4, which then leads to activation of IGF receptor. Activation of IGF receptor is known to be involved in cellular proliferation and is also known to be associated with atherosclerotic plaques.

Antibodies, which are inhibitory towards the interaction between Pappalysin and STC have therapeutic value in clinical conditions in which it is be desirable to increase the activity of Pappalysin. Such conditions include for example wound healing and bone remodelling as described herein above.

Method of Determining Clinical Condition

A number of disorders are associated with altered expression of Pappalysin or stanniocalcin, in particular certain cancer forms. Therefore, the invention in one aspect pertains to a method of determining a clinical condition, said method comprising detecting interacting Pappalysin and stanniocalcin polypeptides.

In one embodiment, the method comprises detecting a Pappalysin polypeptide, which interacts with a stanniocalcin polypeptide. However, in another embodiment, a stanniocalcin polypeptide is detected, which interacts with a Pappalysin polypeptide.

Any specific Pappalysin/stanniocalcin interaction may be detected in the diagnostic method. The interaction may include both non-covalent interactions and covalent complexes. In one embodiment, the interaction is a non-covalent interaction between PAPP-A and STC1 and/or STC2. In another embodiment, the interaction is a non-covalent interaction between PAPP-A2 and STC1 and/or STC2. In a further embodiment, the interaction is a covalent complex between PAPP-A and STC1 and/or STC2; and in yet another embodiment, the interaction is a covalent complex between PAPP-A2 and STC1 and/or STC2. In a preferred embodiment, the interaction is a non-covalent interaction between PAPP-A and stanniocalcin 1. In another embodiment, the interaction is a covalent complex between PAPP-A and stanniocalcin 2.

The diagnostic method may be used for the determination of any relevant clinical condition; in particular such conditions, which are associated with Pappalysin and/or stanniocalcin.

In one embodiment, the clinical condition is a cancer. In one embodiment, the clinical condition is a cancer selected from Acute Lymphoblastic Leukemia, Acute Myeloid Leukemia, Adrenocortical Carcinoma, AIDS-Related Cancers, AIDS-Related Lymphoma, Anal Cancer, Astrocytoma (e.g. Childhood Cerebellar or Childhood Cerebral), Basal Cell Carcinoma, Extrahepatic Bile Duct Cancer, Bladder Cancer, Bone Cancer, Osteosarcoma/Malignant Fibrous Histiocytoma, Brain Stem Glioma, Brain Tumor, Breast Cancer, Male Breast Cancer, Bronchial Adenomas/Carcinoids, Burkitt's Lymphoma, Carcinoid Tumor, Carcinoma of Unknown Primary, Primary Central Nervous System Lymphoma, Cerebral Astrocytoma/Malignant Glioma, Cervical Cancer, Childhood Cancers, Chronic Lymphocytic Leukemia, Chronic Myelogenous Leukemia, Chronic Myeloproliferative Disorders, Colon Cancer, Cutaneous T-Cell Lymphoma, Endometrial Cancer, Ependymoma (such as Childhood Epdndymoma), Esophageal Cancer, Ewing's Family of Tumors, Extracranial Germ Cell Tumor (such as Childhood Extracranial Germ Cell Tumor), Extragonadal Germ Cell Tumor, Eye Cancer (Intraocular Melanoma or Retinoblastoma), Gallbladder Cancer, Gastric (Stomach) Cancer, Gastrointestinal Carcinoid Tumor, Gestational Trophoblastic Tumor, Glioma, Hairy Cell Leukemia, Head and Neck Cancer, Hepatocellular (Liver) Cancer, Hodgkin's Lymphoma, Hypopharyngeal Cancer, Hypothalamic and Visual Pathway Glioma (such as Childhood Hypothalamic and Visual Pathway Glioma), Intraocular Melanoma, Islet Cell Carcinoma (Endocrine Pancreas), Kaposi's Sarcoma, Kidney (Renal Cell) Cancer, Laryngeal Cancer, Lip and Oral Cavity Cancer, Lung Cancer (Non-Small Cell or Small Cell), Lymphoma (such as AIDS-Related Lymphoma, Burkitt's Lymphoma, Cutaneous T-Cell Lymphoma, Non-Hodgkin's Lymphoma), Macroglobulinemia (such as Waldenstrom's Macroglobulinemia), Malignant Fibrous Histiocytoma of Bone/Osteosarcoma, Medulloblastoma (such as Childhood Medulloblastoma), Melanoma, Merkel Cell Carcinoma, Mesothelioma (such as Adult Malignant Mesothelioma or childhood Mesothelioma), Metastatic Squamous Neck Cancer with Occult Primary, Multiple Endocrine Neoplasia Syndrome (such as occurring in childhood), Multiple Myeloma/Plasma Cell Neoplasm, Mycosis Fungoides, Myelodysplastic Syndromes, Myelodysplastic/Myeloproliferative Diseases, Myeloma (such as Multiple Myeloma), Chronic myeloproliferative disorders, Nasal Cavity and Paranasal Sinus Cancer, Nasopharyngeal Cancer, Nasopharyngeal Cancer (such as Childhood Nasopharyngeal Cancer), Neuroblastoma, Oropharyngeal Cancer, Osteosarcoma/Malignant Fibrous Histiocytoma of Bone, Ovarian Cancer (such as Childhood Ovarian Cancer), Ovarian Epithelial Cancer, Ovarian Germ Cell Tumor, Ovarian Low Malignant Potential Tumor, Pancreatic Cancer, Pancreatic Cancer, Paranasal Sinus and Nasal Cavity Cancer, Parathyroid Cancer, Penile Cancer, Pheochromocytoma, Pineoblastoma and Supratentohal Primitive Neuro-ectodermal Tumors, Pituitary Tumor, Pleuropulmonary Blastoma, Prostate Cancer, Renal Pelvis and Ureter Transitional Cell Cancer, Retinoblastoma, Rhabdomyosarcoma (such as Childhood Rhabdomyosarcoma), Salivary Gland Cancer, Adult-onset soft tissue Sarcoma, Soft Tissue Sarcoma (such as Childhood Soft Tissue Sarcoma), uterine Sarcoma, Sezary Syndrome, Skin Cancer (such as non-Melanoma skin cancer), Merkel Cell Skin Carcinoma, Small Intestine Cancer, Supratentorial Primitive Neuroectodermal Tumors (such as occurring in Childhood), Cutaneous T-Cell Lymphoma, Testicular Cancer, Thymoma and Thymic Carcinoma, Thyroid Cancer, Transitional Cell Cancer of the Renal Pelvis and Ureter, Trophoblastic Tumor (such as Gestational Trophoblastic Tumor), Urethral Cancer, Endometrial uterine cancer, Uterine Sarcoma, Vaginal Cancer, Visual Pathway and Hypothalamic Glioma (such as Childhood Visual Pathway and Hypothalamic Glioma), Waldenstrom's Macro-globulinemia or Wilms' Tumor.

In a preferred embodiment, the cancer is selected from the group consisting of ovarian cancer, testicular cancer, lung cancer, or any cancer of the digestive system, including ventricular cancer, colon cancer, small bowel cancer and rectal cancer, in particular, the cancer is selected from the group consisting of ovarian cancer, lung cancer and colon cancer. In one preferred embodiment, the cancer is ovarian cancer. Other preferred clinical conditions include restenosis, atherosclerosis, ovulation, fibrosis, as well as clinical conditions related to human reproduction.

In the diagnostic method of the invention, the interacting Pappalysin and stanniocalcin polypeptides may be detected using any suitable method, in particular any method of the present invention, as defined elsewhere herein. In one embodiment, interaction between Pappalysin and stanniocalcin is detected using at least one antibody. The interaction is preferably detected using two different antibodies in a solid phase immunoassay, such as ELISA. For example, the interaction may be detected using a Pappalysin-specific antibody and/or a stanniocalcin-specific antibody. For example a Pappalysin-specific antibody can be used as a catching antibody and then a stanniocalcin-specific antibody can be used as detecting antibody. Naturally, the function of the antibodies can be reciprocated, and a stanniocalcin-specific antibody can be used as a catching antibody and a Pappalysin-specific antibody as detecting antibody.

Screening Method

A main aspect of the present invention relates to interacting Pappalysin and stanniocalcin polypeptides. Such interacting polypeptides are of use in a number of different applications, which are also within the scope of the present invention. Therefore, certain aspects of the present invention relates to the use of Pappalysin/stanniocalcin interactions or complexes in methods for identifying specific agents, which can be used in the detection and/or regulation of interacting Pappalysin and stanniocalcin polypeptides; in particular in detection and/or regulation of a non-covalent interaction between PAPP-A and stanniocalcin 1 and/or a covalent complex between PAPP-A and stanniocalcin 2.

Potential detecting agents or regulating/modulating agents of interacting Pappalysin and stanniocalcin polypeptides may include any relevant agent, such as any agent with therapeutic potential. In one embodiment, the agent is an antibody, such as an antibody directed against an epitope of a Pappalysin or stanniocalcin polypeptide or part thereof.

Antagonizing Agent

In one aspect, a method is provided of identifying an agent capable of antagonizing interaction of a stanniocalcin polypeptide with a Pappalysin polypeptide.

The term "antagonizing" as used herein in relation to the interaction between stanniocalcin and Pappalysin generally refers to the ability of the agent to inhibit interaction between Pappalysin and stanniocalcin.

The method of the invention comprises the steps of
a. providing a Pappalysin polypeptide and a stanniocalcin polypeptide,
b. providing said agent,
c. incubating said agent with said Pappalysin and stanniocalcin polypeptides,
d. detecting the presence or absence of interacting Pappalysin and stanniocalcin polypeptides,
e. on the basis of the presence or absence of interacting Pappalysin and stanniocalcin polypeptides detected in step d. determining whether said agent is capable of antagonizing interaction of a stanniocalcin with a Pappalysin.

In a preferred embodiment of this method
a. the absence of interacting Pappalysin and stanniocalcin polypeptides is indicative of an agent capable of antagonizing interaction of a stanniocalcin with a Pappalysin, and
b. the presence of interacting Pappalysin and stanniocalcin polypeptides is indicative of an agent not capable of antagonizing interaction of a stanniocalcin with a Pappalysin.

For example a collection of Pappalysin directed agents, such as anti-Pappalysin antibodies, can be screened for the ability to bind Pappalysin in a manner, which antagonize the interaction of Pappalysin with stanniocalcin. Alternatively, a collection of stanniocalcin directed agents, such as anti-stanniocalcin antibodies can be screened for the ability to bind stanniocalcin in a manner, which antagonize the interaction of stanniocalcin with Pappalysin.

Specific Binding Agent

In another aspect, a method is provided of identifying an agent capable of binding
a. interacting Pappalysin and stanniocalcin polypeptides,
b. a polypeptide region of a Pappalysin or stanniocalcin polypeptide, which region is not surface exposed in interacting Pappalysin and stanniocalcin polypeptides
c. a Pappalysin polypeptide, which do not interact with a stanniocalcin polypeptide,
d. a stanniocalcin polypeptide, which do not interact with a Pappalysin polypeptide,
said method comprising
i. providing said agent,
ii. contacting said agent with stanniocalcin polypeptide, which do not interact with Pappalysin; and/or Pappalysin polypeptide, which do not interact with stanniocalcin; and/or interacting Pappalysin and stanniocalcin polypeptides,
iii. determining whether the agent binds one or more of said stanniocalcin polypeptide, which do not interact with Pappalysin; and/or Pappalysin polypeptide, which do not interact with stanniocalcin; and/or interacting Pappalysin and stanniocalcin polypeptides.

In one embodiment of this method, an agent is identified, which is capable of binding interacting Pappalysin and stanniocalcin polypeptides, by a method comprising
a. providing said agent,
b. contacting said agent with interacting Pappalysin and stanniocalcin polypeptides,
c. determining whether the agent binds interacting Pappalysin and stanniocalcin polypeptides, and
d. selecting an agent, which binds interacting Pappalysin and stanniocalcin polypeptides.

In another embodiment of this method, an agent is identified, which is capable of binding a polypeptide region of a Pappalysin or stanniocalcin polypeptide, which region is not surface exposed in interacting Pappalysin and stanniocalcin polypeptides, by a method comprising
a. providing said agent,
b. contacting said agent with interacting Pappalysin and stanniocalcin polypeptides, and/or unbound Pappalysin and stanniocalcin polypeptides,
c. determining whether the agent binds interacting Pappalysin and stanniocalcin polypeptides and/or unbound Pappalysin polypeptide and/or stanniocalcin polypeptide, and
d. selecting an agent, which does not bind interacting Pappalysin and stanniocalcin polypeptides; where said agent binds unbound Pappalysin polypeptide and/or stanniocalcin polypeptide.

In another embodiment of the method, an agent is identified, which is capable of binding a unbound Pappalysin polypeptide (i.e. Pappalysin, which do not interact with a stanniocalcin polypeptide), wherein said agent binds Pappalysin in a region comprising the binding site for stanniocalcin, by a method comprising
a. providing said agent,
b. contacting said agent with unbound Pappalysin polypeptide,
c. determining whether the agent binds unbound Pappalysin polypeptide and does not bind interacting Pappalysin and stanniocalcin polypeptides, and
d. selecting an agent, which binds unbound Pappalysin polypeptide and does not bind interacting Pappalysin and stanniocalcin polypeptides In another embodiment of the method, an agent is identified, which is capable of binding unbound stanniocalcin polypeptide (i.e. stanniocalcin, which do not interact with a Pappalysin polypeptide), by a method comprising
a. providing said agent,
b. contacting said agent with unbound stanniocalcin polypeptide and interacting Pappalysin and stanniocalcin polypeptides,
c. determining whether the agent binds stanniocalcin polypeptide and interacting Pappalysin and stanniocalcin polypeptides, and
d. selecting an agent, which binds stanniocalcin polypeptide and does not bind interacting Pappalysin and stanniocalcin polypeptides.

For example, pools of agents, such as antibodies, specifically binding either Pappalysin and/or stanniocalcin can be screened for their ability to selectively bind interacting Pappalysin/stanniocalcin polypeptides, without binding non-interacting Pappalysin or stanniocalcin polypeptides

EXAMPLES

Example 1

Materials and Methods

The experimental procedures used to achieve the presented results are described in this section.

Cell Cultures and Transfection

All cells were cultured at 37° C. in 5% $CO_2$. Human embryonic kidney 293T (HEK293T) cells (DuBridge 1987) were maintained in high-glucose Dulbecco's modified eagles medium (DMEM) supplemented with 10% fetal bovine serum, 2 mM glutamine, nonessential amino acids, and gentamicin (10% SEM).

For transient transfection, $2.5*10^6$ cells were plated onto 6 cm culture dishes or $6.3*10^6$ cells were plated onto 10 cm culture dishes and transfected 20 hours later (at a cell confluence of 60-70%) by calcium phosphate co-precipitation using 10 or 20 µg plasmid DNA, respectively, prepared by GenElute HP Plasmid Miniprep Kit (SIGMA) or Plasmid Giga Kit (QIAGEN) eluted in 2 mM Tris, pH 7.4. Transfected cells were maintained in 10% SEM or serum free medium (SFM). Harvested culture medium was cleared by centrifugation (3 min, 3200 rpm), and the culture supernatant was saved.

Plasmid cDNA Constructs Used for Transfection

Human wt PAPP-A cDNA: pcDNA3.1-huPAPP-A encoding the CD11 signal peptide and residues 1-1547 of the mature PAPP-A polypeptide was described in (Overgaard 2000).

Empty plasmid: pcDNA3.1+(Invitrogen)

Angiotensinogen (AGT) cDNA: pcDNA3.1-AGT

PAPP-A variants: Constructs containing cDNA encoding PAPP-A variants were described previously; PAPP-A-E483Q (Boldt 2001), PAPP-AdLNR1, PAPP-AdLNR2, PAPP-AdLNR1-2, PAPP-A-356A, PAPP-A389A (Weyer 2007), PAPP-A/PAPP-A2 chimeras (E. Gaidamauskus, C. Oxvig, unpublished), zfPAPP-A (Kjær-Sørensen 2009, unpublished), muPAPP-A (Soe 2002)

Human STC1 cDNA: pcDNA3.1-STC1 encoding C-terminally myc-his-tagged human STC1 (made by J. Mikkelsen, C. Oxvig, unpublished)

Human STC2 cDNA: pcDNA3.1-STC2 encoding C-terminally myc-his-tagged human STC2 (made by J. Mikkelsen, C. Oxvig, unpublished)

proMBP cDNA: pcDNA3.1-proMBP was made previously (Overgaard 2004).

SDS-PAGE

Samples were non-reduced or reduced by the addition of dithiothreitol (DTT). Samples were afterwards added to Laemmli loading buffer and heated for two minutes at 100° C. before loading on 5-15%, 10-20%, or 12% Tris-glycine gels. The gels were run for 40-60 minutes at 30 mA in Laemmli buffer in Sodium Dodecyl Sulfate-Polyacrylamide Gel Electrophoresis. Proteins were visualized by Coomassie Brilliant Blue staining or Western blotting. Radiolabeled proteins were visualized by autoradiography using a Typhoon Phosphorimager.

Western Blotting (WB)

After separation by SDS-PAGE, samples were transferred onto a polyvinylidene difluoride (PVDF) membrane (Millipore) by electroblotting at 500 mA and 200V for 1.5-2 hours in ethanol blotting buffer (20% ethanol, 0.2 M glycine, 25 mM Tris, 0.1% SDS, pH 8.8). The membrane was blocked in TST (50 mM Tris, 0.5 M NaCl, 0.1% Tween-20, pH 9.0) containing 2% Tween for 10 minutes and incubated with primary antibodies diluted in 2% M-TST (2% skimmed milk powder diluted in TST) overnight (ON). Secondary horse radish peroxidase (HRP)-conjugated antibodies were also diluted in 2% M-TST and incubated with the membrane for one hour before development, using ECL plus (GE Healthcare). Images were captured on X-ray films. Between all incubation steps the membranes were thoroughly washed in TST. All steps were carried out at room temperature. Used antibodies are listed below in section 7.1.9 and 7.1.10.

Formation of the PAPP-A/STC Complexes

For co-expression of recombinant PAPP-A and STC1 or STC2, 293T cells were co-transfected with 5 µg PAPP-A and 5 µg empty plasmid DNA (for comparison), 5 µg STC1 or 5 µg STC2 cDNA. For co-expression of PAPP-A, STC1 and STC2 cells were co-transfected with 5 µg PAPP-A, 2.5 µg STC1 and 2.5 µg STC2 cDNA. Compared cells were always transfected with equal amounts of DNA. To visualize formed complexes, the culture supernatants were afterwards analyzed by Western blotting using polyclonal antibodies detecting PAPP-A/proMBP (effectively polyclonal PAPP-A antibodies) or polyclonal antibodies detecting human STC1 or STC2.

For formation of the PAPP-A/STC complex after separate protein synthesis, culture supernatants containing recombinant PAPP-A or PAPP-A-E389Q and STC1 or STC2 were mixed in a 1:1 volume. When purified PAPP-A/proMBP complex was studied, purified protein was first mixed with medium from mock-transfected cells (to obtain a 10 µg/mL concentration of PAPP-A/proMBP), and then mixed with STC2-medium, 1:1. Mixtures were incubated at 37° C. ON or samples were taken out at defined timepoints and frozen to stop complex formation. To visualize formed complexes, the mixtures were analyzed by the complex specific ELISA or Western blotting using polyclonal antibodies detecting PAPP-A/proMBP or polyclonal antibodies detecting STC1 or STC2.

Purification of Recombinant STC Proteins 293T cells were transiently transfected with STC1 or STC2 cDNA (20 ug plasmid DNA per 10 cm plate) by calcium phosphate co-precipitation as explained in section 7.1.1. 48 hours post-transfection, 10% SEM was changed to serum-free medium (SFM), which was harvested and replaced two days later by fresh SFM, which was harvested after an additional two days.

SFM containing recombinant human STC1 or STC2 was mixed 1:1 with binding buffer (20 mM imidazole, 50 mM $NaH_2PO_4$, 1 M NaCl, 0.05% Tween-20, pH 7.5) and sterile filtrated before loading onto affinity columns. Columns were packed with Chelating Sepharose Fast Flow affinity media (GE Healthcare), which was charged with $Ni^{2+}$ by addition of 2% $NiSO_4$ in $H_2O$ and equilibrated in binding buffer. Sample solutions were added to the columns at a flow rate of 1 mL/minute ON. Columns were afterwards washed with binding buffer, and proteins were eluted in 10 fractions of 250 µL elution buffer (50 mM $NaH_2PO_4$, 300 mM imidazole, pH 7.5).

Mass Spectrometry

Purified STC1 and STC2 protein samples were separated by SDS-PAGE and visualized by Coomassie Brilliant Blue staining. Visible bands were cut out and prepared for mass spectrometry. Thus, gel plugs were first dehydrated, using a Speedvac for 15 minutes, and then reduced with 20 mM DTT in 100 mM NH4HCO3 for 10 minutes. Samples were afterwards alkylated with iodoacetamide (IAN) in 100 mM NH4HCO3 for 10 minutes, and digested with 12.5 ng/µL trypsin in 50 mM NH4HCO3 on ice for 45 minutes. Between all steps, samples were dehydrated and washed with 50% or 100% acetonitrile (ACN). Trypsin buffer was discarded, and 50 mM NH4HCO3 digestion buffer was added to the samples and incubated at 37° C. for two hours. Finally, 100% ACN was added to the samples, which were analysed by MALDI-TOF mass spectrometry on a Voyager DE-PRO (Applied Biosystems). Using a monoclonal antibody, PAPP-A was immuno-precipitated from conditioned medium from a human cancer cell line. Proteins were separated by SDS-PAGE on a 3-8% gradient gel and visualized by Coomassie Brilliant Blue staining. Coomassie stained protein bands were excised, trypsinized and subject to MALDI-TOF peptide mass fingerprinting.

PAPP-A Proteolytic Assay

PAPP-A was pre-incubated with mock-, STC1- or STC2-medium in a 1:1 volume at 37° C. ON. PAPP-A samples (200× diluted) were incubated at 37° C. with purified, $^{125}$I-labeled IGFBP-4 (pre-incubated with IGF-II, 50 nM, 0.35 µg/mL) or IGFBP-5 (10 nM, 0.30 µg/mL) in 50 mM Tris, 100 mM sodium chloride, 1 mM calcium chloride, pH 7.5. Samples of the reaction mixtures were taken out at defined time points from 0 to 180 min and reactions were stopped by the addition of 20 mM EDTA in sample buffer.

Proteolytic activity was monitored by separating the samples by non-reducing SDS-PAGE (10-20% Tris-glycine Laemmli gels). Band intensities of cleaved and intact IGFBP-4 or -5 were measured with a Typhoon PhosphorImager. After subtraction of background, % cleaved IGFBP-4 or -5 was calculated as cleaved/total*100% IGFBP, and plotted as a function of time.

Surface Plasmon Resonance (Biacore)

All SPR analysis was carried out on a Biacore T200 instrument (GE Healthcare). In short, 5000 RU of a PAPP-A monoclonal antibody was immobilized on a CM5 chip by standard amine coupling. Remaining active groups were blocked with ethanolamine. Recombinant PAPP-A in conditioned HEK293 medium was captured to a level of 200 RU. A dilution series of Purified STC1 or STC2 was injected over the surface. Following each round of binding the chip surface was regenerated by injection of a low pH buffer. If possible data were fit with the standard 1:1 Langmuir model.

Inhibition of Enzymatic Activity

In short, 20 pM PAPP-A was mixed with a dilution series of known concentrations of recombinantly expressed and purified STC1 or STC2 (C120A) and allowed to incubate for 1 hour. The enzymatic reaction was started by the addition of 10 nM 1-125 labeled IGFBP-4 together with 100 nM IGF-II. Samples were taken out at different time points, and separated by SDS-PAGE. Degree of cleavage was determined by densitometry using phosphor-imaging. Relative initial velocities (expressed as % activity) for each STC concentration were estimated and points were plotted in a graph. Estimation of the inhibition constant, Ki, was done using the One site Fit (Morrison) Ki model of the GraphPad Prism 5.0 software.

Results

Expression of STC Protein and Analysis of the PAPP-A/STC Complex

To enable the examination of STC1 and STC2, the expression of recombinant protein was done. Expression plasmids with inserts of cDNA encoding recombinant human STC1 and STC2 were constructed, and the expression of STC1 and STC2 was verified in cells transfected with these constructs. Furthermore, we examined the possible formation of a protein complex between PAPP-A and either STC1 or STC2 by co-transfecting 293T cells with PAPP-A and STC1 or STC2 cDNA. Subsequent to transfection, SDS-PAGE of culture supernatants was performed under reducing or non-reducing conditions, and STC-specific Western blots were made (FIG. 1). The possibility of cross-reactivity of STC1-specific antibodies (αSTC1 Abs) and STC2-specific antibodies (αSTC2 Abs) against STC2 and STC1, respectively, was excluded by Western blotting (not shown).

The presence of STC1 and STC2 in the conditioned media was detected both under reducing and non-reducing conditions. Under non-reducing conditions, STC1 was detected in a faint band of ~70 kDa, representing the covalently linked STC1 dimer (FIG. 1A). Loading a larger amount of sample, lead to a much more distinct band. Under reducing conditions, one STC1 band of ~35 kDa appeared, corresponding to the STC1 monomer. The STC2 monomer also appeared under reducing conditions, and was represented by a distinct band of ~45 kDa (FIG. 1B). Under non-reducing conditions, STC2 protein was primarily represented by bands of ~100 kDa, but bands of higher molecular weights of ~200 kDa as well as ~150 kDa and >250 kDa were also detectable. These bands probably represented multimers of STC2 protein. In general, the STC-detecting antibodies seemed to recognize reduced STC better than non-reduced protein.

Figure 2:
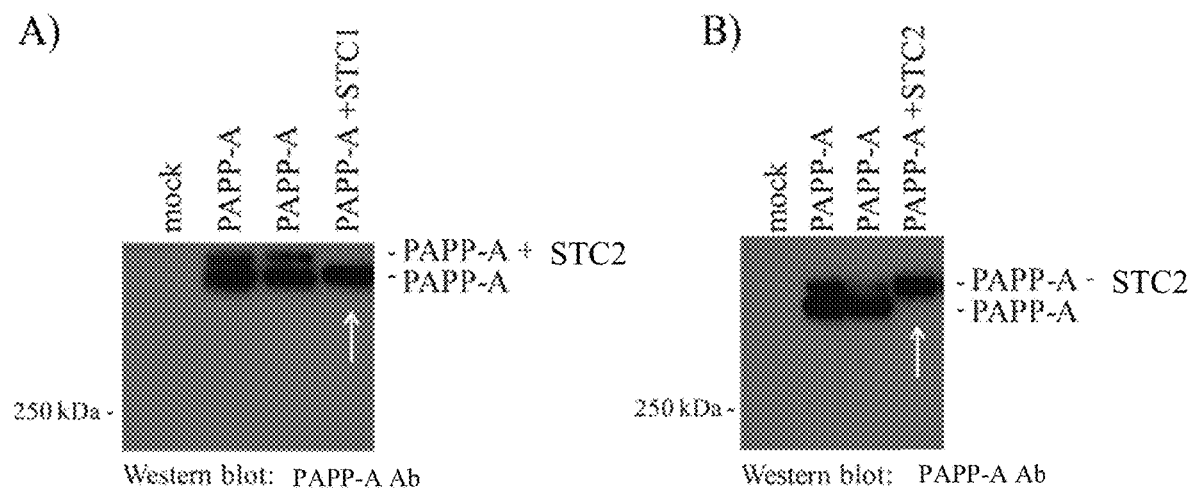
FIG. 2: Western blots detecting PAPP-A during co-expression with STC1 or STC2. Samples were culture supernatant from transfected cells. Cells were transfected with empty plasmid DNA (mock) or co-transfected with PAPP-A and empty plasmid DNA, STC1 (A), or STC2 (B) cDNA. PAPP-A Antibodies (Ab) were used for PAPP-A detection. White arrows in A) and B) point out the disappearance of high molecular weight (HMW) and low molecular weight (LMW) PAPP-A bands, respectively. The localizations of PAPP-A and PAPP-A in complex with STC2 are depicted. These results are representative of at least three independent experiments. Cells which are not transfected with STC1 or STC2 cDNA show some level of endogenous STC2, which cause a fraction of PAPP-A to migrate slower.

As shown in FIG. 1A, co-transfection with STC1 and PAPP-A cDNA did not result in any additional bands in the STC1 Western blots. However, when 293T cells were co-transfected with STC2 and PAPP-A cDNA, a HMW band of >>250 kDa appeared in the STC2 Western blot (FIG. 1B, indicated with black arrow). This band disappeared upon reduction, indicating that the formation of this protein complex was dependent on disulfide linkage. Corresponding Western blots detecting PAPP-A were made (FIG. 2).

When STC1 and PAPP-A were co-expressed in 293T cells, only the PAPP-A band of low molecular weight (LMW) was detected in PAPP-A-Western blots (FIG. 2A, white arrow). On the contrary, during co-expression of STC2 and PAPP-A, only the HMW PAPP-A band was observed (FIG. 2B, white arrow).

Combining these findings, the co-expression of PAPP-A and STC seemed to influence the pattern of complex formation between these proteins. The co-expression of PAPP-A and STC2 resulted in the appearance of the reducible HMW band in the STC2 Western blot (FIG. 1B, black arrow), suggesting that a HMW disulfide bound complex between PAPP-A and STC2 was secreted into the cell culture medium. This complex probably gave rise to the HMW bands observed in the PAPP-A blots. Thus, as indicated by the STC2 blot, cells over-expressing PAPP-A and STC2 synthesize a molar excess of STC2, causing all PAPP-A to be complexed to STC2. The HMW PAPP-A bands in Western blots of PAPP-A samples thus likely represent a complex between recombinant PAPP-A and endogenous STC2.

No corresponding complex between STC1 and PAPP-A was detected in STC1 Western blots, suggesting that a potential STC1/PAPP-A complex would be non-covalent. The disappearance of HMW PAPP-A bands upon PAPP-A and STC1 co-expression can thus be explained by the formation of a non-covalent PAPP-A/STC1 complex, which was not detected by Western blotting, because of the denaturing conditions in SDS-PAGE. In support thereof, recombinant STC1 protein seemed to outcompete endogenous STC2 in complex formation with PAPP-A, explaining the appearance of only the LMW PAPP-A band (FIG. 2A, white arrow). Furthermore, the co-expression of PAPP-A, STC1, and STC2 in cells gave rise to a high molecular STC1 band in Western blots, probably representing an STC1/STC2 heterodimer complexed to PAPP-A. Thus, the HMW bands observed in PAPP-A Western blots could also represent complex formation between PAPP-A and the STC1/STC2 heterodimer.

Since complex formation initially was only detectable in Western blotting for PAPP-A/STC2 and not for the potential non-covalent PAPP-A/STC1 complex, it was examined if the complexes could be detected in an enzyme-linked immunosorbent assay (ELISA). The PAPP-A/STC2 complex was readily detectable in ELISA.

Figure 3:
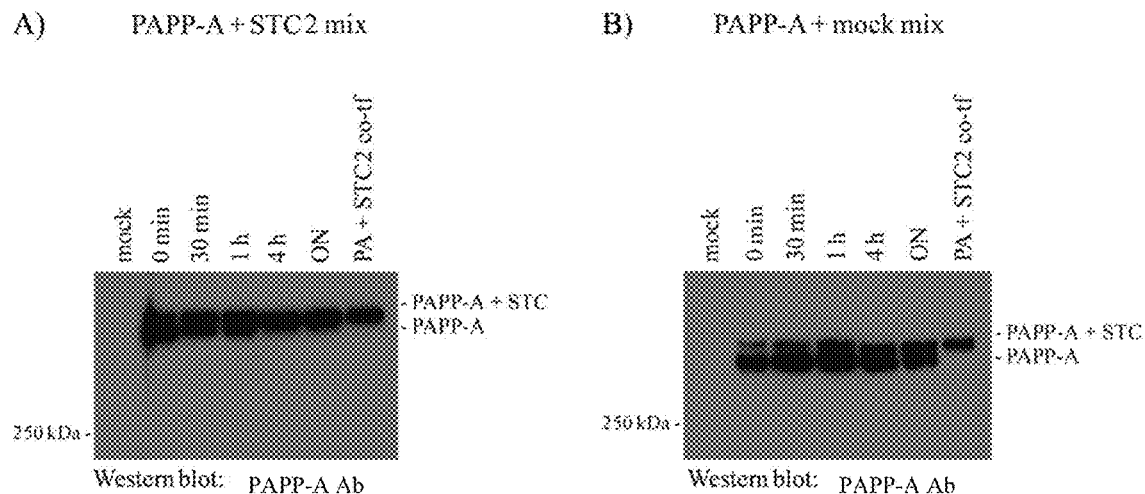
FIG. 3: Detection of PAPP-A/STC2 complex formation. Mixtures of PAPP-A and STC2 (A) or PAPP-A and mock (B) medium taken out at the indicated time points were analyzed by Western blotting. Conditioned medium from mock transfected cells or cells co-transfected with PAPP-A and STC2 cDNA (PA+STC2 co-tf) were loaded as controls. PAPP-A antibodies were used for PAPP-A detection. The localization of PAPP-A and PAPP-A in complex with STC2 is depicted. ON indicates overnight incubation. It is evident from B that a non-saturating level of endogenous stanniocalcin 2 is present in the medium.

Monitoration of PAPP-A/STC Complex Formation proMBP is a well-known inhibitor of PAPP-A. Formation of the PAPP-A/proMBP complex has previously been shown to occur outside of cells when culture supernatants containing separately synthesized recombinant proMBP and PAPP-A were mixed. In a similar experiment, it was examined if the formation of the PAPP-A/STC2 complex was possible in the absence of cells. 293T cells were transfected with empty plasmid DNA (mock), PAPP-A or STC2 cDNA. Culture supernatant from the PAPP-A-transfected cells was mixed in a 1:1 volume with either STC2- or mock-medium and incubated at 37° C. Samples were taken out at defined time points. After incubation, PAPP-A Western blots were made to examine the appearance of HMW PAPP-A bands (FIG. 3).

At the beginning of incubation, both HMW and LMW PAPP-A bands were detected by Western blotting of PAPP-A/STC2 mixtures, as seen previously (FIG. 3A). With time, the LMW bands became increasingly faint, and after four hours of incubation, PAPP-A was exclusively detected as a HMW complex. These PAPP-A bands were comparable to the HMW band observed upon co-transfection with PAPP-A and STC2 cDNA, suggesting that a PAPP-A/STC2 complex had formed during incubation. The time-dependent appearance of corresponding STC2 bands of high molecular weight was verified in STC2 Western blots (not shown). Interestingly, a similar complex formation in mixtures of PAPP-A and mock medium was also observable (FIG. 3B). When PAPP-A and mock medium were mixed, an increasing fraction of PAPP-A was found in the HMW-complex over time. However, after ~1 hour of incubation, the fraction of HMW-PAPP-A remained constant. This indicated, that endogenous STC2 protein in the mock medium or residual endogenous STC2 in the PAPP-A medium formed a complex with PAPP-A during incubation, until the endogenous STC2 was used up.

In combination, the data show, that a complex comprising or consisting of recombinant PAPP-A and STC2 can be formed upon co-transfection and by mixing of separately synthesized PAPP-A and STC2 protein. Furthermore, it is likely, that the HMW bands of PAPP-A observed in Western blotting of PAPP-A samples represent complexes of PAPP-A and endogenous STC2. Even though a covalent complex between PAPP-A and STC1 could not be detected, the existence of a non-covalent PAPP-A/STC1 complex is also likely. The existence of such a complex was supported by Western blots detecting only a LMW band of PAPP-A when cells were co-transfected with PAPP-A and STC1 and by the ELISA detecting the PAPP-A/STC1 complex, although not convincingly. Furthermore, immunoprecipitation experiments shows co-immunoprecipitation of PAPP-A and STC1.

Endogenous STC Presence in PAPP-A Samples

Figure 4:
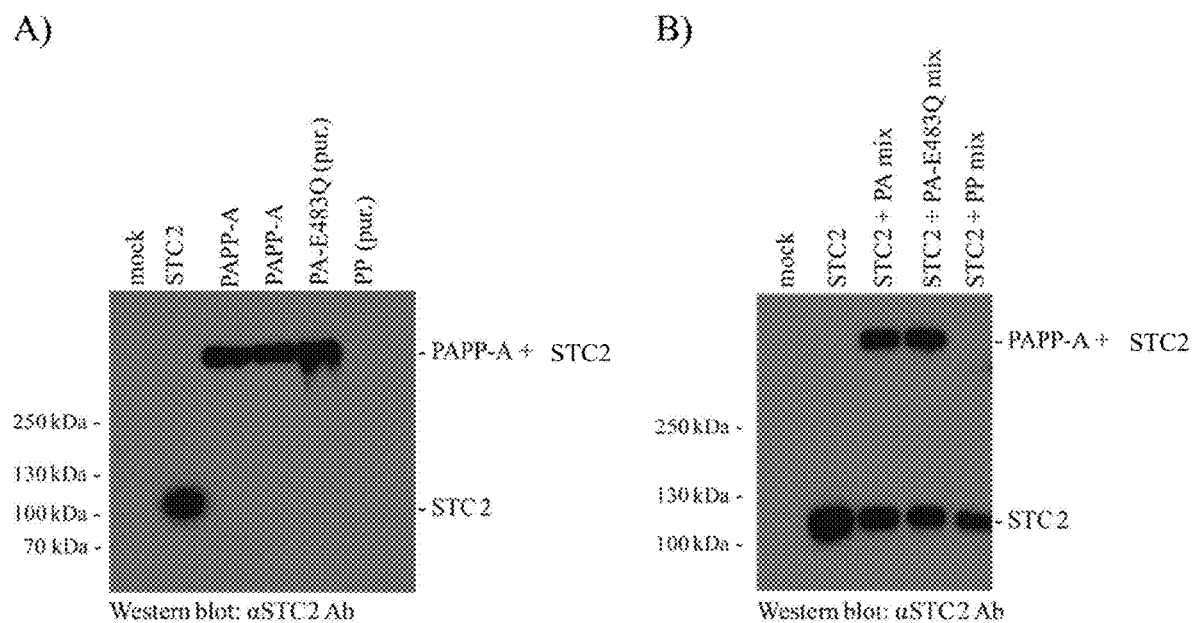
FIG. 4: Detection of STC2 protein in PAPP-A samples. A) Mock-medium, recombinant PAPP-A in culture supernatant (PAPP-A), purified (pur.) PAPP-A-E483Q, and purified PAPP-A/proMBP (PP) samples were examined in Western blotting, using αSTC2 antibodies. B) Culture supernatant containing recombinant STC2 was mixed with PAPP-A in culture supernatant (STC2+PA mix), PA-E483Q in culture supernatant (STC2+PA-E483Q mix), or purified PP diluted in mock-medium (STC2+PP mix) and examined in Western blotting, using αSTC2 antibodies. The localization of STC2 and STC2 in complex with PAPP-A is depicted.

Since a notable fraction of PAPP-A was complexed to endogenous STC2 and STC1 during recombinant PAPP-A expression, several PAPP-A samples were examined for the presence of STC2. Culture supernatants from cells transfected with empty plasmid DNA or PAPP-A cDNA were tested, as well as samples of purified PAPP-A-E483Q and purified PAPP-A/proMBP complex (FIG. 4A). Furthermore, by mixing these samples with medium containing recombinant STC2, it was evaluated if a PAPP-A/STC2 complex could be formed (FIG. 4B).

As shown in FIG. 4A, STC2 was detected in medium containing recombinant PAPP-A and in a sample of purified PAPP-A-E483Q. In both cases, STC2 was detected in the HMW-complex, suggesting that it was complexed to PAPP-A. STC2 was, however, not detected in a sample of purified PAPP-A/proMBP complex. These results demonstrate that a fraction of the recombinant PAPP-A protein expressed by 293T cells was complexed to endogenous STC2. The binding of proMBP, however, probably excluded the simultaneous binding of STC2.

When the PAPP-A samples were mixed and incubated with recombinant STC2 in culture supernatant, formed PAPP-A/STC2 complex was detected in Western blotting as well (FIG. 4B). The sample containing purified PAPP-A/proMBP complex (PP mix), however, did not form an STC2 complex.

Purification of STC1 and STC2 Protein

The application of purified protein in several experimental procedures can be valuable. STC1 and STC2 protein was therefore purified from serum-free medium of 293T cells transfected with STC1 or STC2 cDNA, respectively. By exploiting the myc-his-tag inserted in the C-terminal, the STC proteins were purified by immobilized $Ni^{2+}$ affinity chromatography. Purified STC1 and STC2 protein was visualized in coomassie brilliant blue stained SDS-PAGE of eluted protein fractions (FIG. 5).

Purified protein was visible in fractions #2-6. As in the STC1 Western blots, purified STC1 migrated primarily in a band of ~70 kDa (FIG. 5A). Furthermore, as expected from the STC2 Western blots, purified STC2 migrated in bands of multiple sizes, the primary one being of ~100 kDa (FIG. 5B). The appearance of HMW STC2 bands of >170 kDa could indicate formation of STC2-multimers or complex formation with unidentified proteins. Thus, since several bands were observed, especially for STC2, the identity of proteins in bands appearing under reducing and non-reducing conditions was investigated. STC1 bands of ~35-40 kDa and ~70 kDa and STC2 bands of ~40 kDa, ~100 kDa, and >170 kDa, obtained from reducing and non-reducing SDS-PAGE, were analyzed by mass spectrometry. In all bands of purified STC1 examined, no other proteins than STC1 were identified. Moreover, only STC2 protein was identified in bands of purified STC2. This indicated that at the current conditions, the STCs did not form complexes to any proteins endogenously expressed by the 293T cells.

The STCs Affect PAPP-A Proteolytic Activity

Figure 6:
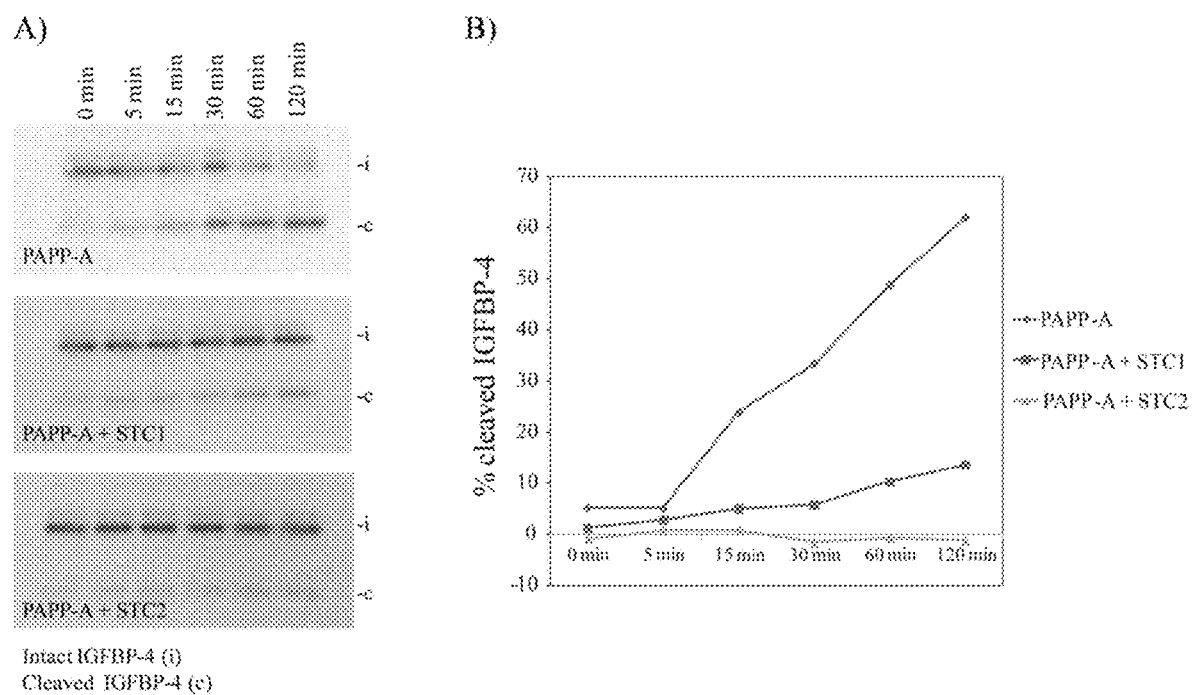
FIG. 6: Inhibition of PAPP-A proteolytic activity against IGFBP-4 by STC1 and STC2. PAPP-A in culture supernatant was pre-incubated with mock-, STC1- or STC2-medium ON, and 125I-labeled IGFBP-4 was pre-incubated with IGF-II for 15 minutes at 37° C. A) Samples were separated by SDS-PAGE. To monitor PAPP-A proteolytic activity against IGFBP-4, the amount of intact (i) and cleaved (c) 125I-IGFBP-4 at time points from 0-120 min was measured. The positions of intact and cleaved IGFBP-4 are indicated for PAPP-A samples with absence (upper gel) or presence of STC1 (middle gel) or STC2 (lower gel). B) The percentage of proteolytically cleaved IGFBP-4 was calculated and depicted as a function of time. These results are representative of at least three independent experiments.
Figure 7:
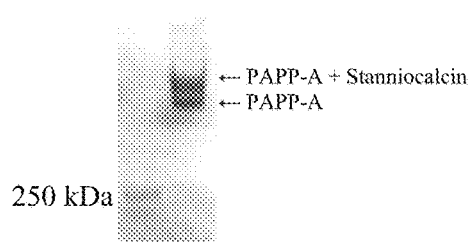
FIG. 7: Identification of PAPP-A interaction partner by MALDI-TOF mass spectrometry. Total PAPP-A was immunoprecipitated from the medium of a human cancer cell line using a monoclonal PAPP-A antibody. The precipitated material appeared as two bands in non-reducing SDS-PAGE. In the lower band of 400 kDa, only peptides derived from PAPP-A were identified. Apart from PAPP-A, the upper band also contained Stanniocalcin peptides.
Figure 8:
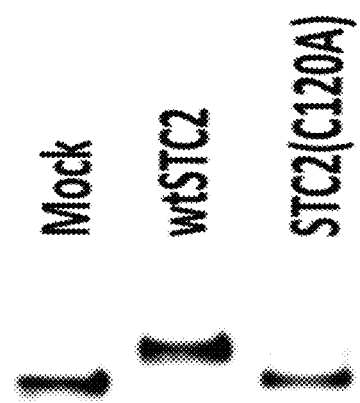
FIG. 8: PAPP-A western blot. PAPP-A was incubated ON at 37 C with conditioned medium from either mock, STC2, or mutated STC2, in which cysteine 120 is replaced with an alanine residue (C120A). Samples were separated by SDS-PAGE, blotted onto a PVDF membrane and bands visualized with polyclonal anti-PAPP-A antibodies. No band-shift is observed with the C120A mutant, demonstrating that cysteine 120 of STC2 is responsible for the formation of a covalent disulphide complex with PAPP-A.

Finally, it was tested if the proteolytic activity of PAPP-A was affected by complex formation with the STCs. PAPP-A was pre-incubated with mock-medium or medium containing recombinant STC1 or STC2. PAPP-A/STC2 complex formation was verified by Western blotting. The proteolytic activity of PAPP-A and PAPP-A/STC was monitored using $^{125}$I-IGFBP-4 pre-incubated with IGF-II as described previously. PAPP-A mediated proteolytic cleavage of IGFBP-4 at different time points was determined by correlating the intensities of bands representing intact and cleaved IGFBP-4, separated by SDS-PAGE (FIG. 6A).

After 120 minutes PAPP-A pre-incubated with mock-medium had cleaved 60% of the total IGFBP-4. Pre-incubation with STC1 or STC2, however, had rendered PAPP-A unable to cleave its substrate. As shown in FIG. 6B, only ~15% of the total IGFBP-4 was cleaved when STC1 was present while the presence of STC2 fully inhibited PAPP-A mediated IGFBP-4 cleavage. This demonstrates an inhibitory function of the STCs on PAPP-A proteolytic activity against IGFBP-4.

Example 2

The Stanniocalcins Regulate Mammalian Growth by Proteolytic Inhibition of the IGF Axis Materials and Methods Proteolytic cleavage assays and kinetic analyses were carried out with 125I-labeled natural substrate (IGFBP-4). Cleavage products were separated from intact substrate by SDS-PAGE, and cleavage was analyzed by photostimulated luminescence. Protein interaction studies and circular dichroism analysis were done using purified recombinant proteins. Assessment of protein concentrations were performed by quantitative amino acid analysis or by using immunoassays.

Formation in vitro of covalent complexes between STC2 and human or murine pappalysins was carried out by cotransfection of mammalian cells or by incubating media from separately transfected cells. Complex formation was documented or monitored by Western blotting. IGF-I receptor activation analysis was done using a cell line stably expressing the IGF-I receptor followed by quantification of receptor phosphorylation by Western blotting.

Transgenic mice expressing STC2 or STC2(C120A) were generated using a ubiquitously strong promoter. Growth of mice was monitored by consecutive weighing. Monoclonal antibodies, raised against STC2, were used to determine the levels of circulating transgene-derived STC2, and for immunoprecipitation of transgene-derived STC2 and endogenous PAPP-A present in primary fibroblasts derived from transgenic E13.5 embryos.

Plasmid Constructs and Mutagenesis

Plasmid DNA containing the coding sequence of human STC1 (nt. 285-1025 of NM_003155.2 flanked by a 5' XhoI site and a 3' HindIII site) and STC2 (nt. 1131-2216 of NM_003714.2 flanked by a 5' XhoI site and a 3' HindIII site) were purchased (Invitrogen). The cDNAs were cloned into the XhoI/HindIII sites of pcDNA3.1/Myc-His(−)A (Invitrogen) to obtain pSTC1 and pSTC2. The generation of plasmid constructs encoding human PAPP-A, murine PAPP-A, human PAPP-A2, human IGFBP-47, and human IGFBP-530 were reported elsewhere. To generate an expression plasmid for murine PAPP-A2 (NM_001085376.2), cDNA was synthesized from mouse placental mRNA using two specific primers (5'-CCGAGAGGTCAGGAGAGCAG-3' (nt. 3120-3101) (SEQ ID NO: 7) and 5'-GAGCTTCTCTTT-TAGTCTGCCCCC-3' (nt. 5425-5402) (SEQ ID NO: 8). Two overlapping PCR fragments, both containing the BglII site at nt. 2957, were generated using two sets of primers (5'-CCGGGGTACCATGATGTGTTGGAAGGTCCTGAG-3' (nt. 1-23, KpnI underlined) (SEQ ID NO: 9) and 5'-GATGGTGAGCGGTATGTCACAA-3' (nt. 3030-3009) (SEQ ID NO: 10); 5'-CCGGTCCAGGCGGATACCCT-3' (nt. 2881-2900) (SEQ ID NO: 11) and 5'-GATCTCTAGAT-TACTGGTTTTCTTCTGCCTTGGGG-3' (nt. 5370-5346, XbaI underlined) (SEQ ID NO: 12). The fragments were ligated and cloned into the KpnI/XbaI sites of pcDNA3.1(+) (Invitrogen) to generate pmPAPP-A2.

Mutagenesis of pSTC2 was carried out by QuikChange (Stratagene) using pSTC2 as a template, and the following sets of primers (numbering of NM_003714.2, mutated nucleotides underlined): 5'-GCACAGGTTCGGCGCCAT-AAGCCGGAAGTG-3' (nt. 1655-1684) (SEQ ID NO: 13) and 5'-CACTTCCGGCTTATGGCGCCGAACCTGTGC-3' (nt. 1684-1655) (SEQ ID NO: 14) for pSTC2(C120A), 5'-CAGCGTGCAGGTTCAGGCTGAGCAGAACTGGG-GAAG-3' (nt.1883-1918) SEQ ID NO: 15) and 5'-CTTCCCCAGTTCTGCTCAGCCT-GAACCTGCACGCTG-3' (nt.1918-1883) (SEQ ID NO: 16) for pSTC2(C197A), and 5'-GAACTGGG-GAAGCCTGGCCTCCATCTTGAGCTTC-3' (nt. 1907-1940) (SEQ ID NO: 17) and 5'-GAAGCTCAAGATG-GAGGCCAGGCTTCCCCAGTTC-3' (nt. 1940-1907) (SEQ ID NO: 18) for pSTC2(C205A). The mutated cDNAs were swapped into pSTC2 using the XhoI/HindIII sites. All constructs were verified by sequence analysis.

Cell Culture and Transfection

Human embryonic kidney 293T cells (293tsA1609neo) were maintained in high-glucose DMEM supplemented with 10% fetal bovine serum, 2 mM glutamine, nonessential amino acids, and gentamicin (Invitrogen). For transient transfection, $6.0 \times 10^6$ cells were plated onto 10-cm dishes and transfected 18 h later by calcium phosphate coprecipitation using 5-10 μg plasmid DNA prepared by GenElute HP Plasmid Miniprep Kit (Sigma). Culture supernatants were harvested 48 h post transfection and cleared by centrifugation, or the cells were further cultured in serum free medium (CD293, Invitrogen) to facilitate purification. Secreted levels of PAPP-A were determined by a commercial ELISA (AL-101, Ansh Labs), and levels of PAPP-A2 were measured by ELISA as previously described.

Protein Purification

Purification of His-tagged recombinant proteins was carried out by affinity chromatography on a 1 ml HisTrap HP column (GE Healthcare). Serum-free media were diluted 1:1 in 20 mM NaH2PO4, 150 mM NaCl, pH 7.4 (PBS) and loaded onto the column with a flow rate of 1 ml min$^{-1}$. The column was washed with 20 column volumes of 50 mM $NaH_2PO_4$, 1 M NaCl, 20 mM imidazole, 0.05% Tween-20, pH 7.4, followed by five column volumes of PBS. The proteins were eluted with 50 mM $NaH_2PO_4$, 300 mM imidazole, pH 7.4, and dialyzed against 20 mM HEPES, 150 mM NaCl, pH 7.4. Prior to iodination, IGFBP-4 and -5 were further purified by reversed-phase high pressure liquid chromatography (RP-HPLC) on a Discovery BIO Wide Pore C5 column (4×250 mm, Sigma), as described. Protein purity was assessed by SDS-PAGE, and quantification of purified proteins was done by amino acid analysis.

Proteinase Assays and Kinetic Analysis

Purified IGFBP-4 was labeled with $^{125}$I (Amersham Biosciences), and cleavage reactions were carried out as previously described. In brief, media harvested from cells transfected with human PAPP-A cDNA with or without pSTC1, pSTC2, or pSTC2(C120A) were diluted (1:500) to 50 pM PAPP-A and mixed with preincubated $^{125}$I-IGFBP-4 (10 nM) and IGF-II (100 nM) (GroPep Bioreagents) in 50 mM Tris-HCl, 100 mM NaCl, 1 mM CaCl2, pH 7.5. Following 10-40 min of incubation at 37° C., the reactions were terminated by the addition of hot SDS-PAGE sample buffer supplemented with 25 mM EDTA. Substrate and cleavage products were separated by 12% SDS-PAGE and visualized by autoradiography using a storage phosphor screen (Molecular Dynamics) and a Typhoon imaging system (GE Healthcare). For some reactions, media from cells transfected with human or murine PAPP-A cDNA were incubated for 0 or 16 h at 37° C. with culture media containing a molar excess of STC1 or STC2 prior to dilution and analysis of activity.

To quantitatively assess the inhibitory activity of STC1 and STC2(C120A), the proteolytic activity of human and murine PAPP-A (20-50 pM) against IGFBP-4 was analyzed in the presence of 0-1000 nM of purified STC1 or STC2 (C120A). Separate reactions were terminated at five different time points (0-120 min), depending on inhibitor concentrations. Cleavage was visualized as above, and band intensities were quantified by using the ImageQuant TL 8.1 software (GE Healthcare). Background signals were subtracted, and relative initial velocities (V/VO) were determined by linear regression assuming no substrate depletion. Determinations of inhibitory constants (Ki) were carried out by using the Morrison Ki model (competitive inhibition) embedded in the GraphPad Prism 5.0 software.

Cleavage of $^{125}$I-IGFBP-5 was assessed similarly for the following proteinases with or without a 10-fold molar excess of purified STC1 or STC2: Human MMP-2 (R&D Systems, 902-MP-010), human ADAM-10 (R&D Systems, 936-AD-020), human matriptase, bovine trypsin (Sigma, T-8642), and human or murine PAPP-A2. Enzyme concentrations were 100 nM, except for trypsin (0.2 nM) and PAPP-A2 (50 pM). STC2 was preincubated with all proteinases for 8 h.

Cleavage reactions were 30-180 min, to obtain approximately 30% substrate cleavage.

Primary Antibodies

For Western blotting, the following antibodies were used: Rabbit polyclonal anti(human PAPP-A), rabbit polyclonal anti(human PAPP-A2), mouse monoclonal anti(c-myc) (9E10, ATCC), goat polyclonal anti(human STC1) (R&D Systems, AF2958), goat polyclonal anti(human STC2) (R&D Systems, AF2830), mouse monoclonal PY99 (Santa Cruz Biotechnology, sc-7020) for detection of phosphotyrosine residues, mouse monoclonal CT-1 (GroPep Bioreagents, MAJ1) for detection of human IGF-I receptor, mouse monoclonal AC-74 (Sigma, A5316) for detection of β-actin, and mouse monoclonal D8-mIgG2a for detection of murine PAPP-A.

For use in ELISA and for immunoprecipitation, monoclonal antibodies against STC2 were raised. Initial injections of 50 μg of purified recombinant human STC2 was given to BALB/c mice subcutaneously in Freund's Complete Adjuvant (MP Biomedicals). A booster injection in Freund's Incomplete Adjuvant (MP Biomedicals) was given after one month. Based on screening of tail blood on STC2-coated plates, responders were selected for final boosting one month after the first booster injection. For four consecutive days, mice received intraperitoneal injections of 160 μg STC2. On the fifth day, the mice were sacrificed and the spleens removed. Spleen cells were centrifuged, aliquoted and stored in liquid nitrogen. Fusion with SP2/0 cells was performed with one aliquot of the spleen cells. Culture supernatants of picked clones were screened on STC2 coated plates, and positive clones were re-cloned. Resulting clones were STC216, STC220, STC221, STC225, STC239, and STC243. The clones were cultured in CD Hybridoma Medium (Invitrogen) for antibody production. Antibodies were purified on protein A Sepharose (GE Healthcare), and dialyzed against 20 mM HEPES, 150 mM NaCl, pH 7.5.

For biotinylation, mAb STC216 was incubated at 7.4 μM with a 20-fold molar excess of EZ-Link Sulfo-NHS-LC-Biotin (Thermo Fisher Scientific, #21335) on ice for 2 h. The reaction was stopped with 10 mM Tris-HCl, and dialyzed against 20 mM HEPES, 150 mM NaCl, pH 7.5.

Enzyme-Linked Immunosorbent Assays (ELISA)

For measurement of STC2 concentration, 96-well plates (MaxiSorp, Nunc) were coated with 100 μl per well of 7.5 μg ml$^{-1}$ of catching antibody (mAb STC221) in 100 mM Na$_2$HCO$_3$, pH 9.4 by overnight incubation at 4° C. The wells were then blocked with 200 μl per well of 2% bovine serum albumin (BSA) in TBS (30 mM Tris-HCl, 300 mM NaCl, 2 mM CaCl2), pH 7.4) for 30 min at 37° C. Samples were diluted in TBS-T (TBS containing 0.05% Tween-20) supplemented with 1% BSA and incubated in the coated wells for 1 h at 37° C. Following washing in TBS-T, the wells were incubated for 1 h at 37° C. with biotinylated detecting antibody (STC216) diluted in TBS-T with 1% BSA to 1 μg ml$^{-1}$, washed again, and incubated (1 h) with avidin-conjugated horseradish peroxidase (P0347, DAKO) diluted 1:20,000 in TBS-T with 1% BSA. Following a final round of washing, the wells were developed using OPD Tablets (S2045, DAKO). Calibrators were based on recombinant STC2 diluted in TBS-T with 1% BSA. Eight calibration points (6.25-800 ng ml$^{-1}$) were used. Absorbance was measured at 490 nm on an EnSpire Multimode Plate Reader (Perkin Elmer). Blank values were subtracted and data were analyzed by using cubic curve fitting. The functional sensitivity of the assay at 20% CV was 20 ng ml$^{-1}$.

To assess monoclonal antibody binding to STC2 and STC2(C120A), plates were coated with 100 μl per well of 2 μg ml$^{-1}$ polyclonal anti(STC2). Detection was carried out with available STC2 mAbs (1 μg ml$^{-1}$) followed by anti-mouse IgG-HRP (DAKO, P0260) diluted 1:2000. Signals from dilution series of STC2 and STC2(C120A) were normalized and compared for each of the antibodies. Buffers for dilution and washing were as described above.

Immunoblotting and Analysis of Complex Formation

Proteins separated by SDS-PAGE were blotted onto a PVDF membrane (Millipore), blocked with 2% Tween 20, and equilibrated in 50 mM Tris-HCl, 500 mM NaCl, 0.1% Tween 20, pH 9.0 (TST). Primary antibodies were diluted (to 1-5 μg ml$^{-1}$) in TST containing 0.5% fetal bovine serum, and blots were incubated overnight at room temperature. The blots were incubated for 1 h at room temperature with secondary antibodies (polyclonal swine anti-rabbit IgG-HRP (DAKO, P0217), polyclonal rabbit anti-goat IgG-HRP (DAKO, P0160), or polyclonal rabbit anti-mouse IgG-HRP (DAKO, P0260)) diluted 1:2000 in TST containing 0.5% fetal bovine serum. All washing between the steps was carried out with TST. The blots were developed using enhanced chemiluminescence (ECL Prime, GE Healthcare), and images were captured and analyzed using an ImageQuant LAS 4000 instrument (GE Healthcare).

To probe for covalent complex formation between proteins synthesized in separate cells, culture media were incubated 0-16 h at 37° C., separated by nonreducing SDS-PAGE (2 μl per lane), and then analyzed by Western blotting as described above. Media from cotransfected cells were not incubated prior to analysis.

Surface Plasmon Resonance Analysis

Surface plasmon resonance experiments were carried out on a Biacore T200 (GE Healthcare). Using amine coupling, purified monoclonal antibody 234-5 was immobilized in flow cells (FC) 3 and 4 of a Series S CM5 Sensor Chip (GE Healthcare). To reach a coupling density of 5,000 response units (RU), the antibody was diluted to 30 μg ml$^{-1}$ in 10 mM sodium acetate, pH 4.75. Remaining active groups were blocked by a 7 min injection of 1 M ethanolamine, pH 8.0. For data collection, recombinant human PAPP-A (350 RU) in culture medium was captured in FC4 only, using FC3 as a reference cell. A twofold serial dilution (6.25 nM to 195 pM) of purified recombinant human STC1 in 10 mM HEPES pH 7.5, 150 mM NaCl, 1 mM CaCl2) and 0.05% Tween-20, was injected over both FCs at 30 μl min$^{-1}$. The association phase was 180 s, followed by a 1,000 s dissociation phase. At the end of each binding cycle, both surfaces were regenerated by a 40 s injection of 0.1 M glycine, pH 2.5, and 0.5 M guanidine hydrochloride. Analyte (STC1) concentration was determined by amino acid analysis. Binding analysis was performed at 25° C., and data were collected at a rate of 10 Hz. Recorded signals were subtracted the background signal, as determined by the response obtained from the reference cell. Global fitting of a 1:1 Langmuir model was performed, using the Biacore T200 Evaluation Software, version 1.0.

Circular Dichroism Analysis

Purified wild-type and mutant proteins were compared by using circular dichroism analysis. Prior to analysis, purified proteins were dialyzed against 20 mM NaH2PO4, 20 mM NaF, pH 7.4. Ten CD spectra were recorded at 25° C. for each protein on a Jasco J-810 spectropolarimeter (Jasco Spectroscopic, Japan) using a polypeptide concentration of 0.5 mg ml$^{-1}$ and a cuvette of 2 mm path length. CD data were obtained in the range from 260 to 190 nm at a resolution of 0.2 nm using a bandwidth of 1.0 nm. The scan speed was 100 nm min$^{-1}$, and the response time was 1 s. Temperature scans were carried out in the range from 260 to 200 nm, and melting curves were recorded at 222 nM. Δε (expressed in deg cm² dmol⁻¹) were calculated on the basis of a mean molar mass of 110 g mol⁻¹ residue⁻¹.

IGF-1 Receptor Stimulation Assay

A cell line stably expressing the IGF-I receptor, 293-IGFR (clone H), was used to measure IGF-I receptor phosphorylation, essentially as described. Starved cells were rinsed in PBS containing CaCl¬2 (0.1 mg liter⁻¹) and MgCl2 (0.1 mg liter⁻¹), pH 7.4, and stimulated for 15 min with combinations of IGF-I (10 nM), IGFBP-4 (50 nM), PAPP-A (2.5 nM), and STC1 (15 nM) or STC2 (15 nM). Before stimulation, IGF-I and IGFBP-4 were incubated for 20 min at 37° C. in 20 mM HEPES, 100 mM NaCl, 1 mM CaCl2, pH 7.5, to allow the IGF-I/IGFBP-4 complex to form. PAPP-A was then added and cleavage reactions were carried out in the same buffer for 20 min at 37° C. Prior to use, PAPP-A was incubated with or without STC1, STC2, or STC2(C120A) in serum medium for 16 h at 37° C. The stimulated cells were lysed on ice with RIPA buffer (Sigma, R0278), supplemented with Proteinase Inhibitor Cocktail (Sigma, P8340) and Phosphatase Inhibitor Cocktail Set II (EMD Millipore, 524625), for 10 min. Western blotting of cleared lysates was used to quantitate β-subunit phosphorylation using mAb PY99. Detection of total IGF-I receptor was done using mAb CT-1. For loading controls, blots were stripped and reprobed with mAb AC-74 towards actin. Quantification of band intensities was carried out using an ImageQuant LAS 4000 instrument (GE Healthcare). The signals of mAb PY99 were subtracted background signals and plotted.

Animal Experiments

For the production of transgenic mice, PCR fragments encoding untagged STC2 or STC2(C120A) were generated by using the primers 5'-CGCAAATGGGCGGTAGGCGTG-3' (nt. 769-789 of pcDNA3.1-Myc-His(-)A) (SEQ ID NO: 19) and 5'-AAAAAAAGATCTTCACCTCCGGA-TATCAGAATACTC-3' (nt. 2219-2196 of NM_003714.2, BglII site underlined) (SEQ ID NO: 20), and pSTC2 and pSTC2(C120A), respectively, as templates. The PCR fragments were cloned into the XhoI/BglII sites of pCAGGS (BCCM, LMBP 2453) to generate pCAGGS-STC2 and pCAGGS-STC2(C120A). Plasmid DNA was linearized with PvuI, and microinjected into male pronuclei of B6D2F2 zygotes (Taconic), which were then introduced into pseudopregnant NMRI female mice (Taconic). Transgenic mice, B6D2F2-Tg(STC2), or B6D2F2-Tg(STC2(C120A)), were identified by PCR using pCAGGS plasmid-specific primers (5'-CGGAAGGACATATGGGAGGGCAAATC-3' (nt. 216-241) (SEQ ID NO: 21), and 5'-TGACTGG-GAGTAGTCAGGAGAGGAGG-3' (nt. 511-486) (SEQ ID NO: 22), and genomic DNA purified from tail biopsies. Of 44 mice resulting from pCAGGS-STC2-injections, nine were positive for the transgenic insert. Four of these gave rise to transgenic offspring with detectable levels of STC2 antigen in the serum, and were used as founders for further breeding. Similarly, of 34 mice resulting from pCAGGS-STC2(C120A)-injections, nine were positive. Three of these gave rise to transgenic offspring with detectable levels of STC2 in the serum, and were used as founders. Founders were bred with C57BL/6JBomTac (Taconic), giving rise to litters containing B6;D2-Tg(STC2)N1 or B6;D2-Tg(STC2 (C120A))N1 mice as well as wild-type littermates, which were genotyped and analyzed blinded for growth by consecutive weighing. At weeks five and eight, blood was drawn from the sublingual vein, serum was allowed to form, and the samples were frozen and stored at -20° C. until further analysis. For weight comparisons, mice were grouped according to individual serum levels of STC2. For all groups of B6;D2-Tg(STC2)N1, and for the 2-8 μg ml⁻¹ group of B6;D2-Tg(STC2(C120A))N1, n refers to the number of mice included at all time points. For the nontransgenic group of B6;D2-Tg(STC2(C120A))N1, n refers to the number of mice included at all time points, except for weeks 3 (n=9) and 7 (n=5). The mice were kept on a 12-h light/12-h dark cycle and given Altromin 1319 (Brogaarden) ad libitum. All mouse work was conducted with permission of the national Danish authorities (Dyreforsøgstilsynet).

Culture and Analysis of Mouse Embryonic Fibroblasts

Primary cultures of mouse embryonic fibroblasts (MEFs) were derived from E13.5 embryos resulting from mating B6;D2-Tg(STC2)N1 female and male littermates. The embryos were washed, minced, digested with papain, and cell suspensions were plated in DMEM culture medium supplemented with 55 μM β-mercaptoethanol (Invitrogen). Cells at passages 2-4 were used for experiments. Residual tissue from each embryo was used for genotyping, and the presence of transgene-derived STC2 secreted into the culture media was confirmed by ELISA. Culture media from nontransgenic or transgenic MEFs were assessed for the presence of proteolytic activity towards IGFBP-4, with or without the addition of mAb 1/41 (100 nM), a monoclonal antibody inhibitory towards PAPP-A proteolytic activity17.

Transgenic STC2 contained in the media of confluent plates was immunoprecipitated from 20 ml of media using 30 μl of Protein G Sepharose 4 Fast Flow (GE Healthcare), to which mAb STC221 was immobilized at 2 mg ml⁻¹ by using dimethyl pimelimidate dihydrochloride (Sigma) cross-linking, essentially as described. Eluted protein was assessed for the presence of endogenous murine PAPP-A by Western blotting using mAb D8-mIgG2a.

Statistical Analysis

All statistical analyses were performed using GraphPad Prism version 5.0. Statistical analysis of mouse postnatal growth data was performed using the unpaired Student's t-test for each time point. Statistical analysis of IGF-I receptor signaling and was performed using one-way ANOVA followed by Dunnett's test. Statistical analysis of antibody binding was performed using one-way ANOVA followed by Tukey's test. $P<0.05$ was considered statistically significant.

Results

Figure 11:
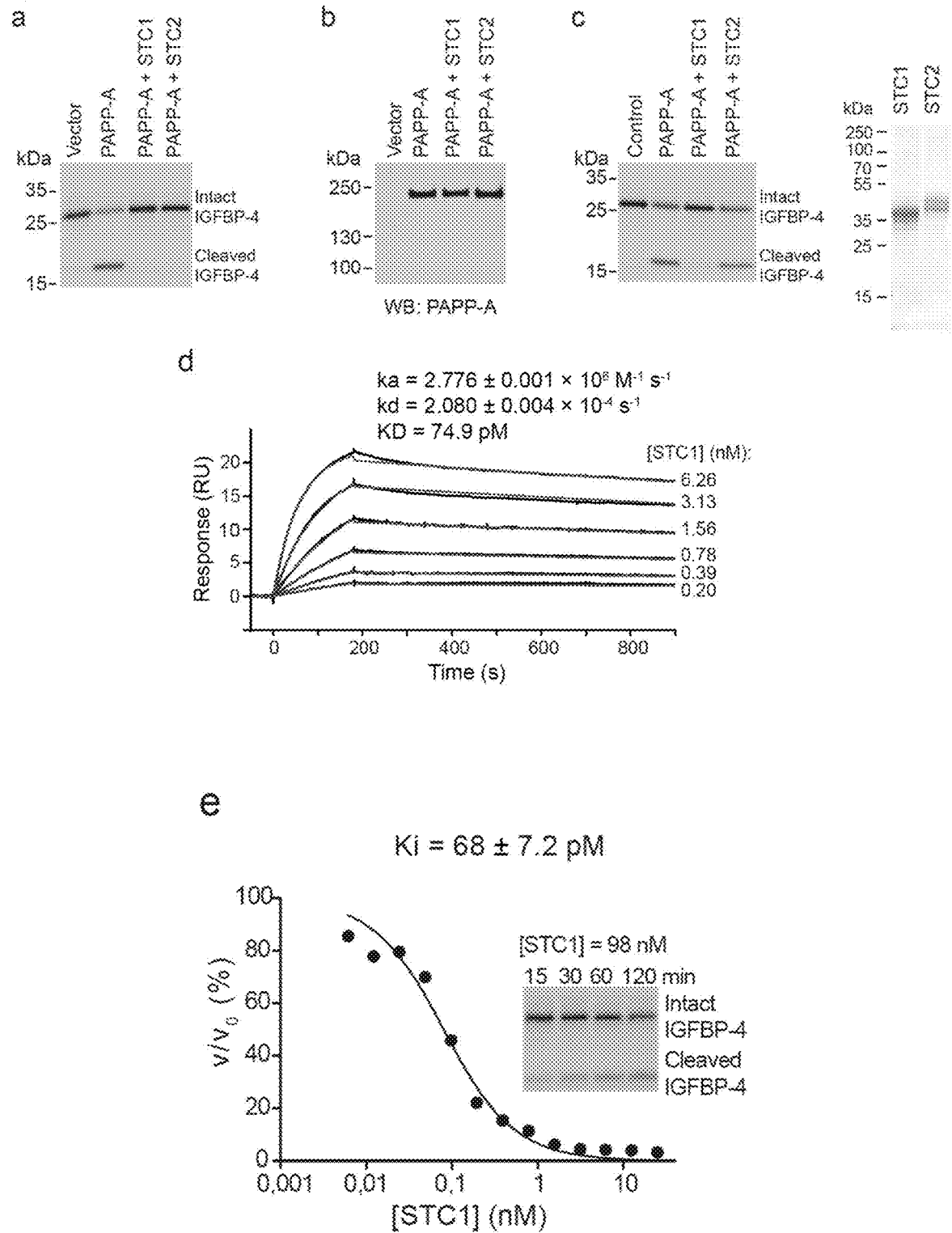
FIG. 11: STC1 and STC2 inhibit the proteolytic activity of PAPP-A. a, PAPP-A proteolytic activity towards radiolabeled IGFBP-4 in media from HEK293T cells transfected with combinations of cDNAs as indicated. b, PAPP-A Western blot of samples from a. c, PAPP-A proteolytic activity towards radiolabeled IGFBP-4 in the presence or absence of purified STC1 or STC2 added at the beginning of the cleavage reaction. Right panel: Coomassie-stained SDS-PAGE gels of purified proteins. d, Surface plasmon resonance analysis of STC1 binding to PAPP-A. e, Kinetic analysis of STC1 inhibition of PAPP-A cleavage of IGFBP-4. All gel images and the immunoblot are representative of at least four independent experiments.

PAPP-A secreted from transfected cells rapidly cleaves IGFBP-4 at a single site in vitro. However, we detected no proteolytic activity towards IGFBP-4 upon cotransfection with STC1 or STC2 cDNA (FIG. 11a), even though the level of PAPP-A secreted from the cells was unaffected (FIG. 11b). To assess the possible function of STC1 and STC2 as proteinase inhibitors, we then analyzed the effect of adding separately synthesized and purified STCs to the cleavage reaction. STC1 still inhibited PAPP-A, but in this experiment, no inhibitory effect of STC2 was observed (FIG. 11c). Quantitative assessment of the interaction revealed that STC1 binds strongly to PAPP-A with a KD of 75 pM (FIG. 11d), and kinetic analysis showed that it potently inhibits (Ki=68 pM) the proteolytic activity of PAPP-A (FIG. 11e).

Figure 12:
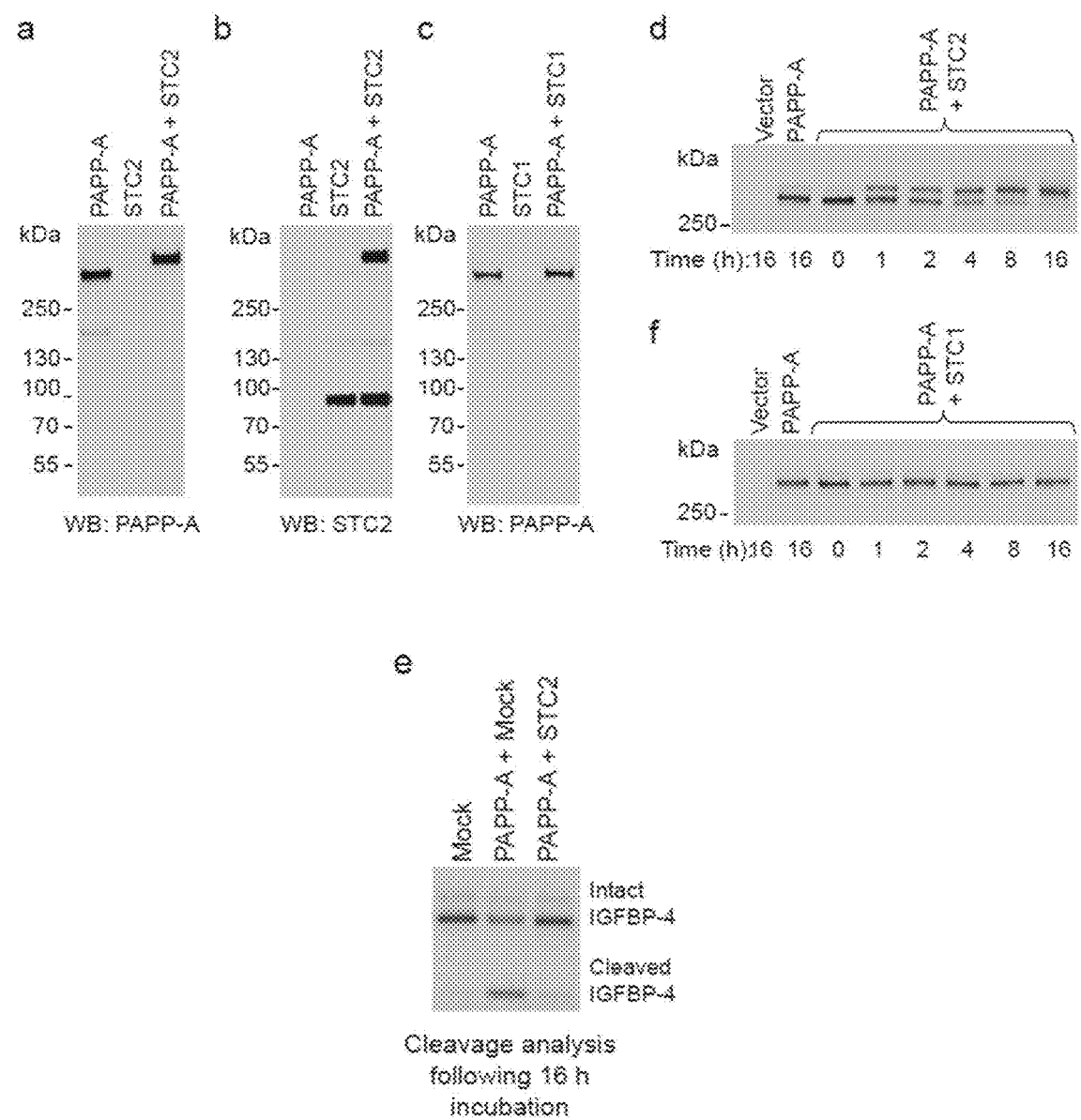
FIG. 12: Inhibition of PAPP-A by STC2 requires covalent complex formation. a, PAPP-A Western blot of medium from HEK293T cells transfected with combinations of cDNAs as indicated. b, STC2 Western blot of samples from a. c, PAPP-A Western blot of medium from HEK293T cells transfected with combinations of cDNAs. d, PAPP-A Western blot of separately synthesized PAPP-A and STC2 incubated for 0-16 h. e, PAPP-A proteolytic activity towards radiolabeled IGFBP-4 in 16 h-samples from d. f, PAPP-A Western blot of separately synthesized PAPP-A and STC1 incubated for 0-16 h. The immunoblots and the gel image are representative of at least four independent experiments.
Figure 15:
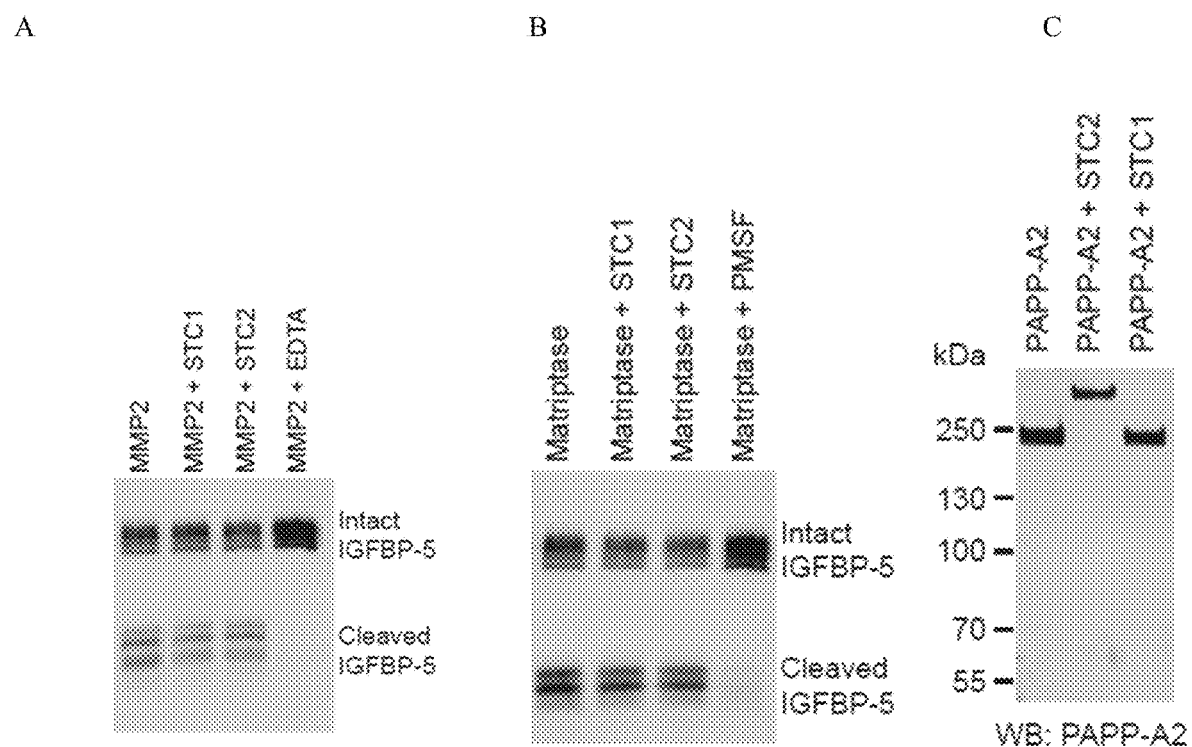
FIG. 15: STC1 and STC2 lack inhibitory activity towards selected proteolytic enzymes outside the pappalysin family, but inhibit PAPP-A2. a, Proteolytic cleavage of radiolabeled IGFBP-5 by matrix metalloproteinase-2 (MMP2, a metzincin metalloproteinase) preincubated (8 h) with buffer, STC1, STC2, or EDTA. Contrary to IGFBP-4, IGFBP-5 is promiscuously cleaved by many proteinases. b, As a, but using matriptase (a serine proteinase) and trypsin (a serine proteinase) and phenylmethylsulfonyl fluoride (PMSF). c, PAPP-A2 Western blot of medium from HEK293T cells transfected with cDNAs encoding human PAPP-A2 and STC1 or STC2. All gel images and the immunoblot are representative of at least four independent experiments.

Following separate transfection, STC2 and PAPP-A migrated in SDS-PAGE as dimers of approximately 90 kDa or 400 kDa, respectively, but upon cotransfection, a high-molecular weight band of approximately 500 kDa which contained both antigens was formed (FIG. 12a-b). No change in PAPP-A migration was observed in a similar experiment with STC1 (FIG. 12c). We conclude that STC2, but not STC1, is capable of forming a complex with PAPP-A which resists separation in denaturing PAGE and therefore most likely is covalent. We further analyzed the process of complex formation by incubating separately synthesized STC2 and PAPP-A. Interestingly, a PAPP-A-containing band of 500 kDa gradually appeared during the incubation (FIG. 12d), demonstrating complex formation in the extracellular environment. PAPP-A was proteolytically active following incubation alone, while after 16 hours of incubation with STC2, PAPP-A showed no activity (FIG. 12e). In agreement with the cotransfection experiments, STC1 did not form a covalent complex upon incubation with PAPP-A (FIG. 12f). We then assessed the possible inhibitory activity of the STCs towards other proteolytic enzymes. None of the proteinases tested was inhibited by STC1, or by STC2 following incubation (FIG. 15a-b). However, both STCs were able to partially inhibit PAPP-A2 (pappalysin-2), the only homolog of PAPP-A, and STC2, but not STC1, also formed a covalent complex with PAPP-A2. We therefore conclude that STC1 and STC2 function in vitro as proteinase inhibitors of the pappalysin family of metalloproteinases, comprised of PAPP-A and PAPP-A2. STC1 exerts its inhibitory function by forming a high-affinity proteinase-inhibitor complex, while STC2 inhibitory activity requires that it forms a covalent complex with its target proteinase. It is interesting to note that the homologous STCs have unique amino acid sequences with no known modules or motifs by which this biochemical function might have been predicted.

Figure 13:
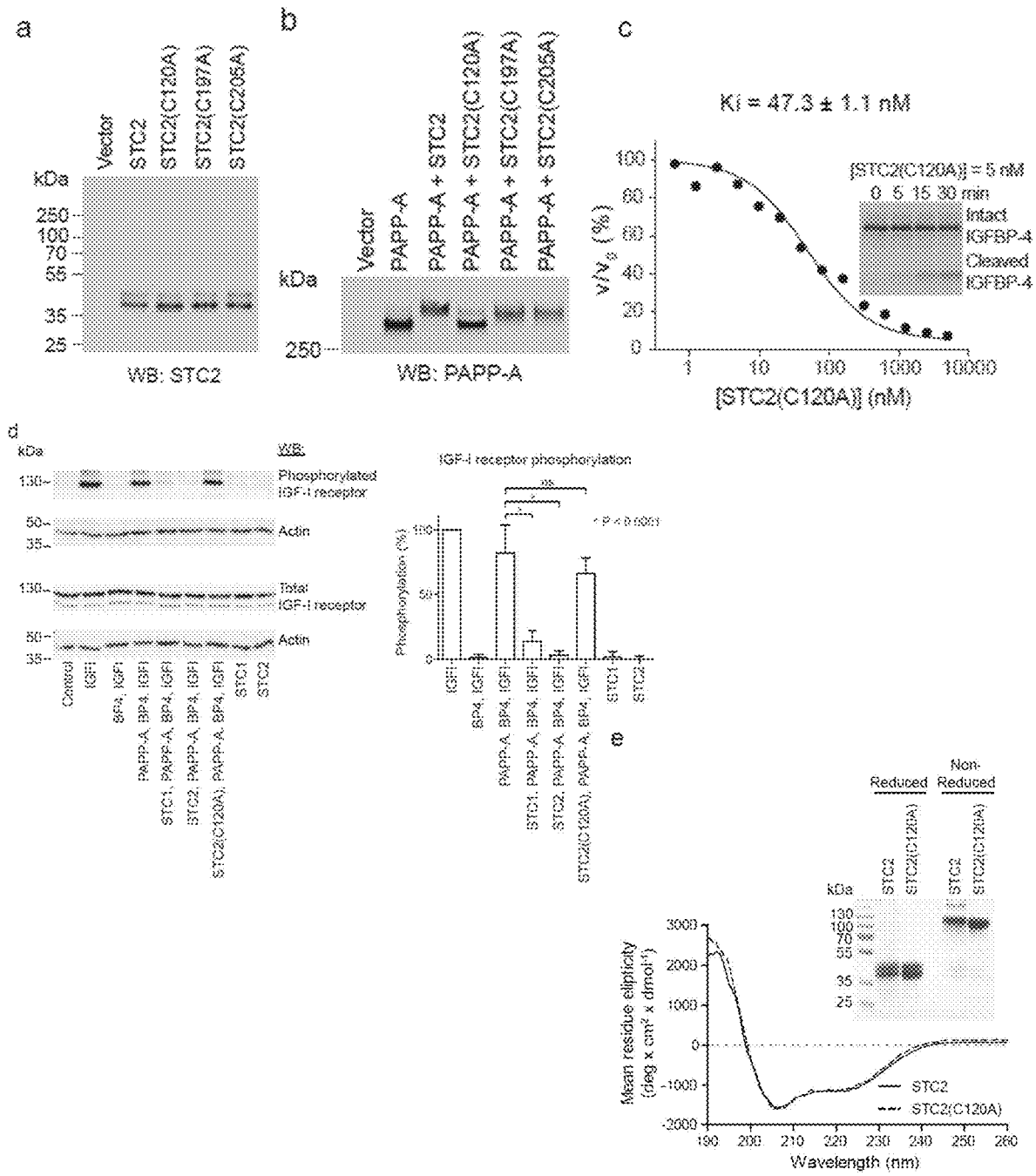
FIG. 13: Covalent binding to PAPP-A is mediated by C120 of STC2. a, STC2 Western blot of wild-type and mutated variants of STC2 as indicated. b, PAPP-A Western blot of media from HEK293T cells transfected with combinations of cDNAs. c, Kinetic analysis of STC2(C120A) inhibition of PAPP-A cleavage of IGFBP-4. d, Assessment of IGF-I receptor stimulation in vitro by combinations of IGF-I, IGFBP-4, PAPP-A and STCs. Quantified signals normalized to the signal with IGF-I alone are shown to the right. Results are means±s.d. from four independent experiments. ns, not statistically significant. e, Circular dichroism analysis of purified STC2 and STC2(C120A). Inset shows Coomassie-stained SDS-PAGE gel of purified STC2 and STC2(C120A). All immunoblots and gel images are representative of at least four independent experiments.
Figure 16:
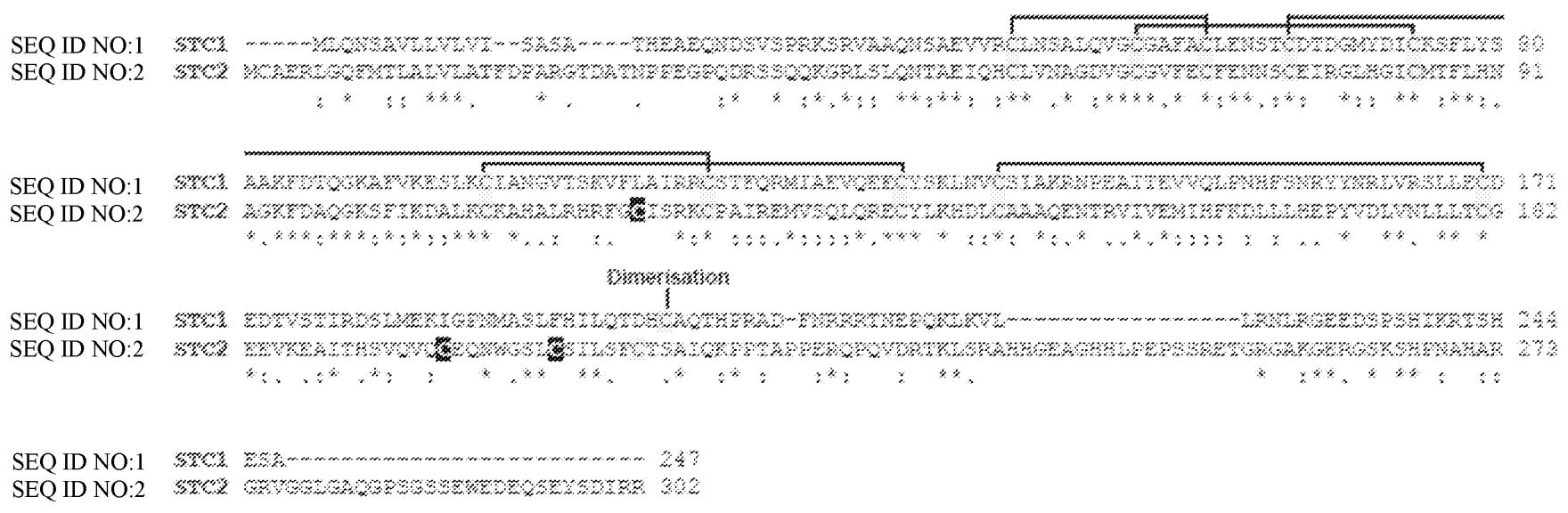

It has previously been shown that the 11 cysteine residues of STC1 form five intramolecular disulfide bonds, and that one residue is responsible for dimerization. These 11 cysteine residues are conserved in STC2, which, interestingly, contains three additional cysteines, C120, C197, and C205 (FIG. 16). When these three residues were substituted individually to alanine the level of expression was unchanged (FIG. 13a). However, mutant STC2(C120A) was unable to form a covalent complex with PAPP-A (FIG. 13b), indicating that an intermolecular disulfide bond involving C120 is the basis for the covalent linkage between STC2 and PAPP-A. To allow disulfide bond formation between STC2 and PAPP-A, the molecules must first interact noncovalently, likely mimicked by a relatively weak interaction between STC2(C120A) and PAPP-A. Concordantly, kinetic analysis showed that STC2(C120A) still possessed some inhibitory activity towards PAPP-A (Ki=47 nM) (FIG. 13c). In terms of inhibitory mode, STC2(C120A) resembles the noncovalent STC1, although its inhibitory potency is approximately 700 fold lower than STC1. Therefore, formation of a covalent bond between STC2 and PAPP-A compensates efficiently for the otherwise poor inhibitory activity of STC2. In agreement with these data, we find that both STC1 and STC2, but not STC2(C120A), efficiently inhibit PAPP-A-mediated IGF receptor signaling in vitro (FIG. 13d).

Figure 17:
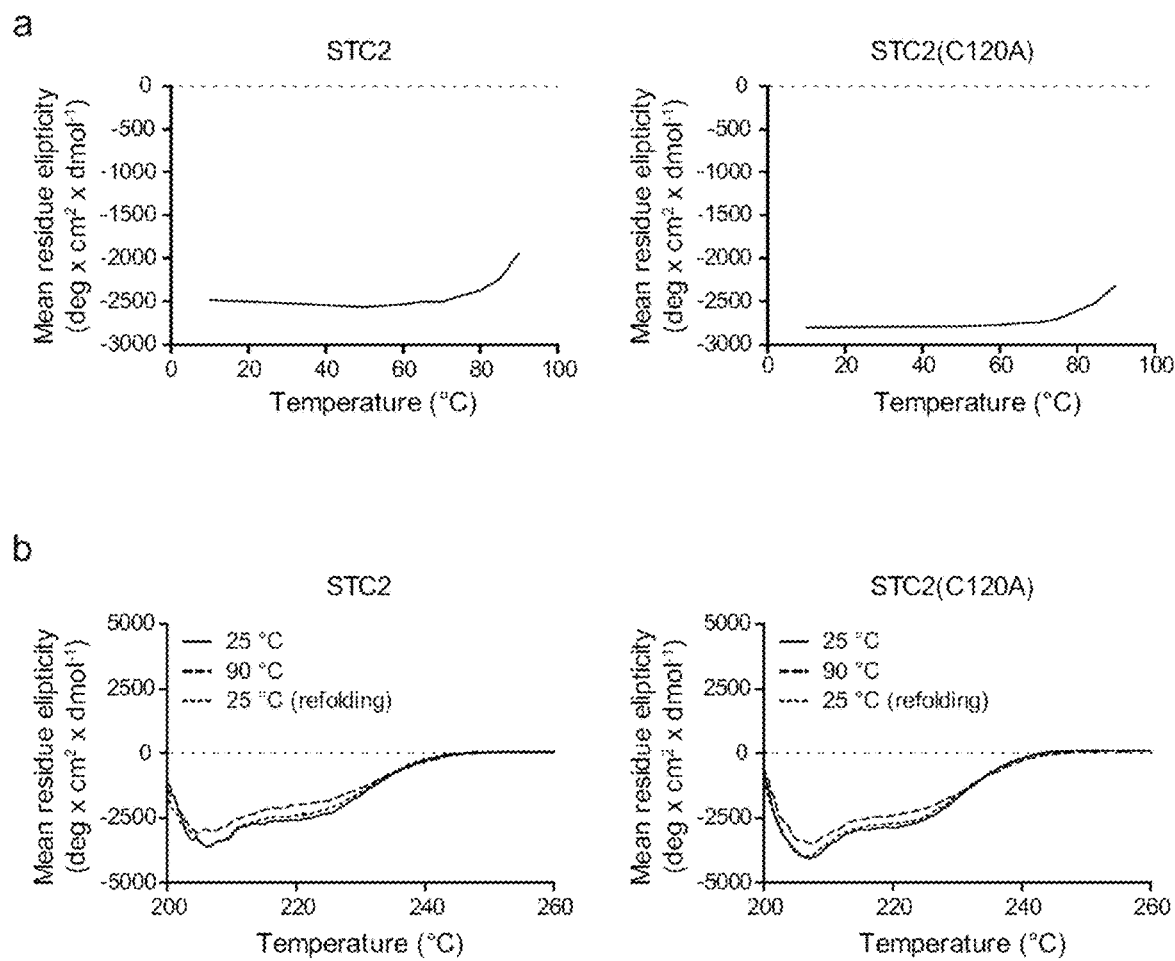
FIG. 17: Circular dichroism analysis of purified STC2 and STC2(C120A). a, Temperature scans showing changes in mean residue ellipticity at 222 nm. b, Spectra recorded at 25° C. and 95° C., and at 25° C. following incubation at 95° C. for 2 min.
Figure 18:
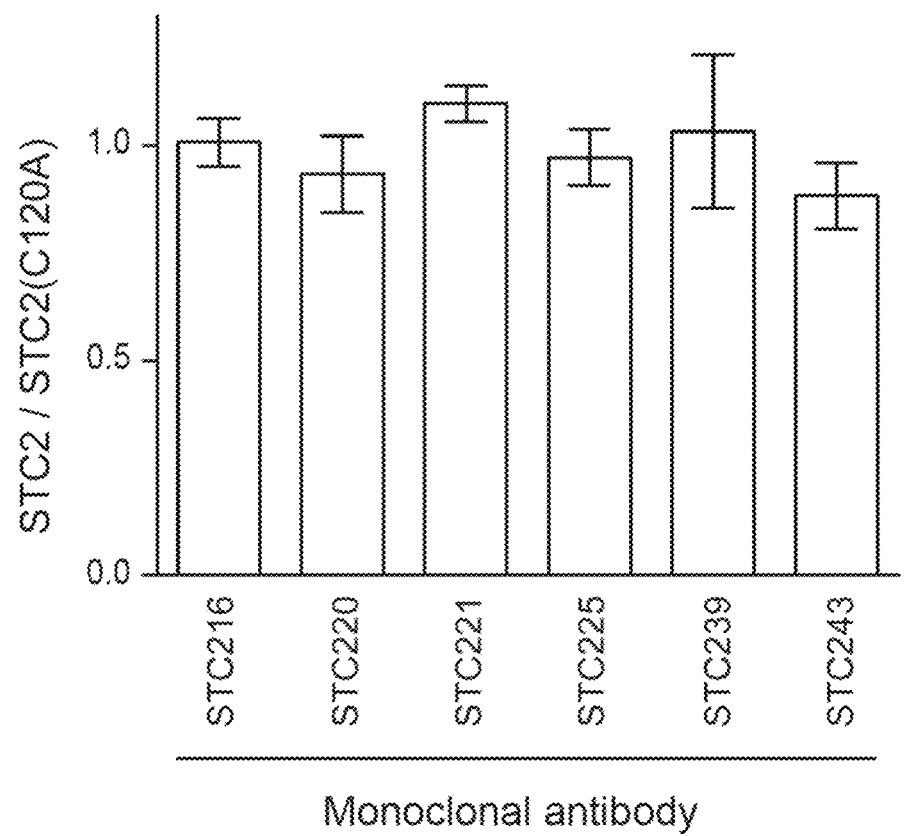
FIG. 18: Assessment of STC2 and STC2(C120A) antibody reactivity. The relative binding of available monoclonal antibodies to STC2 and STC2(C120A) is plotted. A value of 1 indicates equal binding to STC2 and STC2 (C120A). Results are means±s.d. from four independent experiments performed in triplicate. Differences in ratios are not statistically significant.
Figure 19:
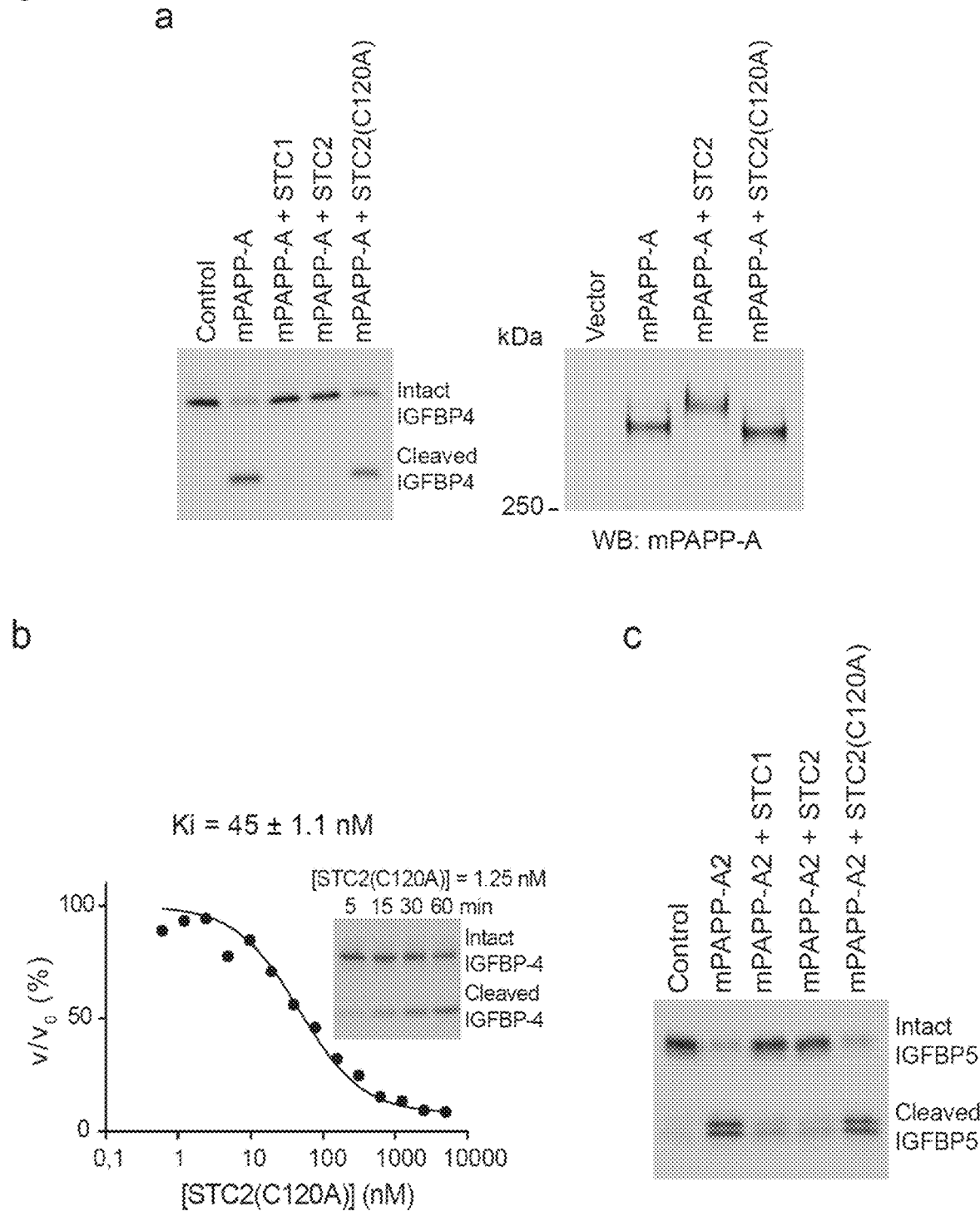
FIG. 19: Murine PAPP-A and PAPP-A2 are inhibited by STC1 and STC2, but not STC2(C120A). a, Proteolytic activity towards radiolabeled IGFBP-4 in medium from HEK293T cells transfected with cDNA encoding murine PAPP-A (mPAPP-A), preincubated with or without STC1, STC2, or STC2(C120A). Right panel: Western blot demonstrating covalent complex formation between murine PAPP-A and STC2, but not STC2(C120A). b, Kinetic analysis of STC2(C120A) inhibition of murine PAPP-A. c, Proteolytic activity towards radiolabeled IGFBP-5 in medium from HEK293T cells transfected with cDNA encoding murine PAPP-A2 (mPAPP-A2), preincubated with or without STC1, STC2, or STC2(C120A). All gel images and the immunoblot are representative of at least four independent experiments.

Prior to use in animal studies, we further compared purified STC2(C120A) and wild-type STC2 by circular dichroism analysis. Similar spectra and thermal stability suggest that the structural integrity of STC2(C120A) was not compromised by its single amino acid substitution (FIG. 13e and FIG. 17). Equal recognition of STC2 and STC2 (C120A) by six available monoclonal antibodies also supported this interpretation (FIG. 18). In addition, we verified that the biochemical properties of both STC2 and STC2 (C120A) are conserved in the murine system (FIG. 19a-c).

Figure 14:
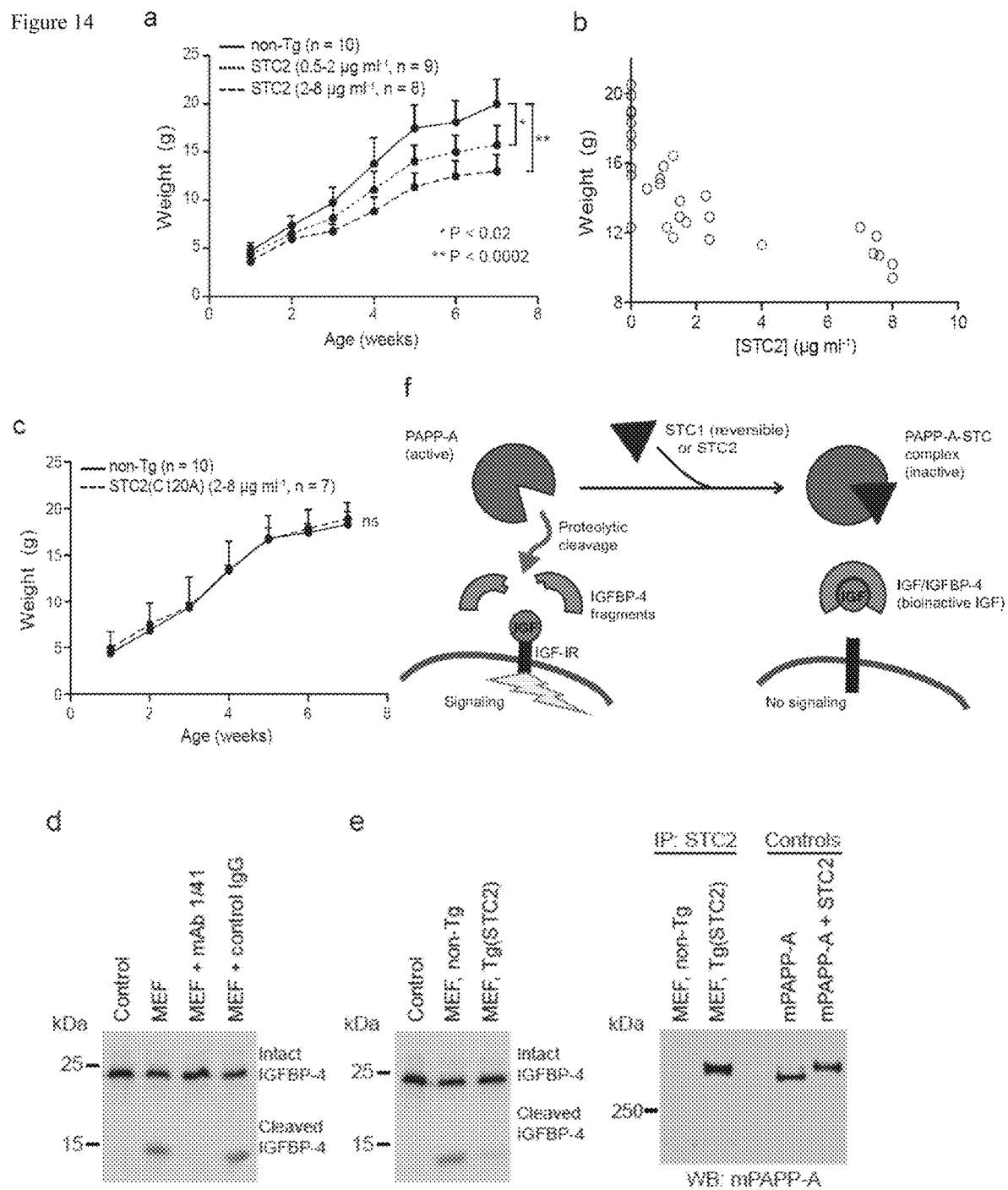
FIG. 14: Overexpression of STC2, but not STC2(C120A), causes growth retardation in mice. a, Growth curves of nontransgenic and STC2 transgenic female mice divided into groups according to circulating levels of STC2. Results are means with s.d. indicated. Statistical significance is based on comparison of mice older than three weeks. b, Body weight of STC2 transgenic female mice at week five as a function of measured levels of circulating transgene-derived STC2. c, Growth curves of nontransgenic and STC2(C120A) transgenic female mice. Results are means with s.d. indicated. ns, not statistically significant. d, Proteolytic activity towards radiolabeled IGFBP-4 in conditioned medium from mouse embryonic fibroblasts (MEFs) derived from nontransgenic mice in the presence or absence of mAb 1/41, a specific inhibitor of PAPP-A. e, Proteolytic activity towards radiolabeled IGFBP-4 in conditioned medium from STC2 transgenic or nontransgenic MEFs. Right panel: PAPP-A Western blot of endogenous murine PAPP-A coimmunoprecipitated (IP) with transgenic STC2. f, Model depicting the balance between active and STC-inhibited PAPP-A, indirectly affecting IGF-I receptor stimulation. All gel images and the immunoblot are representative of at least four independent experiments.

To test our prediction that overexpression of STC2 causes growth retardation by proteolytic inhibition, we generated and compared mice transgenic for STC2 and STC2(C120A). In agreement with earlier findings 4, STC2 overexpression caused a severe reduction in postnatal growth rate compared to nontransgenic animals (FIG. 14a). Our data further indicate a correlation between the circulating level of STC2 and the severity of the growth retardation (FIG. 14b). In striking contrast, transgenic expression of STC2(C120A) did not cause a detectable alteration in growth rate, even at high levels of circulating protein (FIG. 14c).

Cultured mouse embryonic fibroblasts (MEFs) from PAPP-A knockout mice lack proteolytic activity towards IGFBP-4. We find that the activity towards IGFBP-4, present in conditioned media from MEFs derived from nontransgenic mice, can be completely inhibited by using a novel inhibitory monoclonal antibody, specific for both murine and human PAPP-A (FIG. 14d). This experiment conclusively shows that MEF-derived proteolytic activity towards IGFBP-4 is caused by PAPP-A. In contrast to MEF media from nontransgenic mice, conditioned media from MEFs derived from STC2 transgenic mice showed a marked reduction in PAPP-A activity (FIG. 14e). Importantly, inhibition is accompanied by the presence of a covalent complex between endogenous PAPP-A and transgene-derived STC2 in the MEF culture medium (FIG. 14e). We therefore draw the conclusion that STC2 transgenic mice show growth retardation because the activity of PAPP-A is compromised.

In opposition to conditions of PAPP-A knockout or inhibition, the substantially increased body weight observed previously for STC2 knockout mice suggests that the absence of STC2 causes elevated PAPP-A activity. A strong anabolic effect of PAPP-A was also demonstrated by a markedly increased bone thickness upon targeted PAPP-A transgenic expression in osteoblasts, and similarly, by a large increase in skeletal muscle mass upon transgenic expression of PAPP-A in myoblasts. Finally, in humans, the growth regulatory potential of PAPP-A is underscored by the finding of a strong, positive correlation between birth weight and maternal first-trimester levels of PAPP-A.

Taken together, these findings support a model in which a dynamic balance between PAPP-A proteolytic activity and STC inhibitory activity determines IGF receptor stimulation locally in vivo (FIG. 14f). In this regard, it is important to stress that IGF-mediated growth depends on the level of pericellular, bioactive IGF in the tissue microenvironment. This is emphasized by the key finding that liver-specific knockout of IGF-I dramatically reduces (by 75%) serum levels of IGF-I, but has no effect on growth. It is also emphasized by the observation that levels of circulating IGF-I is not altered in mice that have become dwarfs as a result of STC1 or STC2 overexpression. Little knowledge exists on PAPP-A2, but gene targeting is known to cause mild growth retardation. Thus, in line with our biochemical data, a similar model is also valid for PAPP-A2, even though not widely expressed compared to PAPP-A.

Dysregulated IGF receptor signaling has been extensively linked to various diseases, in particular human cancer. Also, the involvement of PAPP-A in cancer development is increasingly recognized, and is underscored by the finding that PAPP-A knockout mice have a remarkably low incidence of spontaneous cancers of age. It is therefore interesting that multiple reports link STC1 or STC2 to human cancers. For example, loss of BRCA1 tumor suppressor function in breast cancer causes STC1 expression to become undetectable, and late relapse of breast cancer correlates with high expression of STC1 and STC2.

Overall, the present example demonstrates that the mammalian stanniocalcins are novel proteinase inhibitors of the complex extracellular network that regulates IGF receptor activation in vivo.

SEQUENCES

```
Stanniocalcin-1 (=STC1) precursor [Homo sapiens]
NCBI Reference Sequence: NP_003146.1
                                                              SEQ ID NO: 1
   1 mlqnsavllv lvisasathe aeqndsvspr ksrvaaqnsa evvrclnsal qvgcgafacl 61 enstcdtdgm ydicksflys aakfdtqgka fvkeslkcia ngvtskvfla irrcstfqrm 121 iaevqeecys klnvcsiakr npeaitevvq lpnhfsnryy nrlvrsllec dedtvstird 181 slmekigpnm aslfhilqtd hcaqthprad fnrrrtnepq klkvllrnlr geedspshik 241 rtshesa Stanniocalcin-2 (=STC2) precursor [Homo sapiens]
NCBI Reference Sequence: NP_003705.1
                                                              SEQ ID NO: 2
   1 mcaerlgqfm tlalvlatfd pargtdatnp pegpqdrssq qkgrlslqnt aeiqhclvna 61 gdvgcgvfec fennsceirg lhgicmtflh nagkfdaqgk sfikdalkck ahalrhrfgc 121 isrkcpaire mvsqlqrecy lkhdlcaaaq entrvivemi hfkdlllhep yvdlvnlllt 181 cgeevkeait hsvqvqceqn wgslcsilsf ctsaiqkppt apperqpqvd rtklsrahhg 241 eaghhlpeps sretgrgakg ergskshpna hargrvgglg aqgpsgssew edeqseysdi 301 rr PAPP-A (=pappalysin-1) precursor [Homo sapiens]
UniProtKB/Swiss-Prot: Q13219.3
                                                              SEQ ID NO: 3
   1 mrlwswvlhl gllsaalgcg laerprrarr dpragrpprp aagpatcatr aargrraspp 61 pppppggawe avrvprrrqq reargateep sppsralyfs grgeqlrlra dlelprdaft 121 lqvwlraegg qrspavitgl ydkcsyisrd rgwvvgihti sdqdnkdpry ffslktdrar 181 qvttinahrs ylpgqwvyla atydgqfmkl yvngaqvats geqvggifsp ltqkckvlml 241 ggsalnhnyr gyiehfslwk vartqreils dmethgahta lpqlllqenw dnvkhawspm 301 kdgsspkvef snahgflldt slepplcgqt lcdntevias ynqlssfrqp kvvryrvvnl 361 yeddhknptv treqvdfqhh qlaeafkqyn isweldvlev snsslrrrli lancdiskig 421 dencdpecnh tltghdggdc rhlrhpafvk kqhngvcdmd cnyerfnfdg geccdpeitn 481 vtqtcfdpds phrayldvne lknilkldgs thlniffaks seeelagvat wpwdkealmh 541 lggivlnpsf ygmpghthtm iheighslgl yhvfrgisei qscsdpcmet epsfetgdlc 601 ndtnpapkhk scgdpgpgnd tcgfhsffnt pynnfmsyad ddctdsftpn qvarmhcyld 661 lvyqgwqpsr kpapvalapq vlghttdsvt lewfppidgh fferelgsac hlclegrilv 721 qyasnasspm pcspsghwsp reaeghpdve qpckssvrtw spnsavnpht vppacpepqg 781 cyleleflyp lvpesltiwv tfvstdwdss gavndiklla vsgknislgp qnvfcdvplt 841 irlwdvgeev ygiqiytlde hleidaamlt stadtplclq ckplkykvvr dpplqmdvas 901 ilhlnrkfvd mdlnlgsvyq ywvitisgte esepspavty ihgsgycgdg iiqkdqgeqc 961 ddmnkingdg cslfcrqevs fncidepsrc yfhdgdgvce efeqktsikd cgvytpqgfl 1021 dqwasnasvs hqdqqcpgwv iigqpaasqv crtkvidlse gisqhawypc tisypysqla 1081 qttfwlrayf sqpmvaaavi vhlvtdgtyy gdqkqetisv qlldtkdqsh dlglhvlscr 1141 nnpliipvvh dlsqpfyhsq avrvsfsspl vaisgvalrs fdnfdpvtls scqrgetysp 1201 aeqscvhfac ektdcpelav enaslncsss dryhgaqctv scrtgyvlqi rrddeliksq 1261 tgpsvtvtct egkwnkqvac epvdcsipdh hqvyaasfsc pegttfgsqc sfqcrhpaql 1321 kgnnslltcm edglwsfpea lcelmclapp pvpnadlqta rcrenkhkvg sfckykckpg 1381 yhvpgssrks kkrafktqct qdgswqegac vpvtcdpppp kfhglyqctn gfqfnsecri
```

-continued

```
1441 kcedsdasqg lgsnvihcrk dgtwngsfhv cqemqgqcsv pnelnsnlkl qcpdgyaigs 1501 ecatscldhn sesiilpmnv tvrdiphwln ptrvervvct aglkwyphpa lihcvkgcep 1561 fmgdnycdai nnrafcnydg gdcctstvkt kkvtpfpmsc dlqgdcacrd pqaqehsrkd 1621 lrgyshg
```

PAPP-A2 (=pappalysin-2) precursor [Homo sapiens]
UniProtKB/Swiss-Prot: Q9BXP8.4
SEQ ID NO: 4

```
   1 mmclkilris lailagwalc sanselgwtr kkslverehl nqvllegerc wlgakvrrpr 61 aspqhhlfgv ypsragnylr pypvgeqeih htgrskpdte gnavslvppd ltenpaglrg 121 aveepaapwv gdspigqsel lgdddaylgn qrskeslgea giqkgsamaa ttttaifttl 181 nepkpetqrr gwaksrqrrq vwkrraedgq gdsgisshfq pwpkhslkhr vkksppeesn 241 qnggegsyre aetfnsqvgl pilyfsgrre rlllrpevla eipreaftve awvkpeggqn 301 npaiiagvfd ncshtvsdkg walgirsgkd kgkrdarfff slctdrvkka tilishsryq 361 pgtwthvaat ydgrhmalyv dgtqvassld qsgplnspfm ascrslllgg dssedghyfr 421 ghlgtlvfws talpqshfqh ssqhssgeee atdlvltasf epvntewvpf rdekyprlev 481 lqgfepepei lsplqpplcg qtvcdnveli sqyngywplr gekviryqvv nicddeglnp 541 ivseeqirlq healneafsr yniswqlsvh qvhnstlrhr vvlvncepsk igndhcdpec 601 ehpltgydgg dcrlqgrcys wnrrdglchv ecnnmlndfd dgdccdpqva dvrktcfdpd 661 spkraymsvk elkealqlns thflniyfas svredlagaa twpwdkdavt hlggivlspa 721 yygmpghtdt mihevghvlg lyhvfkgvse rescndpcke tvpsmetgdl cadtaptpks 781 elcrepepts dtcgftrfpg apftnymsyt ddnctdnftp nqvarmhcyl dlvyqqwtes 841 rkptpipipp mvigqtnksl tihwlppisg vvydrasgsl cgactedgtf rqyvhtassr 901 rvcdssgywt peeavgppdv dqpcepslqa wspevhlyhm nmtvpcpteg cslellfqhp 961 vqadtltlwv tsffmessqv lfdteillen kesvhlgpld tfcdipltik lhvdgkvsgv 1021 kvytfderie idaalltsqp hsplcsgcrp vryqvlrdpp fasglpvvvt hshrkftdve 1081 vtpgqmyqyq vlaeaggelg easpplnhih gapycgdgkv serlgeecdd gdlvsgdgcs 1141 kvceleegfn cvgepslcym yegdgicepf erktsivdcg iytpkgyldq watraysshe 1201 dkkkcpvslv tgephslict syhpdlpnhr pltgwfpcva senetqddrs eqpegslkke 1261 devwlkvcfn rpgearaifi flttdglvpg ehqqptvtly ltdvrgsnhs lgtyglscqh 1321 npliinvthh qnvlfhhtts vllnfssprv gisavalrts sriglsapsn cisedegqnh 1381 qgqscihrpc gkqdscpsll ldhadvvnct sigpglmkca itcqrgfalq assgqyirpm 1441 qkeilltcss ghwdqnvscl pvdcgvpdps lvnyanfscs egtkflkrcs iscvppaklq 1501 glspwltcle dglwslpevy cklecdappi ilnanlllph clqdnhdvgt ickyeckpgy 1561 yvaesaegkv rnkllkiqcl eggiweqgsc ipvvcepppp vfegmyectn gfsldsqcvl 1621 ncnqereklp ilctkeglwt qefklcenlq gecppppsel nsveykceqg ygigavcspl 1681 cvippsdpvm lpenitadtl ehwmepvkvq sivctgrrqw hpdpvlvhci qscepfqadg 1741 wcdtinnray chydggdccs stlsskkvip faadcdldec tcrdpkaeen q
```

Stanniocalcin-1 (=STC1) cDNA [Homo sapiens]
Human Stanniocalcin 1 cDNA
www.ncbi.nlm.nih.gov/CCDS/CcdsBrowse.cgi?REQUEST=CCDS&GO=MainBro
wse&DATA=CCDS6043.1
SEQ ID NO: 5
ATGCTCCAAAACTCAGCAGTGCTTCTGGTGCTGGTGATCAGTGCTTCTGCAACCC

ATGAGGCGGAGCAGA ATGACTCTGTGAGCCCCAGGAAATCCCGAGTGGCGGCT

-continued

```
CAAAACTCAGCTGAAGTGGTTCGTTGCCTCAA CAGTGCTCTACAGGTCGGCTGC

GGGGCTTTTGCATGCCTGGAAAACTCCACCTGTGACACAGATGGGATG TATGAC

ATCTGTAAATCCTTCTTGTACAGCGCTGCTAAATTTGACACTCAGGGAAAAGCATT

CGTCAAAG AGAGCTTAAAATGCATCGCCAACGGGGTCACCTCCAAGGTCTTCCT

CGCCATTCGGAGGTGCTCCACTTT CCAAAGGATGATTGCTGAGGTGCAGGAAGA

GTGCTACAGCAAGCTGAATGTGTGCAGCATCGCCAAGCGG AACCCTGAAGCCAT

CACTGAGGTCGTCCAGCTGCCCAATCACTTCTCCAACAGATACTATAACAGACTTG

TCCGAAGCCTGCTGGAATGTGATGAAGACACAGTCAGCACAATCAGAGACAGCC

TGATGGAGAAAATTGG GCCTAACATGGCCAGCCTCTTCCACATCCTGCAGACAG

ACCACTGTGCCCAAACACACCCACGAGCTGAC TTCAACAGGAGACGCACCAATG

AGCCGCAGAAGCTGAAAGTCCTCCTCAGGAACCTCCGAGGTGAGGAGG ACTCT

CCCTCCCACATCAAACGCACATCCCATGAGAGTGCATAA
```

Stanniocalcin-2 (=STC2) cDNA [Homo sapiens]
Human Stanniocalcin 2 cDNA
www.ncbi.nlm.nih.gov/CCDS/CcdsBrowse.cgi?REQUEST=GV&DATA=274786&
BUILDS=CURRENTBUILDS

SEQ ID NO: 6

```
ATGTGTGCCGAGCGGCTGGGCCAGTTCATGACCCTGGCTTTGGTGTTGGCCACC

TTTGACCCGGCGCGGG GGACCGACGCCACCAACCCACCCGAGGGTCCCCAAGA

CAGGAGCTCCCAGCAGAAAGGCCGCCTGTCCCT GCAGAATACAGCGGAGATCC

AGCACTGTTTGGTCAACGCTGGCGATGTGGGGTGTGGCGTGTTTGAATGT TTCG

AGAACAACTCTTGTGAGATTCGGGGCTTACATGGGATTTGCATGACTTTTCTGCAC

AACGCTGGAA AATTTGATGCCCAGGGCAAGTCATTCATCAAAGACGCCTTGAAAT

GTAAGGCCCACGCTCTGCGGCACAG GTTCGGCTGCATAAGCCGGAAGTGCCCG

GCCATCAGGGAAATGGTGTCCCAGTTGCAGCGGGAATGCTAC CTCAAGCACGAC

CTGTGCGCGGCTGCCCAGGAGAACACCCGGGTGATAGTGGAGATGATCCATTTC

AAGG ACTTGCTGCTGCACGAACCCTACGTGGACCTCGTGAACTTGCTGCTGACC

TGTGGGGAGGAGGTGAAGGA GGCCATCACCCACAGCGTGCAGGTTCAGTGTGA

GCAGAACTGGGGAAGCCTGTGCTCCATCTTGAGCTTC TGCACCTCGGCCATCCA

GAAGCCTCCCACGGCGCCCCCCGAGCGCCAGCCCCAGGTGGACAGAACCAAGC

TCTCCAGGGCCCACCACGGGGAAGCAGGACATCACCTCCCAGAGCCCAGCAGT

AGGGAGACTGGCCGAGG TGCCAAGGGTGAGCGAGGTAGCAAGAGCCACCCAAA

CGCCCATGCCCGAGGCAGAGTCGGGGGCCTTGGG GCTCAGGGACCTTCCGGA

AGCAGCGAGTGGGAAGACGAACAGTCTGAGTATTCTGATATCCGGAGGTGA
```

Murine PAPP-A2 primer

SEQ ID NO: 7

(5'-CCGAGAGGTCAGGAGAGCAG-3'(nt. 3120-3101)
and

Murine PAPP-A2 primer

SEQ ID NO: 8

5'-GAGCTTCTCTTTTAGTCTGCCCCC

Murine PAPP-A2 primer

SEQ ID NO: 9

(5'-CCGGGGTACCATGATGTGTTGGAAGGTCCTGAG

Murine PAPP-A2 primer

SEQ ID NO: 10

5'-GATGGTGAGCGGTATGTCACAA

Murine PAPP-A2 primer

-continued

```
                                                        SEQ ID NO: 11
5'-CCGGTCCAGGCGGATACCCT

Murine PAPP-A2 primer
                                                        SEQ ID NO: 12
5'-GATCTCTAGATTACTGGTTTTCTTCTGCCTTGGGG STC2 primer
                                                        SEQ ID NO: 13
5'-GCACAGGTTCGGCGCCATAAGCCGGAAGTG STC2 primer
                                                        SEQ ID NO: 14
5'-CACTTCCGGCTTATGGCGCCGAACCTGTGC STC2 primer
                                                        SEQ ID NO: 15
5'-CAGCGTGCAGGTTCAGGCTGAGCAGAACTGGGGAAG STC2 primer
                                                        SEQ ID NO: 16
5'-CTTCCCCAGTTCTGCTCAGCCTGAACCTGCACGCTG STC2 primer
                                                        SEQ ID NO: 17
5'-GAACTGGGGAAGCCTGGCCTCCATCTTGAGCTTC STC2 primer
                                                        SEQ ID NO: 18
5'-GAAGCTCAAGATGGAGGCCAGGCTTCCCCAGTTC
```

---

The invention claimed is:

1. An assay for screening if an agent is capable of antagonizing complex formation between a stanniocalcin and a Pappalysin comprising the steps of:
   (a) providing a Pappalysin polypeptide and a stanniocalcin polypeptide, wherein the Pappalysin is PAPP-A (SEQ ID NO:3) or PAPP-A2 (SEQ ID NO:4) and wherein the stanniocalcin is STC1 (SEQ ID NO: 1) or STC2 (SEQ ID NO:2),
   (b) providing said agent,
   (c) incubating said agent with said Pappalysin and stanniocalcin,
   (d) detecting the presence or absence of interacting Pappalysin and stanniocalcin, and
   (e) on the basis of the presence or absence of interacting Pappalysin and stanniocalcin in step d, determining whether said agent is capable of antagonizing complex formation between Pappalysin and stanniocalcin.

2. The assay of claim 1, wherein step (d) is carried out with a detection method selected from the group consisting of western blot, stained protein gel, autoradiography, and ELISA.

3. The assay of claim 1, wherein said agent is an antibody.

4. The assay of claim 1, wherein the Pappalysin, the stanniocalcin, or both further comprise a radiolabel.

5. The assay of claim 1, wherein said agent is incubated with said Pappalysin and stanniocalcin for a minimum of 30 minutes.

6. An assay for screening if an agent is capable of antagonizing complex formation between a stanniocalcin and a Pappalysin comprising the steps of:
   (a) providing a Pappalysin polypeptide and a stanniocalcin polypeptide, wherein the Pappalysin is PAPP-A (SEQ ID NO:3) or PAPP-A2 (SEQ ID NO:4) and wherein the stanniocalcin is STC1 (SEQ ID NO: 1) or STC2 (SEQ ID NO:2),
   (b) providing said agent,
   (c) incubating said agent with Pappalysin and stanniocalcin,
   (d) providing an IGF binding protein,
   (e) incubating said IGF binding protein with agent, Pappalysin and stanniocalcin,
   (f) detecting the presence or absence of cleaved IGF binding protein, and
   (g) on the basis of the presence or absence of cleaved IGF binding protein in step f determine whether said agent is capable of antagonizing complex formation between Pappalysin and stanniocalcin.

7. The assay of claim 6, wherein said IGF binding protein is labelled with a radiolabel.

8. The assay of claim 6, wherein said IGF binding protein is a binding protein selected from the group consisting of IGF binding protein 4, IGF binding protein 5 and/or IGF binding protein 2.

9. The assay of claim 6, wherein step (f) is carried out with a detection method selected from the group consisting of autoradiography, western blot, stained protein gel, and ELISA.

10. The assay of claim 6, wherein step (c) is incubated for a minimum of 4 hours, or for 16 hours.

11. The assay of claim 6, wherein said agent is an antibody.

* * * * *